US012636283B2

(12) United States Patent
Arsenijevic et al.

(10) Patent No.: US 12,636,283 B2
(45) Date of Patent: May 26, 2026

(54) INHIBITION OF PRC2 SUBUNITS TO TREAT EYE DISORDERS

(71) Applicant: FONDATION ASILE DES AVEUGLES, Lausanne (CH)

(72) Inventors: Yvan Arsenijevic, Lausanne (CH); Kamdem Martial Mbefo, Lausanne (CH)

(73) Assignee: FONDATION ASILE DES AVEUGLES, Lausanne (CH)

( * ) Notice: Subject to any disclaimer, the term of this patent is extended or adjusted under 35 U.S.C. 154(b) by 1036 days.

(21) Appl. No.: 17/143,293

(22) Filed: Jan. 7, 2021

(65) Prior Publication Data

US 2021/0213013 A1     Jul. 15, 2021

Related U.S. Application Data

(63) Continuation of application No. PCT/EP2019/067784, filed on Jul. 2, 2019.

(30) Foreign Application Priority Data

Jul. 9, 2018     (EP) .................................... 18182551

(51) Int. Cl.
A61K 31/496     (2006.01)
A61K 31/5377     (2006.01)
A61K 45/06     (2006.01)
A61P 27/02     (2006.01)

(52) U.S. Cl.
CPC ........ A61K 31/496 (2013.01); A61K 31/5377 (2013.01); A61K 45/06 (2013.01); A61P 27/02 (2018.01)

(58) Field of Classification Search
CPC .. A61K 31/496; A61K 31/5377; A61K 45/00; A61K 45/06; A61P 27/02
See application file for complete search history.

(56) References Cited

U.S. PATENT DOCUMENTS

| 8,410,088 | B2 | 4/2013 | Kuntz et al. |
| 8,536,179 | B2 | 9/2013 | Miller et al. |
| 8,637,509 | B2 | 1/2014 | Burgess et al. |
| 8,691,507 | B2 | 4/2014 | Copeland et al. |
| 8,765,732 | B2 | 7/2014 | Kuntz et al. |
| 8,765,792 | B2 | 7/2014 | Knight et al. |
| 8,846,935 | B2 | 9/2014 | Duquenne et al. |
| 8,975,291 | B2 | 3/2015 | Brackley et al. |
| 9,006,242 | B2 | 4/2015 | Kuntz et al. |
| 9,018,382 | B2 | 4/2015 | Duquenne et al. |
| 9,040,515 | B2 | 5/2015 | Edwards et al. |
| 9,073,924 | B2 | 7/2015 | Burgess et al. |
| 9,085,583 | B2 | 7/2015 | Albrecht et al. |
| 9,090,562 | B2 | 7/2015 | Kuntz et al. |
| 9,114,141 | B2 | 8/2015 | Miller et al. |
| 9,242,962 | B2 | 1/2016 | Bassil et al. |
| 9,371,331 | B2 | 6/2016 | Albrecht et al. |
| 9,376,422 | B2 | 6/2016 | Kuntz et al. |
| 9,382,234 | B2 | 7/2016 | Knight et al. |
| 9,402,836 | B2 | 8/2016 | Brackley et al. |
| 9,446,041 | B2 | 9/2016 | Bassil et al. |
| 9,469,646 | B2 | 10/2016 | Albrecht et al. |
| 9,481,666 | B2 | 11/2016 | Kania et al. |
| 9,505,745 | B2 | 11/2016 | Blackledge, Jr. et al. |
| 9,518,038 | B2 | 12/2016 | Zhang et al. |
| 9,527,837 | B2 | 12/2016 | Yu et al. |
| 9,549,931 | B2 | 1/2017 | Kuntz et al. |
| 9,556,157 | B2 | 1/2017 | Burgess et al. |
| 9,562,041 | B2 | 2/2017 | Burgess et al. |
| 9,624,205 | B2 | 4/2017 | Campbell |
| 9,649,307 | B2 | 5/2017 | Miller et al. |
| 9,701,666 | B2 | 7/2017 | Kuntz et al. |
| 9,718,838 | B2 | 8/2017 | Guo et al. |
| 9,738,630 | B2 | 8/2017 | Kim et al. |
| 9,745,305 | B2 | 8/2017 | Albrecht et al. |
| 9,790,212 | B2 | 10/2017 | Blackledge, Jr. et al. |
| 9,822,103 | B2 | 11/2017 | Seitz et al. |
| 9,855,275 | B2 | 1/2018 | Kuntz et al. |

(Continued)

FOREIGN PATENT DOCUMENTS

| CN | 103110621 A | 5/2013 |
| CN | 103690528 A | 4/2014 |

(Continued)

OTHER PUBLICATIONS

Fan et. al., CN 106692152 A, English translation, publ. May 24, 2017 (Year: 2017).*
Houston et. al., Int. Ophthalmol. Clin., vol. 51(1), pp. 77-91, publ. 2011 (Year: 2011).*
Knutson et. al., PNAS, vol. 110(19), pp. 7922-7927, publ. May 7, 2013 (Year: 2013).*
Fan et. al., CN 106963765 A, publ. Jul. 21, 2017, English translation (Year: 2017).*

(Continued)

Primary Examiner — Sarah Pihonak

(74) Attorney, Agent, or Firm — Agris and von Natzmer LLP; Joyce von Natzmer

(57) ABSTRACT

The present disclosure provides inhibitors of one or more subunits of polycomb repressive complex 2 (PRC2) for use in the prevention or the treatment of an eye disorder in a subject in need thereof and methods for treating an eye disorder, e.g. non-cancer disorders, in a subject using a therapeutically effective amount of one or more inhibitors of a subunit of polycomb repressive complex 2 (PRC2).

Figure 1:
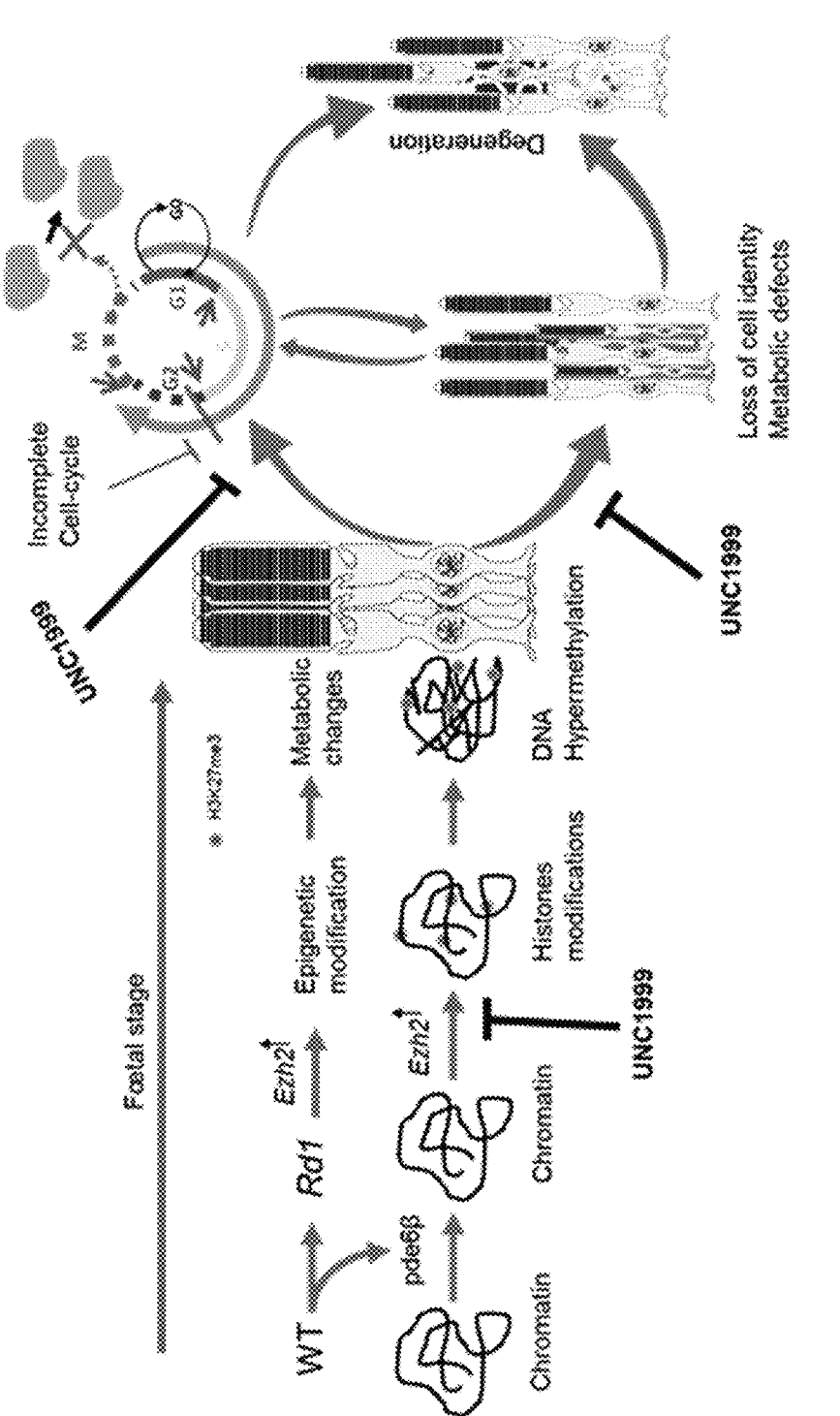

In certain embodiments of the methods of the disclosure, the eye disorders are characterized by degeneration or cell death of retinal neurons.

In certain embodiments of the methods of the disclosure, the subunit of PRC2 is EZH1 or EZH2, and the inhibitor is an inhibitor of H3K27 trimethylation.

17 Claims, 13 Drawing Sheets

Specification includes a Sequence Listing.

(56)　　　　　　References Cited

U.S. PATENT DOCUMENTS

| 9,956,210 | B2 | 5/2018 | Burgess et al. | |
|---|---|---|---|---|
| 9,969,716 | B2 | 5/2018 | Albrecht et al. | |
| 9,980,952 | B2 | 5/2018 | Albrecht et al. | |
| 2017/0049746 | A1 | 2/2017 | Harn et al. | |
| 2017/0333375 | A1* | 11/2017 | Campochiaro | A61P 27/02 |
| 2021/0128600 | A1* | 5/2021 | Rauch | A61K 31/7105 |

FOREIGN PATENT DOCUMENTS

| CN | 103690529 | A | | 4/2014 | |
|---|---|---|---|---|---|
| CN | 103690530 | A | | 4/2014 | |
| CN | 103690531 | A | | 4/2014 | |
| CN | 103845324 | A | | 6/2014 | |
| CN | 103845325 | A | | 6/2014 | |
| CN | 106692152 | A | * | 5/2017 | |
| CN | 106963765 | A | * | 7/2017 | A61K 31/496 |
| CN | 106963765 | B | | 4/2020 | |
| EP | 3338775 | A1 | | 6/2018 | |
| WO | 2011140324 | A1 | | 11/2011 | |
| WO | 2011140325 | A1 | | 11/2011 | |
| WO | 2012005805 | A1 | | 1/2012 | |
| WO | 2012034132 | A2 | | 3/2012 | |
| WO | 2012068589 | A2 | | 5/2012 | |
| WO | 2012075080 | A1 | | 6/2012 | |
| WO | 2012118812 | A2 | | 9/2012 | |
| WO | 2012142504 | A1 | | 10/2012 | |
| WO | 2012142513 | A1 | | 10/2012 | |
| WO | 2013039988 | A1 | | 3/2013 | |
| WO | 2013067296 | A1 | | 5/2013 | |
| WO | 2013120104 | A2 | | 8/2013 | |
| WO | 2013155317 | A1 | | 10/2013 | |
| WO | 2013155464 | A1 | | 10/2013 | |
| WO | 2013173441 | A2 | | 11/2013 | |
| WO | 2014048313 | A1 | | 4/2014 | |
| WO | 2014049488 | A1 | | 4/2014 | |
| WO | 2014062732 | A1 | | 4/2014 | |
| WO | WO-2014062720 | A2 | * | 4/2014 | A61K 31/4412 |
| WO | 2014062733 | A2 | | 6/2014 | |
| WO | 2014097041 | A1 | | 6/2014 | |
| WO | 2014100646 | A1 | | 6/2014 | |
| WO | 2014100665 | A1 | | 6/2014 | |
| WO | WO-2014100080 | A1 | * | 6/2014 | A61K 31/11 |
| WO | 2014107277 | A1 | | 7/2014 | |
| WO | 2014124418 | A1 | | 8/2014 | |
| WO | 2014151142 | A1 | | 9/2014 | |
| WO | 2014155301 | A1 | | 10/2014 | |
| WO | 2014172044 | A1 | | 10/2014 | |
| WO | 2014177982 | A1 | | 11/2014 | |
| WO | 2014190035 | A2 | | 11/2014 | |
| WO | 2014195919 | A1 | | 12/2014 | |
| WO | 2015004618 | A1 | | 1/2015 | |
| WO | 2015010049 | A1 | | 1/2015 | |
| WO | 2015010078 | A2 | | 1/2015 | |
| WO | 2015023915 | A1 | | 2/2015 | |
| WO | 2015057859 | A1 | | 4/2015 | |
| WO | 2015077193 | A1 | | 5/2015 | |
| WO | 2015077194 | A1 | | 5/2015 | |
| WO | 2015104677 | A1 | | 7/2015 | |
| WO | 2015110999 | A1 | | 7/2015 | |
| WO | 2015132765 | A1 | | 9/2015 | |
| WO | 2015193765 | A1 | | 12/2015 | |
| WO | 2015193768 | A1 | | 12/2015 | |
| WO | 2015200650 | A1 | | 12/2015 | |
| WO | 2016066697 | A1 | | 5/2016 | |
| WO | 2016073903 | A1 | | 5/2016 | |
| WO | 2016073956 | A1 | | 5/2016 | |
| WO | 2016089804 | A1 | | 6/2016 | |
| WO | 2016130396 | A1 | | 8/2016 | |
| WO | 2017028602 | A1 | | 2/2017 | |
| WO | 2017035060 | A1 | | 3/2017 | |
| WO | 2017061957 | A1 | | 4/2017 | |
| WO | 2017184999 | A1 | | 10/2017 | |
| WO | 2017191545 | A1 | | 11/2017 | |
| WO | 2017214553 | A1 | | 12/2017 | |
| WO | 2018075598 | A1 | | 4/2018 | |
| WO | 2019115472 | A1 | | 6/2019 | |

OTHER PUBLICATIONS

Damato et. al., Saudi J. Ophthalmology, vol. 26, pp. 137-144, publ. 2012 (Year: 2012).*

Bhutto et. al., Molecular Aspects of Med., vol. 33, pp. 295-317, publ. 2012 (Year: 2012).*

Shikari et. al., J. Clin. Ophthalmol. & Res., vol. 4, pp. 51-59, publ. 2016 (Year: 2016).*

Bisserier et. al., Blood, vol. 131(19), pp. 2125-2137, publ. May 2018 (Year: 2018).*

Apexbt: "CPI-1205 product information from APExBIO website", available at https://www.apexbt.com/cpi-1205.html (retrieved on Nov. 17, 2020).

Cayman Chemical: "CPI-169 product information from Cayman Chemical website", available at https://www.caymanchem.com/product/18299/cpi-169 (retrieved on Nov. 17, 2020).

Cayman Chemical: "CPI-360 product information from Cayman Chemical website", available at https://www.caymanchem.com/product/19125/cpi-360 (retrieved on Nov. 17, 2020).

Cayman Chemical: "Deazaneplanocin product information from Cayman Chemical website", available at https://www.caymanchem.com/product/13828/3-deazaneplanocin-a.

Cayman Chemical: "EI1 product information from Cayman Chemical website", available at https://www.caymanchem.com/product/19146/ei1 (retrieved on Nov. 17, 2020).

Cayman Chemical: "EPZ005687 product information from Cayman Chemical website", available at https://www.caymanchem.com/product/13966/epz005687 (retrieved on Nov. 17, 2020).

Cayman Chemical: "EPZ011989 product information from Cayman Chemical website", available at https://www.caymanchem.com/product/19161/epz011989 (retrieved on Nov. 17, 2020).

Cayman Chemical: "EPZ-6438 product information from Cayman Chemical website", available at https://www.caymanchem.com/product/16174 (retrieved on Nov. 17, 2020).

Cayman Chemical: "GSK126 product information from Cayman Chemical website", available at https://www.caymanchem.com/product/15415/gsk126 (retrieved on Nov. 17, 2020).

Cayman Chemical: "GSK343 product information from Cayman Chemical website", available at https://www.caymanchem.com/product/14094 (retrieved on Mar. 18, 2020).

Cayman Chemical: "GSK503 product information from Cayman Chemical website", available at https://www.caymanchem.com/product/18531/gsk503 (retrieved on Nov. 17, 2020).

Cayman Chemical: "JQEZ5 product information from Cayman Chemical website", available at https://www.caymanchem.com/product/27457/jqez5 (retrieved on Nov. 17, 2020).

Pubchem; "PF-06821497 public compound information from PubChem website", available at https://pubchem.ncbi.hlm.nih.gov/compound/118572065 (retrieved on Nov. 17, 2020).

Cayman Chemical: "Sinefungin product information from Cayman Chemical website", available at https://www.caymanchem.com/product/13829/sinefungin.

Sigma Aldrich: "UNC1999 product information from Sigma Aldrich website", available at https://www.sigmaaldrich.com/catalog/product/sigma/sml0778?lang=en&region=US (retrieved on Nov. 17, 2020).

Cayman Chemical: "ZLD1039 product information from Cayman Chemical website", available at https://www.caymanchem.com/product/19218/zld1039 (retrieved on Nov. 17, 2020).

Zhang, Oncogenic Deregulation of EZH2 as an Opportunity for Targeted Therapy in Lung Cancer, Cancer Discovery, Sep. 2016, 1007.

Wahlin et al., "Epigenetics and Cell Death: DNA Hypermethylation in Programmed Retinal Cell Death", PLoS on, vol. 8, Issue 11, Nov. 2013, pp. 1-13.

WIPO, Written Opinion issued for PCT/EP2019/067784 of Jan. 16, 2020.

Xu et al., "Selective inhibition of EZH2 and EZH1 enzymatic activity by a small molecule suppresses MLL-rearranged leukemia", Blood, vol. 125, Issue 2, Jan. 8, 2015, pp. 346-357.

(56)                    References Cited

OTHER PUBLICATIONS

Yoo et al., "EZH2 methyltransferase and H3K27 methylation in breast cancer", Int J Biol Sci., vol. 8, No. 1, Nov. 18, 2011 pp. 59-65.

Yuzawa et al., "Assessing quality of life in the treatment of patients with age-related macular degeneration: clinical research findings and recommendations for clinical practice" Clin Ophthalmol., vol. 7, Jul. 1, 2013, pp. 1325-1332.

Zencak et al., "Retinal degeneration depends on Bmi1 function and reactivation of cell cycle proteins", PNAS, Jan. 28, 2013, pp. E593-E601.

Zhang et al., "Oncogenic Deregulation of EZH2 as an Opportunity for Targeted Therapy in Lung Cancer", Cancer Discovery, vol. 6, Issue 9, Jun. 1, 2016, pp. 1007-1021.

Zhang Jianmin et al, "Ezh2 maintains retinal progenitor proliferation, transcriptional integrity, and the timing of late differentiation", Developmental Biology, vol. 403, No. 2, 2015, p. 128-138.

Zheng et al., "DZNep inhibits H3K27me3 deposition and delays retinal degeneration in the rd1 mice", Cell Death Dis. 9, vol. 3, No. 310, pp. 1-14 (Feb. 2018).

"CPI-1205 product information from APExBIO website", available at https://www.apexbt.com/cpi-1205.html (retrieved on Nov. 17, 2020).

"CPI-169 product information from Cayman Chemical website", available at https://www.caymanchem.com/product/18299/cpi-169 (retrieved on Nov. 17, 2020).

"CPI-360 product information from Cayman Chemical website", available at https://www.caymanchem.com/product/19125/cpi-360 (retrieved on Nov. 17, 2020).

"Deazaneplanocin product information from Cayman Chemical website", available at https://www.caymanchem.com/product/13828/3-deazaneplanocin-a, 2020.

"Ei1 product information from Cayman Chemical website", available at https://www.caymanchem.com/product/19146/ei1 (retrieved on Nov. 17, 2020).

"EPZ005687 product information from Cayman Chemical website", available at https://www.caymanchem.com/product/13966/epz005687 (retrieved on Nov. 17, 2020).

"EPZ011989 product information from Cayman Chemical website", available at https://www.caymanchem.com/product/19161/epz011989 (retrieved on Nov. 17, 2020).

"EPZ-6438 product information from Cayman Chemical website", available at https://www.caymanchem.com/product/16174 (retrieved on Nov. 17, 2020).

"GSK126 product information from Cayman Chemical website", available at https://www.caymanchem.com/product/15415/gsk126 (retrieved on Nov. 17, 2020).

"GSK343 product information from Cayman Chemical website", available at https://www.caymanchem.com/product/14094 (retrieved on Nov. 17, 2020).

"GSK503 product information from Cayman Chemical website", available at https://www.caymanchem.com/product/18531/gsk503 (retrieved on Nov. 17, 2020).

"JQEZ5 product information from Cayman Chemical website", available at https://www.caymanchem.com/product/27457/jqez5 (retrieved on Nov. 17, 2020).

"PF-06821497 public compound information from PubChem website", available at https://pubchem.ncbi.nlm.nih.gov/compound/118572065 (retrieved on Nov. 17, 2020).

"Sinefungin product information from Cayman Chemical website", available at https://www.caymanchem.com/product/13829/sinefungin, 2020.

"UNC1999 product information from Sigma Aldrich website", available at https://www.sigmaaldrich.com/catalog/product/sigma/sml0778?lang=en&region=US (retrieved on Nov. 17, 2020).

"ZLD1039 product information from Cayman Chemical website", available at https://www.caymanchem.com/product/19218/zld1039 (retrieved on Nov. 17, 2020).

Andrews et al., "miR-302 regulates retinal epithelial cell fate; New insights into TGFB signalling reveal a role for for the polycomb protein EZH2", Investigative Ophthalmology & Visual Science, vol. 5, Apr. 2014, pp. 1-2.

Arrowsmith et al., "The promise and peril of chemical probes", Nature Chemical Biology, vol. 11, Aug. 2015, pp. 536-541.

Arroyo et al., "Photoreceptor apoptosis in human retinal detachment", Am J Ophthalmol., vol. 139, Issue 4, Apr. 1, 2005, pp. 605-610.

Barhoum et al., "Functional and structural modifications during retinal degeneration in the rd10 mouseFunctional and structural modifications during retinal degeneration in the rd10 mouse", Neuroscience, vol. 155, Issue 3, Aug. 26, 2008, pp. 698-713.

Bemelmans et al., "Lentiviral gene transfer of RPE65 rescues survival and function of cones in a mouse model of Leber congenital amaurosis", PLoS Med., vol. 3, Issue 10, Oct. 2006, pp. 1892-1903.

Bracken et al., "Genome-wide mapping of Polycomb target genes unravels their roles in cell fate transitions", Genes Dev, vol. 20, Issue 9, Apr. 17, 2006, pp. 1123-1136.

Cao et al., "Role of histone H3 lysine 27 methylation in Polycomb-group silencing", Science., vol. 298, Issue 5595, Nov. 1, 2002, pp. 1039-1043.

Chang et al., "Two mouse retinal degenerations caused by missense mutations in the beta-subunit of rod cGMP phosphodiesterase gene" Vision Research, vol. 47, Issue 5, Mar. 2007, pp. 624-633.

Chase et al., "Aberrations of EZH2 in cancer", Clinical Cancer Research, vol. 17, Issue 9, May 2011, pp. 2613-2618.

Cideciyan et al., "Human retinal gene therapy for Leber congenital amaurosis shows advancing retinal degeneration despite enduring visual improvement", PNAS, vol. 17, Issue 9, Feb. 5, 2013, pp. E517-E525.

Czermin et al., "Drosophila enhancer of Zeste/ESC complexes have a histone H3 methyltransferase activity that marks chromosomal Polycomb sites", Cell, vol. 111, Issue 2, Oct. 18, 2002, pp. 185-196.

Database WPI Thomson Scientific, London, GB; vol. 2017, No. 46, AN 2017-40876F, XP002794515 (see CN 106692152 A (UNIV Shanghai Ninth Peoples Hospital AFF) May 24, 2017 (May 24, 2017)).

Database WPI Thomson Scientific, London, GB; vol. 2017, No. 63, AN 2017-51431J, XP002794514 (see CN 106963765 A (UNIV Shanghai Ninth Peoples Hospital AFF) Jul. 21, 2017 (Jul. 21, 2017)).

Fan et al., Database WPI Week 201746, XP-002794515, (D2 of International Search Report of PCT/EP2019/067784), Abstract to CN106962152 (May 24, 2017).

Fan et al., Database WPI Week 201763, XP-002794514, (D1 of International Search Report of PCT/EP2019/067784), Abstract to CN106963765 (Jul. 21, 2017).

Farber et al., "Cyclic guanosine monophosphate: elevation in degenerating photoreceptor cells of the C3H mouse retina", Science., vol. 186, Issue 4162, Nov. 1, 1974, pp. 449-451.

Gekeler et al., "Implantation, removal and replacement of subretinal electronic implants for restoration of vision in patients with retinitis pigmentosa", Curr Opin Ophthalmol., vol. 29, Issue 3, May 2018, pp. 239-247.

Gimenez et al., "A simple polymerase chain reaction assay for genotyping the retinal degeneration mutation (Pdeb (rd1)) in FVB/N-derived transgenic mice", Lab Anim., vol. 35, Issue 2, 2001, pp. 153-160.

Hisatomi et al., "HIV protease inhibitors provide neuroprotection through inhibition of mitochondrial apoptosis in mice", The Journal of Clinical Investigation, vol. 118, No. 6, Jun. 2008, pp. 2025-2038.

Hisatomi et al., "Relocalization of apoptosis-inducing factor in photoreceptor apoptosis induced by retinal detachment in vivo", Am J Pathol., vol. 158, No. 4, Apr. 2001, pp. 1271-1280.

Jacobson et al., "Gene therapy for leber congenital amaurosis caused by RPE65 mutations: safety and efficacy in 15 children and adults followed up to 3 years", Arch Ophthalmol., vol. 130, Issue 1, Sep. 12, 2011, pp. 9-24.

Konze et. al., "An orally bioavailable chemical probe of the Lysine Methyltransferases EZH2 and EZH1", ACS Chem Biol., vol. 8, Issue 6, Jun. 21, 2013, pp. 1085-1352.

(56) References Cited

OTHER PUBLICATIONS

Kuzmichev et al., "Histone methyltransferase activity associated with a human multiprotein complex containing the Enhancer of Zeste protein", Genes Dev., 16 (22), pp. 2893-2905.

Léveillard et al., Identification and characterization of rod-derived cone viability factor, Nature Genetics, vol. 36, No. 7, Jul. 2004.

Muller et al., "Histone methyltransferase activity of a *Drosophila* Polycomb group repressor complex", Cell., vol. 111, pp. 197-208.

Plath et al., "Role of histone H3 lysine 27 methylation in X inactivation", Science., vol. 300, Issue 5616, Apr. 4, 2003, pp. 131-135.

Portera-Cailliau et al., "Apoptotic photoreceptor cell death in mouse models of retinitis pigmentosa." PNAS, Neurobiology, vol. 91, Feb. 1994, pp. 974-978.

Potic et al., "An in vitro Model of Human Retinal Detachment Reveals Successive Death Pathway Activations", Front. Neurosci., vol. 14, Article 571293, Nov. 26, 2020, pp. 1-10.

Rao et al., "Dynamic Patterns of Histone Lysine Methylation in the Developing Retina", Investigative Ophthalmology & Visual Science, vol. 51, No. 12, Dec. 2010, pp. 6784-6792.

Rao R C et al, "Histone Lysine Methylation in the Retina", BIOSIS Apr. 2010 (Apr. 2010).

Sahaboglu et al., "Retinitis pigmentosa: rapid neurodegeneration is governed by slow cell death mechanisms", Cell Death Dis. 4, e488, Feb. 7, 2013, pp. 1-8.

Smith et al., "Gene supplementation therapy for recessive forms of inherited retinal dystrophies", Gene Therapy, vol. 19, No. 2, Oct. 27, 2011, pp. 154-161.

Stazi et al., "EZH2 inhibitors: a patent review (2014-2016)" Expert Opin Ther Pat., vol. 27, Issue 7, Apr. 20, 2017, pp. 797-813.

Tanaka et al., "Inhibitors of emerging epigenetic targets for cancer therapy: a patent review (2010-2014)", Pharmaceutical Patent Analyst, vol. 4, No. 4, pp. 261-284.

Anonymous: "Floaters & Spots," American Optometric Association, 2 pages, available at: https://www.aoa.org/healthy-eyes/eye-and-vision-conditions/floaters-and-spots?sso=y (downloaded Aug. 2, 2024).

Anonymous: "Nystagmus," Wikipedia, pp. 1-13, available at https://en.wikipedia.org/wiki/Nystagmus (downloaded, Aug. 2, 2024).

Anonymous: "Ocular allergies", American Optometric Association, 2 pages, available at: https://www.aoa.org/healthy-eyes/eye-and-vision-conditions/ocular-allergies?sso=y (downloaded Aug. 2, 2024).

Anonymous: "Subconjunctival hemorrhage", American Optometric Association, 2 pages, available at: https://www.aoa.org/healthy-eyes/eye-and-vision-conditions/subconjunctival-hemorrhage?sso=y (downloaded Feb. 8, 2024).

Azari, Amir A. et al., "Conjunctivitis: A Systematic Review of Diagnosis and Treatment," National Institute of Health (NIH Public Access), vol. 310, No. 16, p. 1721-1729 (Oct. 23, 2013).

Bronkhorst, IHG et al., "Eye: Inflammation in uveal melanoma," Cambridge Ophthalmological Symposium, vol. 27, p. 217-223 (Dec. 14, 2012).

Dejana, Elisabetta et al., "The molecular basis of endothelial cell plasticity", Nature Communications, No. 14361, 11 pages (Feb. 9, 2017).

Dimaras, Helen et al., "Retinoblastom," Nature Reviews / Disease Primers, vol. 1, p. 1-23 (Aug. 27, 2015).

Duraisamy, Arul et al., "Crosstalk Between Histone and DNA Methylation in Regulation of Retinal Matrix Metalloproteinase-9 in Diabetes", Investigative Ophthalmology and Visual Science, vol. 58(14):6440-6448 (Dec. 1, 2017).

Elisabetta et al., European patent application EP17206417.2, filed Dec. 11, 2017 as priority application of WO2019/115472A1 (Foreign Patent Document 2, above).

European Patent Office, Notice of Opposition issued in European patent application No. EP19734100.1-1109 (European patent No. EP3823671) (Nov. 13, 2024).

Garcia, Ralph et al.: "Optometric Clinical Practice Guideline: Care of the Patient with Learning Related Vision Problems," American Optometric Association, pp. 1-38 (first published Jun. 20, 2000, revised 2008) available at: https://www.aoa.org/AOA/Documents/Practice%20Management/Clinical%20Guidelines/Consensus-based%20guidelines/Care%20of%20Patient%20with%20Learning%20Related%20Vision%20Problems.pdf (downloaded on Aug. 2, 2024).

Khan, Mehnaz et al., "Characterization and Pharmacologic Targeting of EZH2, a Fetal Retinal Protein and Epigenetic Regulator, in Human Retinoblastoma," Lab Invest, vol. 95, No. 11, pp. 1278-1290 (Nov. 2015).

Loh, Ky et al., "Understanding and Preventing Computer Vision Syndrome," Academy of Family Physicians of Malaysia, vol. 3, No. 3, p. 128-130 (2008).

Ola, Mohammed Shamsul et al., "Neurodegeneration and Neuroprotection in Diabetic Retinopathy," International Journal of Molecular Sciences, vol. 14, p. 2559-2572 (Jan. 28, 2013).

Singh, Manni et al., "Uveal Melanoma: A Review of the Literature," Oncol Ther, vol. 6, p. 87-104 (Feb. 6, 2018).

Yang, Zihao et al., "Dyschromatopsia: a comprehensive analysis of mechanisms and cutting-edge treatments for color vision deficiency," Frontiers in Neuroscience, vol. 18, 1265630, 18 pages (Jan. 17, 2024).

* cited by examiner

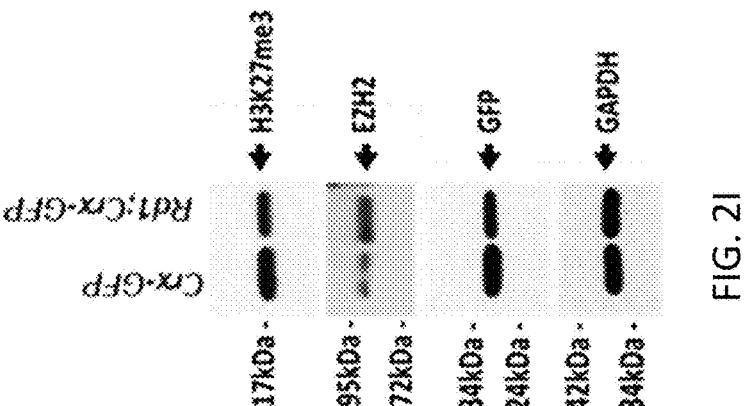
FIG. 2I
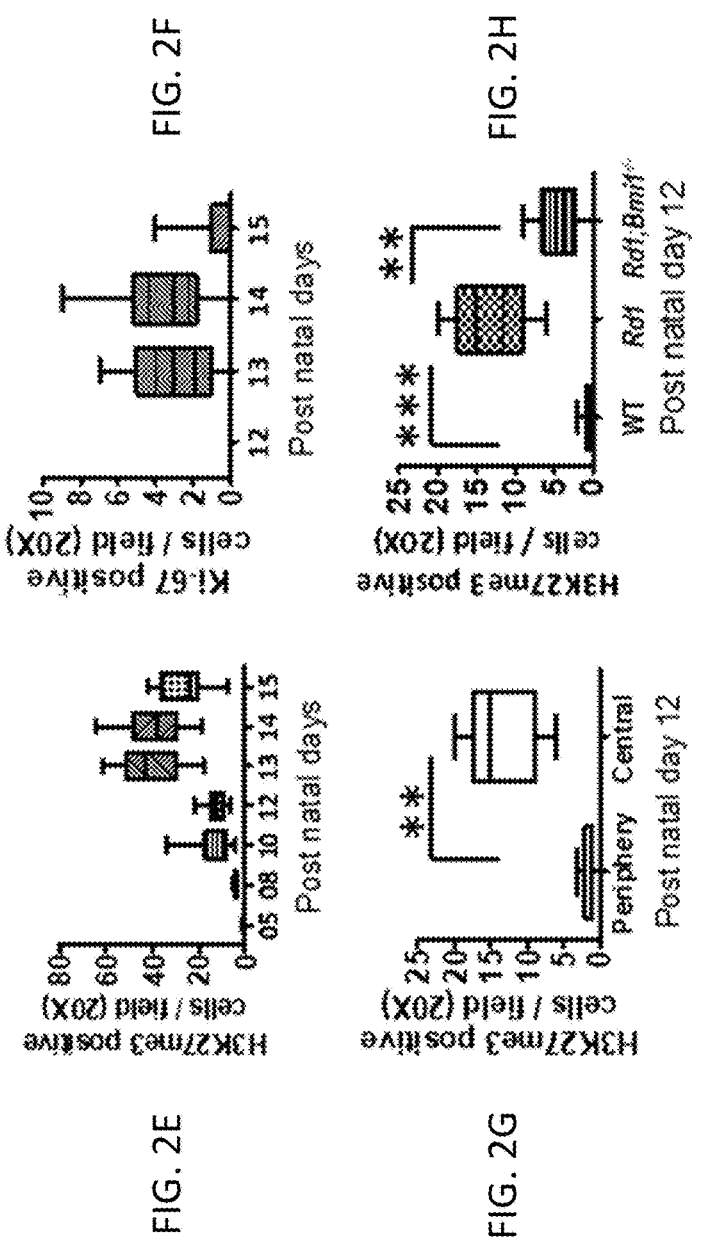
FIG. 2F
FIG. 2H
FIG. 2E
FIG. 2G

FIG. 7A
FIG. 7C
FIG. 7E
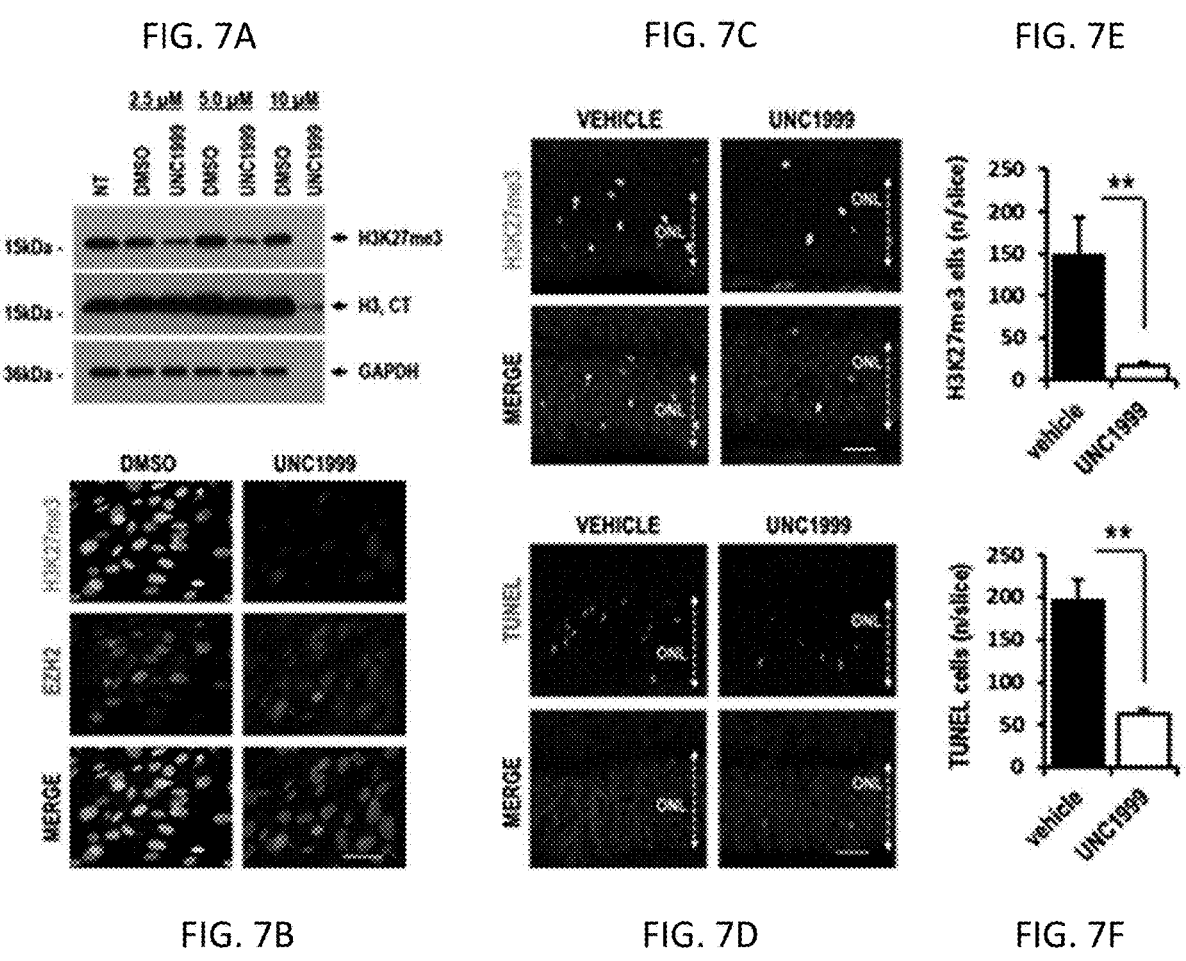
FIG. 7B
FIG. 7D
FIG. 7F
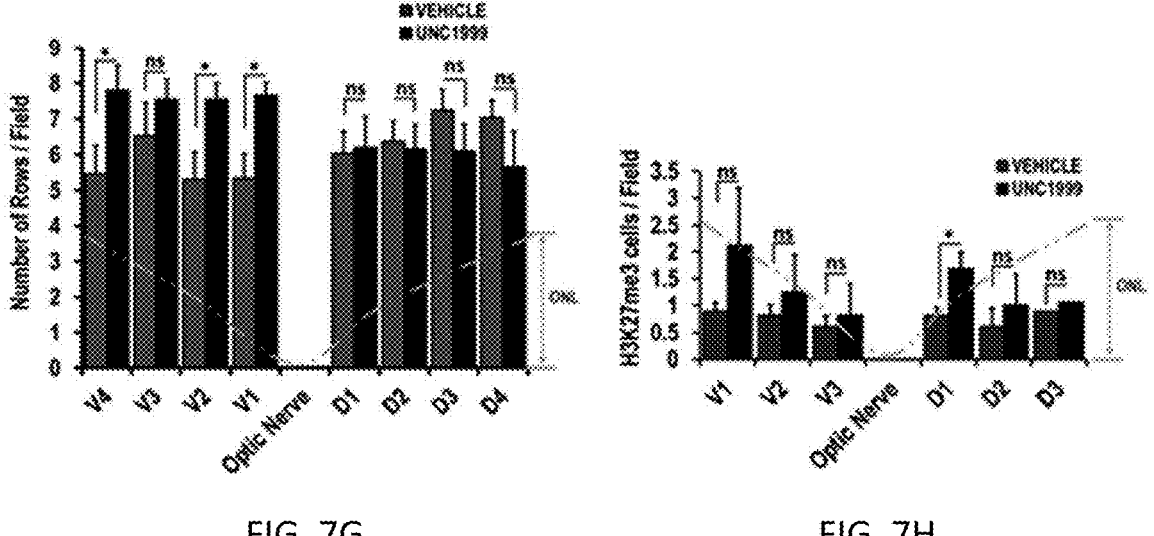
FIG. 7G
FIG. 7H

INHIBITION OF PRC2 SUBUNITS TO TREAT EYE DISORDERS

CROSS REFERENCE TO RELATED APPLICATIONS

This is a continuation of international application no. PCT/EP2019/067784, filed Jul. 2, 2019, which claims priority to European patent application no. EP 18182551.4, filed Jul. 9, 2018 and which applications are incorporated herein by reference in their entireties.

INCORPORATION OF SEQUENCE LISTING

This application contains a Sequence Listing which is submitted herewith
in .txt format. The .txt file contains a sequence listing entitled "3061-101_ST25.txt" created on Mar. 26, 2021 and is 2,463 bytes in size. The sequence listing contained in this .txt file is part of the specification and is hereby incorporated by reference herein in its entirety.

TECHNICAL FIELD OF THE PRESENT DISCLOSURE

This disclosure relates to non-cancer therapeutics and the use of inhibitors of subunits of polycomb repressive complex 2 (PRC2), as well as to inhibitors such as EZH1 inhibitors or EZH2 inhibitors, for the treatment or prevention of eye disorders characterized by degeneration or cell death of retinal neurons, leading progressively to blindness.

BACKGROUND OF THE PRESENT DISCLOSURE

For more than 170,000 patients in Europe having a progressive loss of vision due to genetic defect affecting retina function, no treatments exist for 99% of the cases. The great majority of the patients lose totally sight during the second and third decades. The perception of this handicap by these patients corresponds to quality of life similar to patients affected by terminal cancer or severe stroke (Yuzawa et al., 2013) and thus the expectation for a treatment is great.

Many different mutations are at the origin of inherited retinal dystrophies (IRD) progressively leading to blindness. These mutations mainly affect rod photoreceptor survival. Their death then provokes cone degeneration although the mutation did not directly alter their metabolism. So far, no drugs exist in the market to delay the process of retinal degeneration for inherited retinal dystrophies.

Gene therapy showed recently success (Smith et al., 2012) to restore some visual function in animal models and in a group of patients having one very rare form of Leber congenital amaurosis (LCA2, a deficiency for RPE65) which is a congenital RD. However, two different groups revealed that the gene therapy treatment did not prevent retinal degeneration (Jacobson et al., 2012, Cideciyan et al., 2013). More than 200 hundred genes were identified to be at the origin of RD, which explain 60% of the cases, and only few vectors for gene transfer are now tested in animal models. In addition, preclinical studies with animal models have shown that gene therapy is efficient if provided at the very early stage of the disease (e.g. Bemelmans et al., 2006), but often in real life, the detection of low vision and vision disability occurs when the degenerating process is already well launched. Such clinical phenotype should require a neuroprotective support to allow the maintenance of gene therapy efficacy.

As alternative treatment, the exon skipping is in development and is feasible only for certain genes where the loss of the coding region for one exon is not deleterious for the resulting truncated protein. So far, no drugs are available on the market, but clinical trials for CEP290 will start soon and this approach is promising but necessitates repetitive injection of the drug in the blood circulation. The demonstration that no systemic side effects occur is expected.

A recent clinical trial was launched by GenSight to convert remaining retinal neurons in blind patients to be photosensitive and to potentially restore vision by using optogenetic. No drug is available yet. The light sensitivity of the added protein is very low and necessitates glasses to enhance light stimuli and play with the contrast. Although interesting, this approach has not yet reached the proof of concept in human. In that treatment perspectives, the retinal ganglion cells are targeted and thus the information processing between the photoreceptors and the retinal ganglion cells is absent which will considerably affect the quality of contrast perception, visual acuity and movement perception efficacy. The optogenetic approach is for patients having no more photoreceptors.

A drug treatment for Stargardt disease includes the drug ALK-001 developed by the company Alkeus to reduce the "waste" produced by the retina in this disease is currently tested in clinical trials. This drug targets only this disease which has a prevalence of 1-5/10,000 (Orphanet).

Another alternative treatment includes RdCVF, that was identified (Leveillard et al., 2004) to protect cones against degeneration when rods are dying.

Other approaches aim to reestablish some visual perception in fully blind patients using electronic devices which stimulate directly the remaining retina. This approach had some success (Gekeler et al., 2018) but is dedicated only for a patient population that have lost vision and photoreceptors and thus is an alternative to the optogenetic approach, but not apply to the problem of degeneration or cell death of retinal neurons.

Thus, there is a need for the development of therapeutics that are capable of delaying or arresting degeneration or cell death of retinal neurons. Accordingly, such therapeutics which enables to extend the period of good vision would be useful for the treatment of eye disorders such as retinal degeneration.

BRIEF SUMMARY

The present disclosure is based on the findings that inhibitors of subunits of Polycomb Repressive Complex 2 (PRC2), such as inhibitors of enhancer of zeste homolog 1 (EZH1) or inhibitors of enhancer of zeste homolog 2 (EZH2), have the capability of delaying or arresting degeneration or cell death of retinal neurons. Accordingly, this presents a new area to target in therapies of eye disorders characterized by a progressive loss of vision due to genetic or somatic defects affecting retina function, as inhibitors of subunits of PRC2 (e.g. EZH1 inhibitors or EZH2 inhibitors) can effectively treat eye disorders such as retinal degeneration or neurodegenerative diseases of the retina, that are characterized by degeneration or cell death of retinal neurons.

The inventors identified inhibitors of subunits of PRC2 (e.g. EZH1 inhibitors or EZH2 inhibitors) to be efficient to prolong the survival of retinal neurons (e.g. photoreceptors), in two different mouse models of retinal degeneration, the Rd1 and the Fam161a KO mice, having a rapid and slow degenerative process respectively. Elevated EZH2 activity was also observed in models of dominant forms of RD and in other forms of recessive RD, as well as in two patients affected by retinitis pigmentosa. The inventors therefore consider such inhibitors as being the first efficient therapeutics to significantly prolong photoreceptor survival. In addition, these inhibitors have the advantage that they do not affect process of phototransduction and thus the vision processing.

In Europe 170,000 patients are affected by inherited retinal dystrophies. Among them, the children below 15-year-old should be excluded for EZH2 drug application, knowing that EZH2 is essential for normal retina and brain development. In addition, we can consider that after 40-45 years, all RD patients have lost their photoreceptors. The population between 15 and 45 years is thus representing around 31% of the RD patients. In consequence, around 52700 patients per year may be eligible for EZH2 drug treatment. The patient appreciation of their quality of life is tightly related to their degree of visual acuity loss, the most severe forms leading to an appreciation equivalent to patients with advanced cancer or stroke. The demand of the patients for a treatment is high.

The treatment proposed is a chronic treatment with repetitive intravitreal injections, the frequency remaining to be determined in different models.

They also observed that EZH2 activity is upregulated during a model of human retina detachment when cell death is high, suggesting that EZH2 inhibitors may also target patients with prolonged retina detachment. This population represents around 10,000 patients per year in Europe. One injection during the first healthcare should be sufficient in that case.

Thus, these neuroprotective inhibitors should ensure the prolongation of sight for many patients by protecting retinal neurons such as rod photoreceptors and in consequence their function. In addition, the great majority of the IRD patients have mutations partially affecting the function of rods, leading nonetheless to cell loss, but ensuring image perception and vision. The inhibitors of subunits of PRC2 (e.g. EZH1 inhibitors or EZH2 inhibitors) should significantly prolong vision and autonomy in around 80% of patients affected by retinitis pigmentosa and, in consequence, significantly improve their quality of life.

The Polycomb Repressive Complex 2 (PRC2) is a Polycomb-Group protein (PcG) that is highly evolutionary conserved, that has been found in mammals, insects and plants. PRC2 plays important roles in epigenetic regulation, but also in maintenance and regulation of cellular differentiation and development (Bracken et al., 2006) or X-inactivation (Plath et al., 2003). It acts as a key chromatin modifier by modulating the di- and tri-methylation of lysine 27 on histone H3 (histone H3 lysine 27, H3K27me3), each of which are associated with chromatin transcriptional silencing (Holoch, Margueron, 2017). PRC2 is a dynamic complex that consists of several subunits. H3K27 methylation is catalyzed by the SET domain of enhancer of zeste homolog 2 (EZH2) (Cao et al., 2002) or its functional homologue enhancer of zeste homolog 1 (EZH1), and requires at least the presence of three additional proteins for their enzymatic activity: Embryonic Ectoderm Development (EED), SUppressor of Zeste 12 (SUZ12) and histone binding proteins RetinoBlastoma suppressor (Rb)-Associated protein 46 (RbAp46) or RetinoBlastoma suppressor (rb)-associated protein 48 (RbAp48). EZH2, EED, SUZ12 and RbAp46/

RbAp48 comprise the core subunits of chromatin regulatory PRC2. Other subunits or cofactors such as Adipocyte enhancer-binding protein 2 (AEBP2), PolyComb-Like 1 protein (PCL1), PolyComb-Like 2 protein (PCL2), PolyComb-Like 3 protein (PCL3), Jumonji AT-rich interactive domain 2 (JARID2), EPOP or LCOR associate to PRC2 and modulate its recruitment and activity.

Dysregulation of EZH2 or other PRC2 components such as SUZ12 or EED, and/or H3K27 trimethylation has also been associated with a number of cancers. For instance, aberrant expression of PRC2 and EZH2 has been observed in a broad spectrum of cancers, including breast cancer, myeloma, prostate cancer and lymphoma (Chase et al., 2011, Yoo, et al., 2012). The inhibitors of subunits of PRC2 (e.g. EZH1 inhibitors or EZH2 inhibitors) may also be applicable to other pathologies.

The invention provides first an inhibitor of one or more subunits of polycomb repressive complex 2 (PRC2) for use in the treatment of an eye disorder in a subject in need thereof and more specifically for use in the prevention or the treatment of disorders may be any of cancer, inherited retinal disorder, retinal degeneration, neurodegenerative disease of the retina, ocular autoimmune disease affecting the retina or inflammatory disease affecting the retina, color vision deficiency, computer vision syndrome, diabetic retinopathy, floaters & spots, glaucoma, learning-related vision problems, macular degeneration, nystagmus, ocular allergies, ocular hypertension, retinal detachment, retinitis pigmentosa, subconjunctival hemorrhage, uveitis, leber congenital amaurosis, cone rod dystrophies, night blindness, vitreoretinal dystrophies, erosive vitreoretinopathy, usher syndrome, epiretinal membrane, macular hole, retinitis pigmentosa.

The invention further provides inhibitors of one or more subunits of polycomb repressive complex 2 (PRC2), said subunits being selected from the group consisting of enhancer of zeste homolog 1 (EZH1), enhancer of zeste homolog 2 (EZH2), suppressor of zeste 12 (SUZ12), embryonic ectoderm development (EED), retinoblastoma suppressor (Rb)-Associated protein 46 (RbAp46), retinoblastoma suppressor (rb)-associated protein 48 (RbAp48), adipocyte enhancer-binding protein 2 (AEBP2), polycomb-like 1 protein (PCL1), polycomb-like 2 protein (PCL2), polycomb-like 3 protein (PCL3), jumonji AT-rich interactive domain 2 (JARID2), EPOP, LCOR or their isoforms, paralogs or variants.

The invention still further provides inhibitors of one or more subunits of polycomb repressive complex 2 (PRC2) which comprises a chemical compound which is an epigenetic drug such as an inhibitor of histone modifiers, preferably a histone-lysine methyltransferase inhibitor or a lysine methyltransferase inhibitor such as an inhibitor of H3K27 methylation or an inhibitor of H3K27 trimethylation. The said inhibitors may delay or arrest degeneration or cell death of retinal neurons.

The invention discloses also methods for treating an eye disorder in a subject comprising administering to a subject in need thereof a therapeutically effective amount of one or more inhibitors of a subunit of polycomb repressive complex 2 (PRC2) defined here above.

The invention discloses also methods which further comprise administering to the subject one or more additional therapeutic agents and in particular therapeutic agents that are not inhibitors of a subunit of PRC2.

Further objects of the invention are listed in the attached claims or shall be brought to light throughout the specification and related examples below.

BRIEF DESCRIPTION OF THE FIGURES AND
LEGENDS

FIG. 1: Proposed model of epigenetic-dependent degeneration in Rd1 mice.

Following inherited Pde6$ mutation, inadequate histones modifications occur in response to failure or the gain-of-function of EZH2 and turnover of EZH2 during the fetal stage. Severe perturbation of key biological pathways induces abnormal cell cycle progression and developmental defect. Cells may die prematurely due to failure in maintaining the overall cellular homeostasis.

FIGS. 2A to 2I: Photoreceptors degeneration paralled increased H3K27me3 mark in Rd1 mice.

Figures 2A, 2B:
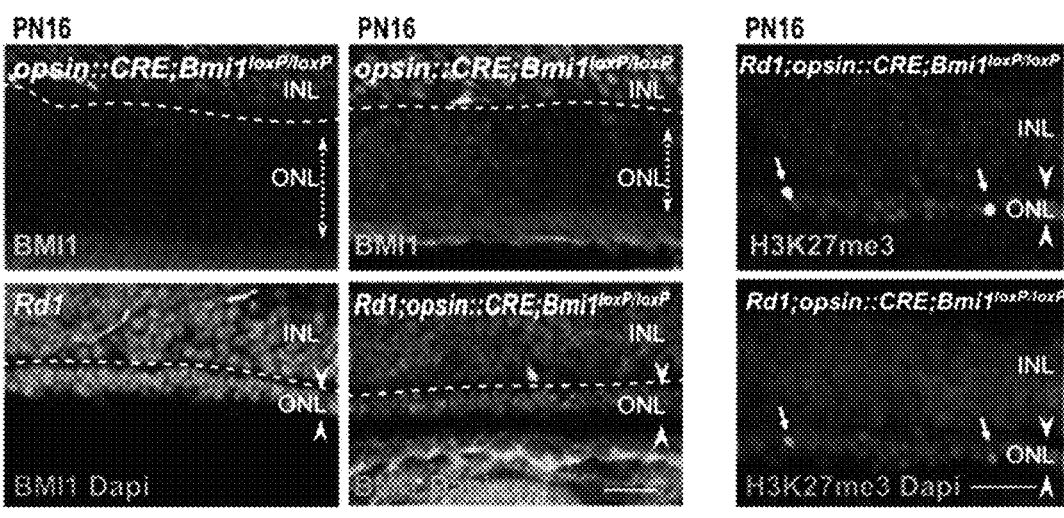
Figure 2C:
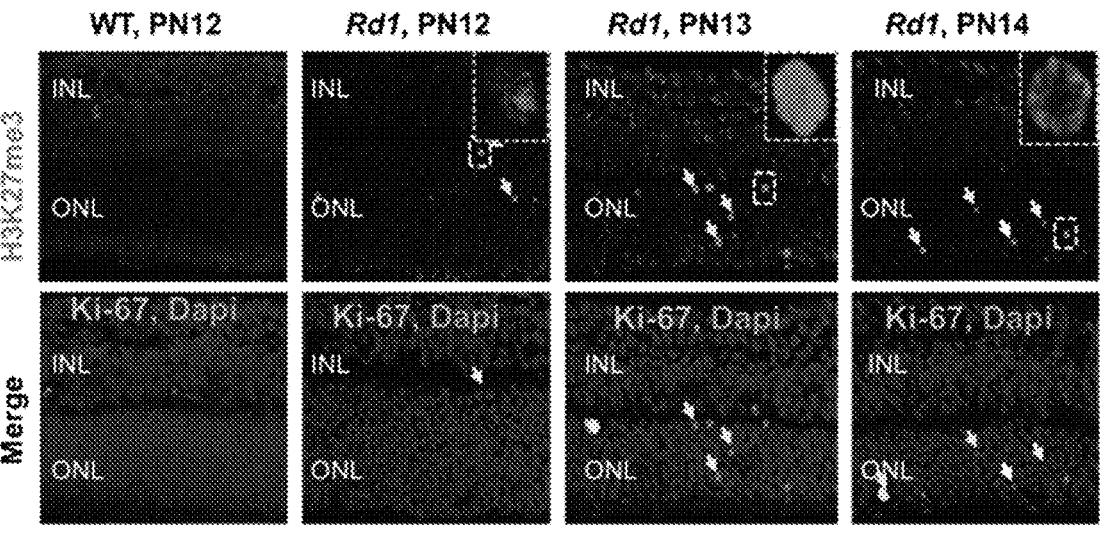
Figure 2D:
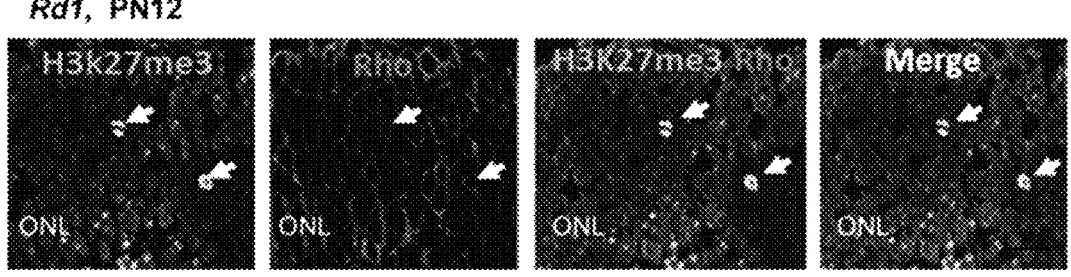

FIG. 2A: Conditional Bmi1 deletion driven by the opsin promoter has no effect on photoreceptor degeneration in Rd1. The Opsin::CRE;Bmi1$^{loxP/lox}$ animal shows a target specific deletion of Bmi1 within the ONL in a mosaic pattern (top). No rescue of photoreceptors was seen in Rd1;Opsin:: CRE;Bmi1$^{loxP/loxP}$ at PN16 compared to the Rd1 mice control (bottom). FIG. 2B: Marked accumulation of the H3k27me3 mark in some degenerating Rd1;Opsin::CRE; Bmi1$^{loxP/loxP}$ photoreceptors at PN15. FIG. 2C: The abundance, distribution (white arrows) and nuclear localization of H3K27me3 cell population are time dependent in Rd1 retina (top, red staining). The expression of the proliferation marker Ki-67 in subset of photoreceptor cells is also shown (bottom panel & FIG. 2F. FIG. 2D: H3K27me3 accumulation occurs in rod cells, as demonstrated by co-localization of H3K27me3 staining with RHODOPSIN (Rho, red labelling, arrows). The number of H3K27me3 positive cells increases with the severity of the disease and reaches the plateau at PN13 in Rd1 mice (FIG. 2E) and was shown to initiate at the central retina (FIG. 2G). FIG. 2H: A marked reduced number of H3K27me3-positive cells in the ONL was observed in the Rd1;Bmi1$^{-/-}$ mouse retina as compared to Rd1. FIG. 2I: Western blot analysis of isolated photoreceptors from the Crx-GFP and Rd1;Crx-GFP retina reveal increased expression of EZH2 in degenerating photoreceptors. Histograms and plots are from average of more than 8 sections, n=4 animals per group. ()=ANOVA t test, p<0.01, (*)=ANOVA t test p<0.001. Error bars indicates SEM. Scale bar: 60 μm for FIGS. 2A-C and 20 μm for FIG. 2D.

Figure 3:
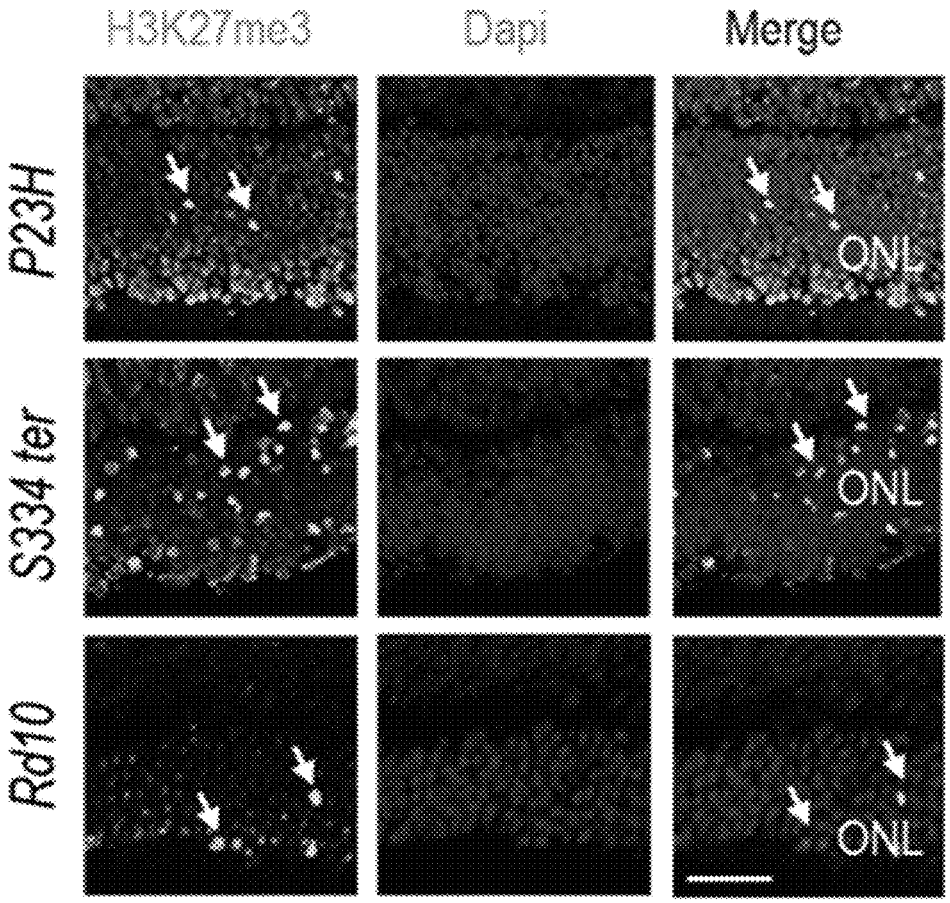

FIG. 3: H3K27me3 detection in other retina degeneration (RD) models.

Retina sections obtained from the RhodopsinP23H mouse at PN12 (top) and the RhodopsinS334-ter at PN15 (middle) rat models of retinal degeneration as well as the Rd10 at PN18 were stained against H3K27me3. High level of the H3K27me3 mark was observed in photoreceptors from all sample analyzed. The Rhodopsin 5334-ter rat shows the more abundant H3k27me3 positive cells in the outer nuclear layer. Scale bars represent 50 μm.

Figure 4:
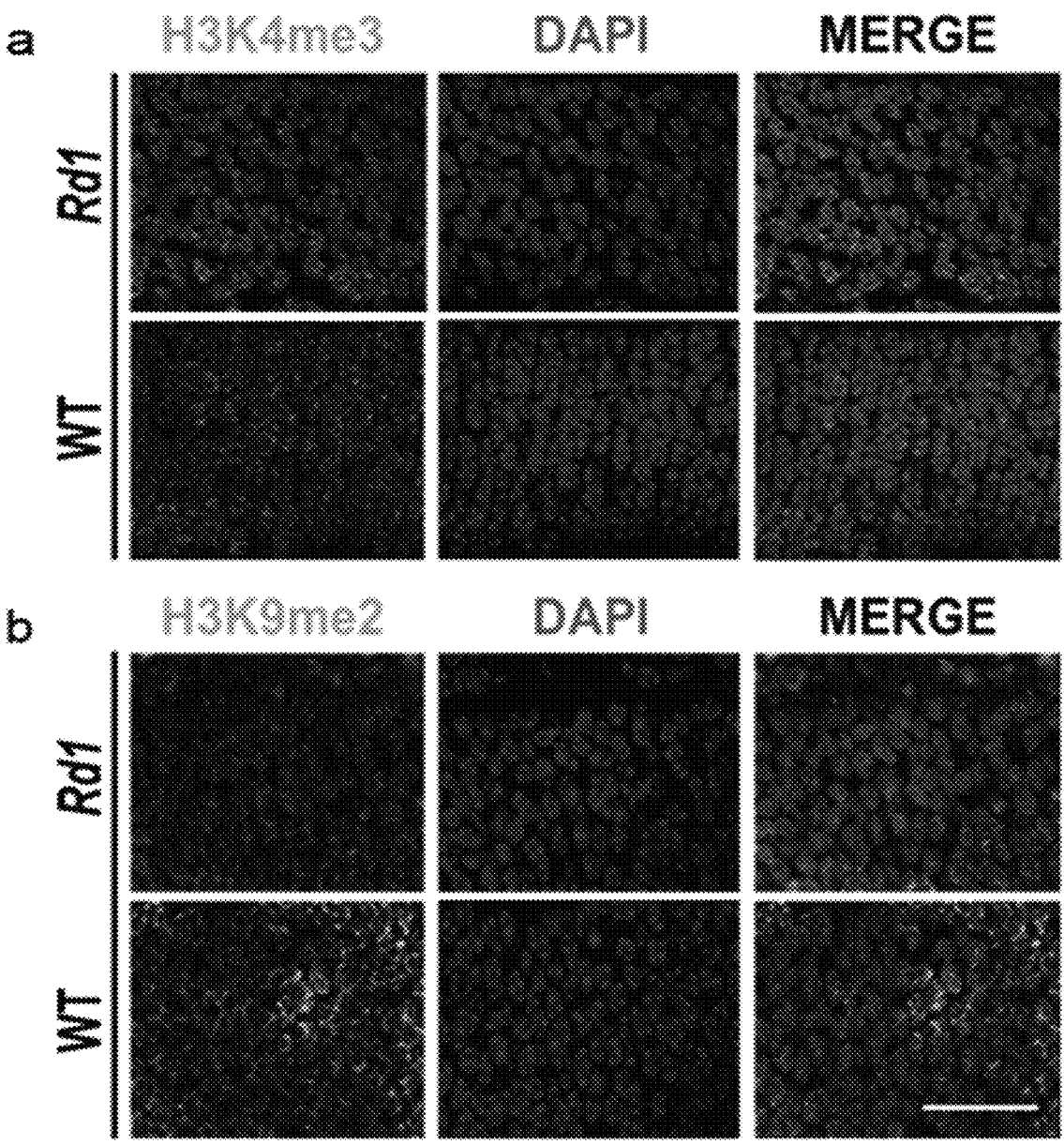

FIG. 4: Homogenous expression and distribution of H3K4me3 and H3K9me2 in WT and Rd1 retinas. The staining was performed on Rd1 and WT retinal sections at PN 12. Confocal analysis did not reveal any obvious changes between WT and Rd1 upon H3K4me3 (top) and H3K9me2 (bottom) staining. Scale bar=20 μm.

Figures 5A, 5B:
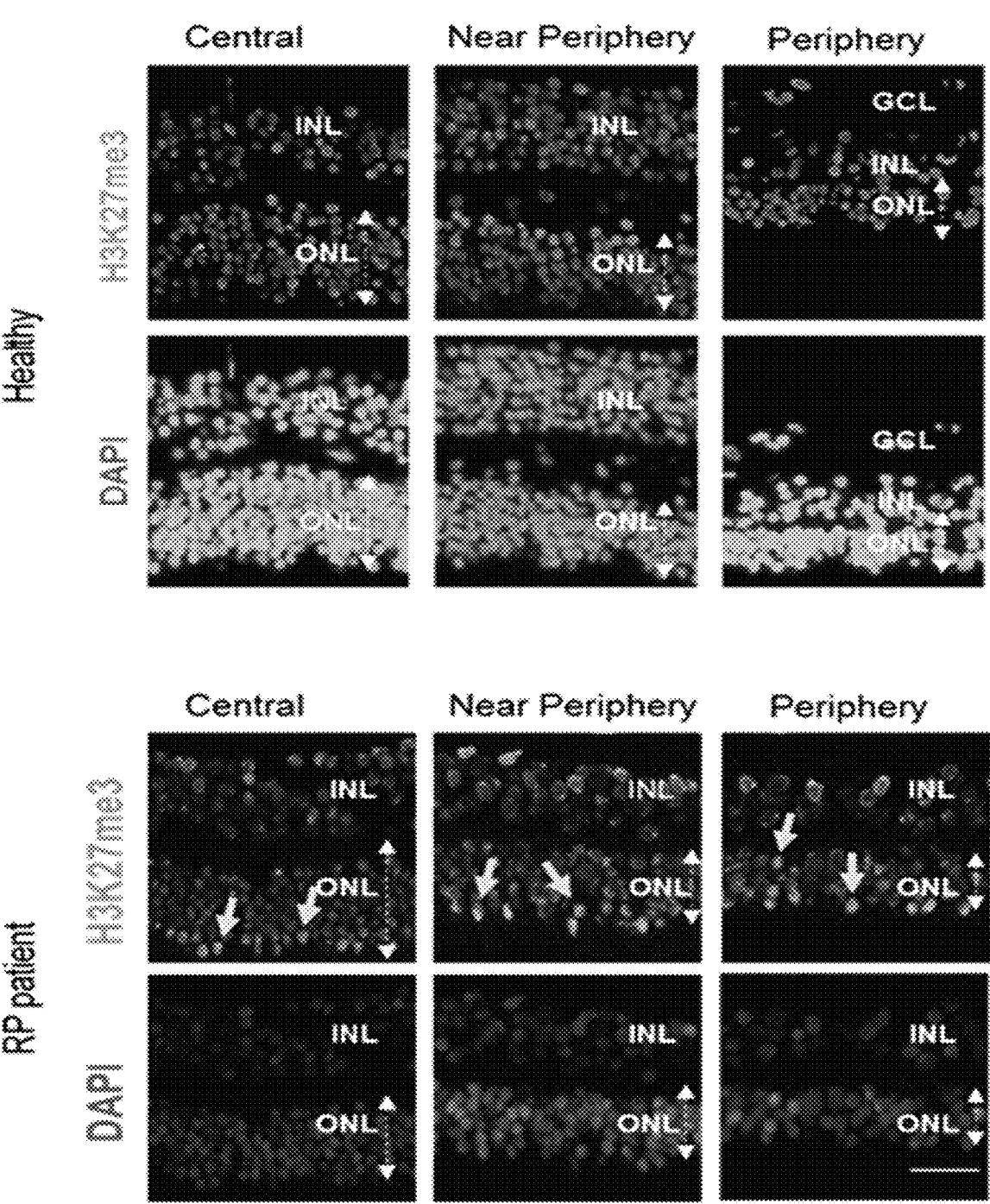

FIGS. 5A and 5B: High level of H3K27me3 mark in human photoreceptors from patient affected by retinitis pigmentosa (RP).

Retina sections from one human healthy donor (FIG. 5A) and one RP patient (FIG. 5B) with moderate degeneration in the central retina and advanced cell loss in the retina peripheral areas. Increased H3K27me3 was much more predominant in areas with advanced retinal degeneration (periphery, arrows). Note that in retina areas with normal photoreceptor architecture, few nuclei also contain the H3K27me3 mark (arrows). Calibration bar: 60 μm and 40 μm respectively for FIG. 5A and FIG. 5B.

FIGS. 6A-6D: H3K27me3 mark increase is an intermediate event between the cGMP accumulation and DNA fragmentation (TUNEL) in Rd1 mice.

Figures 6A, 6B, 6C, 6D:
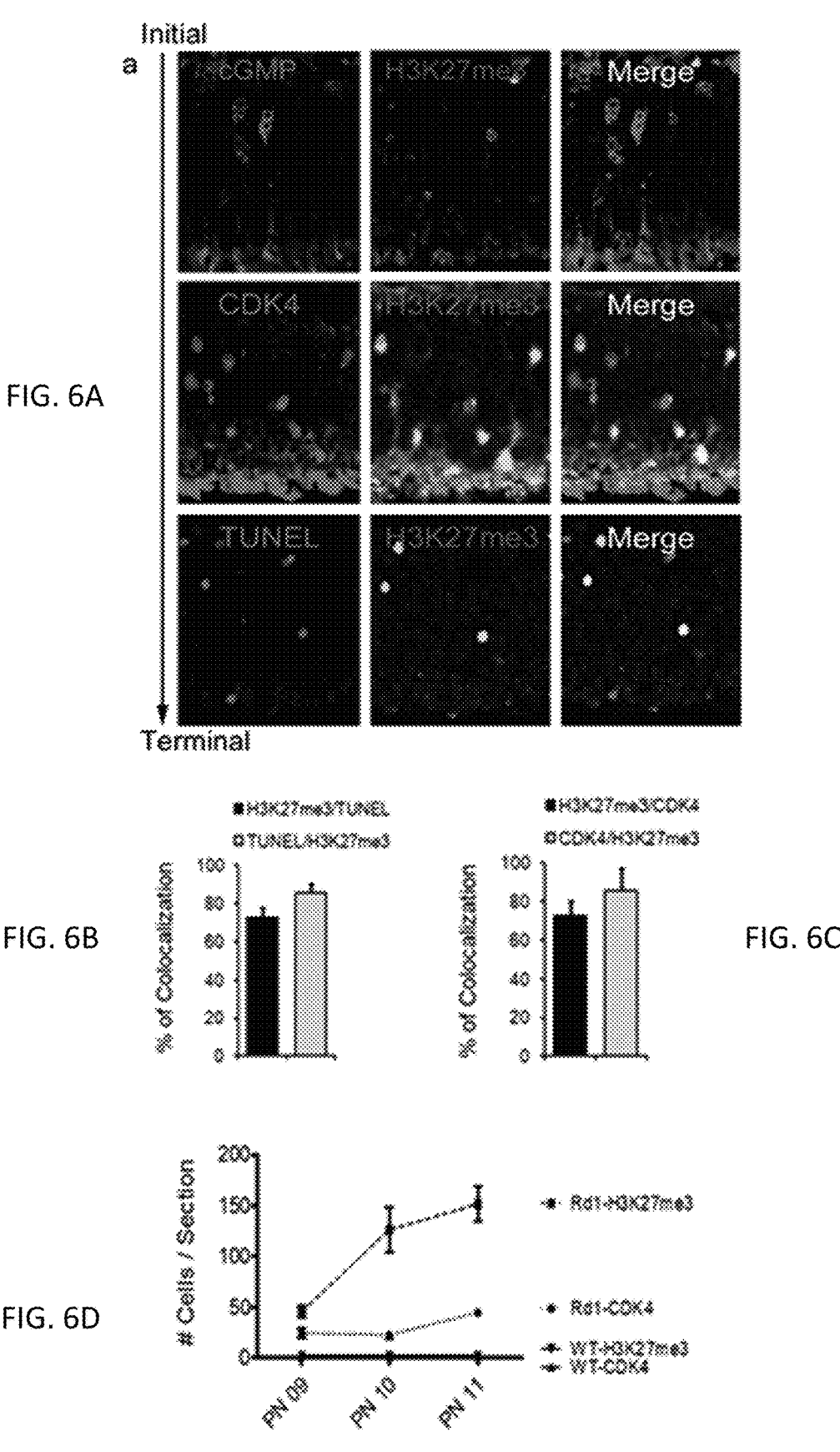

FIG. 6A: Photoreceptors cells in Rd1 retina were double stained with H3K27me3 and either cGMP (top panel), CDK4 (middle panel) or TUNEL (bottom panel) respectively. No co-localization was seen with cGMP and H3K27me3, whereas fractions of CDK4 and TUNEL-positive cells also contained H3K27me3.

FIG. 6B: Bar graph representing the percentage of cells with H3K27me3 and TUNEL or FIG. 6C: CDK4 at 12. Note that less than 40% of the H3K27me3-positive cells are also TUNEL-positive (n=4). Scale bar=20 μm. Error bars indicate SEM. FIG. 6D: Time course analysis of CDK4 and H3K27me3 in Rd1 and WT mice at PN 09, 10 and 11 (n=4 animals per age). The number of H3K27me3-positive cells peaks before CDK4 expression.

FIGS. 7A-7H: Pharmacological inhibition of EZH2 in vivo delays photoreceptor cell death in Rd1 and Fam161a$^{-/-}$ mice.

FIG. 7A: Mouse embryonic fibroblast cells were treated with increasing doses of the EZH2 inhibitor UNC1999 as indicated and 2.5 and 5 μM were shown to be the most effective with less toxicity and leading to a marked reduction of the H3K27me3 mark. FIG. 7B: H3K27me3 immunocytochemistry labelling validated the inhibition of EZH2 by the robust decreased of the mark (clear label). The levels of EZH2 (clear label) were also slightly affected. FIG. 7C-FIG. 7F: Rd1 eyes were injected at PN8 with the vehicle (DMSO) or UNC1999 (2.5 μM final eye concentration). UNC1999 induced a marked reduction of H3K27me3 (FIG. 7C, FIG. 7E) and TUNEL (FIG. 7D, FIG. 7F) positive cells. (FIG. 7G, FIG. 7H) Similar experiment was performed in Fam161$^{-/-}$ mice at repeated doses starting at 2 months of age until their 4th month. Data indicate a statistical significant preservation of photoreceptors rows along the ventral axis of the degenerating retina (FIG. 7G), although no changes were observed for the H3K27me3 mark all over the dorso-ventral axis (FIG. 7H). The analysis was performed 4 days after the last injection. Two-way anova, p<0.05, n=5 retinae analyzed per condition. Calibration bar: 20 μm for B, and 60 μm for C & D.

Figure 8A:
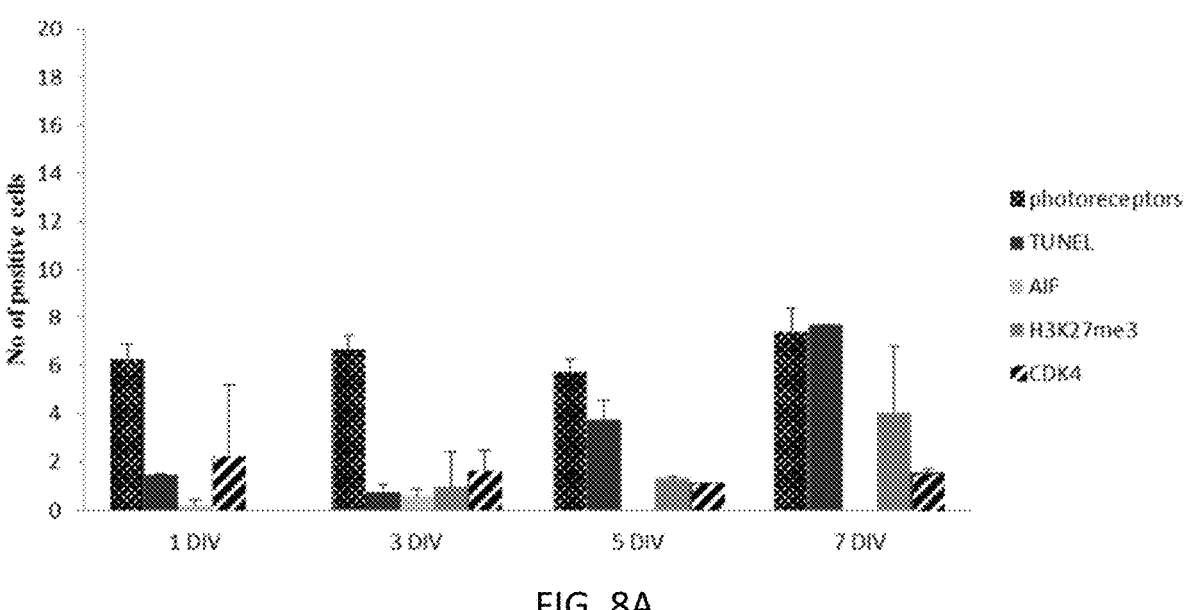
Figure 8B:
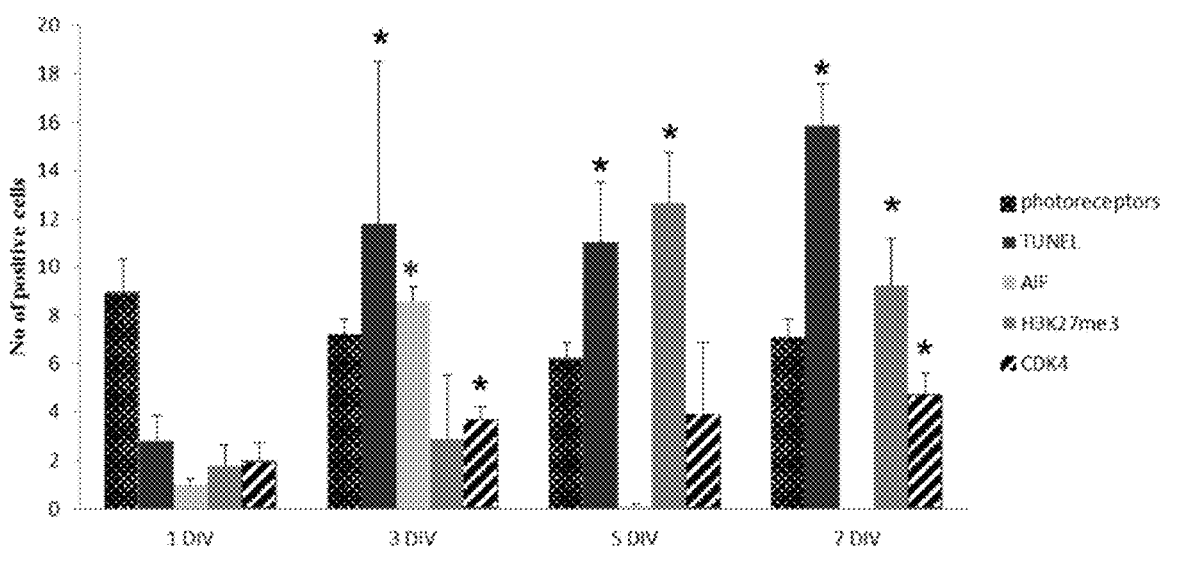

FIGS. 8A and 8B: Pattern of photoreceptor degeneration and cell death pathways in retina explants devoid of RPE.

Figures showing summary data of all four human retinal explants, in two groups: in vitro control group (FIG. 8A) and in vitro RD group (FIG. 8B) for all five followed parameters. Note the significant difference between groups for all five parameters but at different time points. The most important differences are especially for an increase of TUNEL- and H3K27me3-positive photoreceptors over time in the RD group, AIF had a peak at 3DIV, following the peak ofTUNEL positive cells, while the CDK4 is moderately more expressed in RD group, suggesting the cell-cycle re-entrance in certain cells. *: p<0.05 FIG. 9: TUNEL positive cells increased after the absence of RPE cells.

TUNEL positive cells (arrows) at 1DIV, 3 DIV, 5 DIV, 7 DIV, in the human in vitro RD model without RPE and in control group of human in vitro retinal tissue with RPE. The presence of RPE produced an artefact fluorescent background. ONL: outer nuclear layer, INL: inner nuclear layer, RPE: retinal pigment epithelium, Calibration bar: 20 μm.

Figure 10:
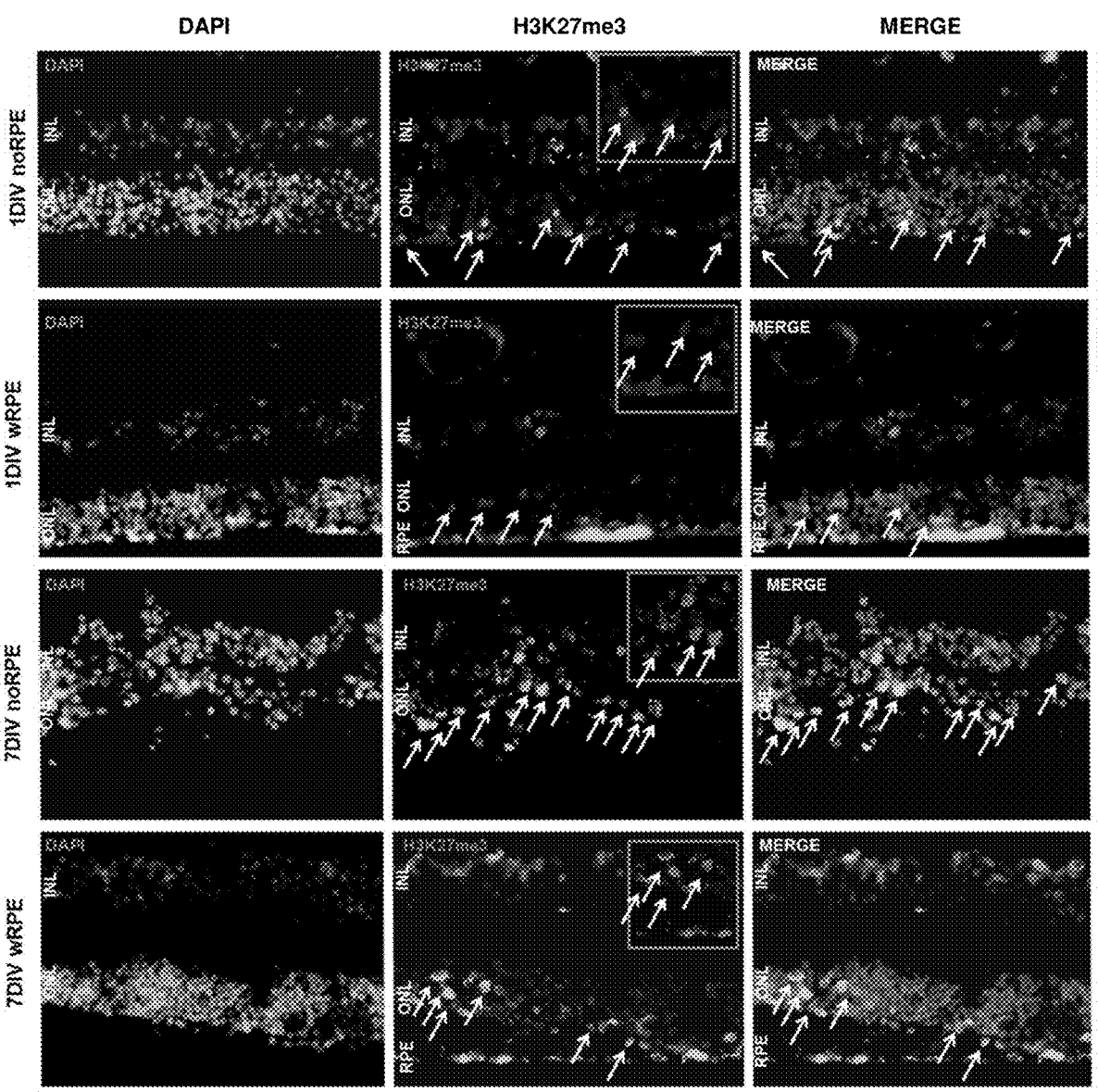

FIG. 10: Increase of the H3K27me3 mark during the mid/late stage of human retina explant degeneration.

H3K27me3 positive cells at 1DIV and at 7DIV, in the human in vitro model of RD (without RPE) and human in vitro model of retinal tissue with RPE ONL: outer nuclear layer, INL: inner nuclear layer, RPE: retinal pigment epithelium. Magnification: 400× Calibration bar: 20 μm.

Figure 11:
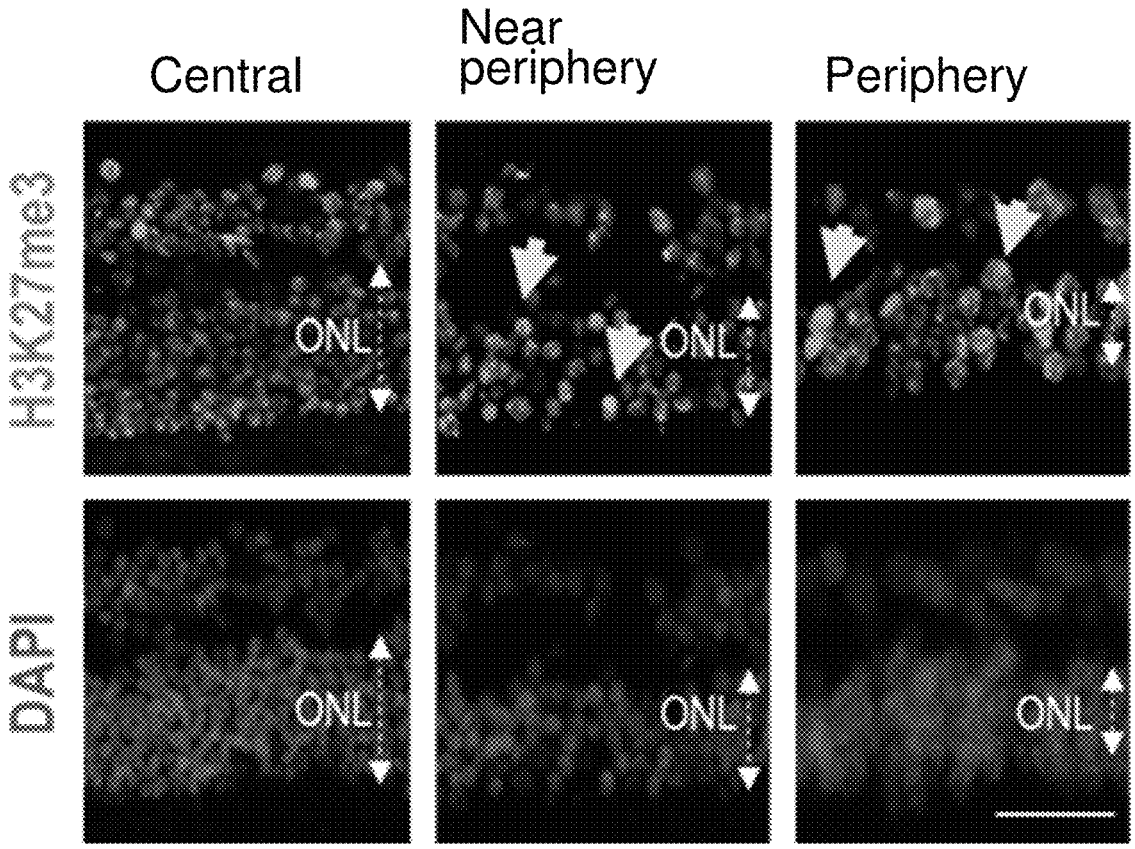

FIG. 11: Retinal detachment induce by tumor formation provokes the increase of the H3K27me3 in the degenerating ONL.

Retina in an eye globe of a patient affected by a melanoma tumor at the periphery of the retina resulting in local retinal detachment. The ONL of the central retina shows a homogenous H3K27me3 labeling, whereas in area where the retina detachment occurred, photoreceptors with highly positive H3K27me3 mark in the nucleus were detected (see arrows). Scale: 20 μm.

Figure 12:
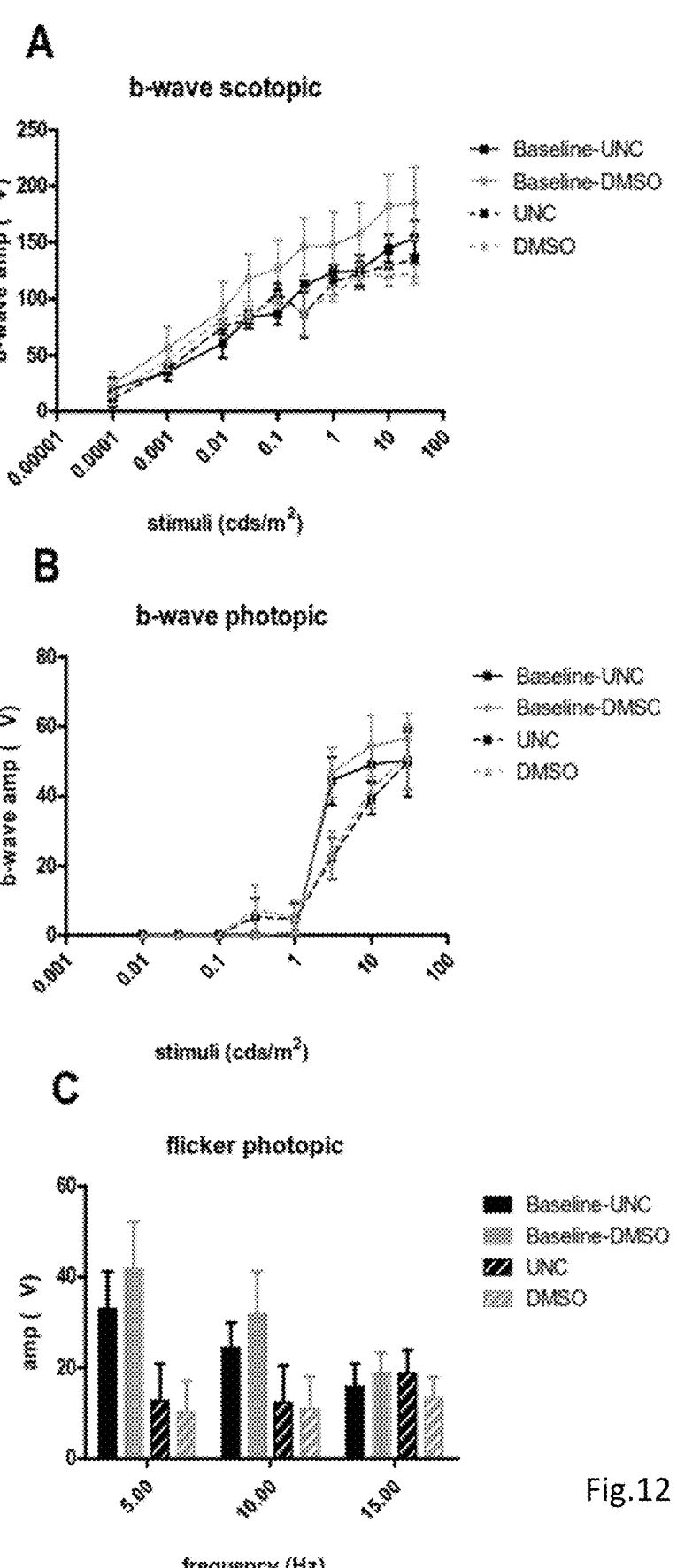

FIG. 12: The injection of UN1999 into the healthy adult eye affects similarly the retina function as the vehicle injection. (A) The retina function was recorded in scotopic conditions before the injection of the drug (black line) or the vehicle (grey line). One week after the injections the same animals of the DMSO group (grey dashed line) and the UNC1999 treated group (black dashed line) were again stimulated with the same range of light stimuli. No differences in retina activity in scotopic condition (maximum b-wave amplitude) were observed between the two groups. A similar analysis was performed in photopic condition (B). Fortwo high stimuli (3 and 10 cda/s.m$^2$), the maximum amplitude of the b-wave was reduced in the two groups in comparison to the baseline. No differences between the two groups were noticed. (C) The two groups of animals were investigated for photopic stimulations with different stimulus frequencies before (full columns) of after the injection (dashed column). A significant reduction was observed for both groups for 5 and 10 Hz stimulations, but not for the 15 Hz suggesting that rods were more affected than cones by the injection procedure. No differences between the control and the treated groups were observed.

DESCRIPTION OF VARIOUS AND PREFERRED EMBODIMENTS

Definitions

The following definitions are collected here to facilitate understanding of certain terms employed frequently herein and are not meant to limit the scope of the present disclosure. For convenience, the abbreviations used herein have their conventional meaning within the biological and chemical arts.

As used herein, the articles "a" and "an" refer to one or to more than one (i.e., to at least one) of the grammatical object of the article. By way of example, "an element" means one element or more than one element, in reference to a list of one or more elements, and should be understood to mean at least one element selected from any one or more of the elements in the said list, but not necessarily including at least one of each and every element specifically listed within said list and not excluding any combinations of elements in said list.

As used herein, the terms "cancer" and "cancerous" refer to or describe the physiological condition in mammals that is typically characterized by unregulated cell growth. Included in this definition are benign and malignant cancers, such as cancers of the eye. Examples of such cancers include melanoma including uveal melanoma and conjunctival melanoma, retinoblastoma, intraocular lymphoma, squamous cell carcinoma, lacrimal gland cancer, eyelid cancer or secondary eye cancer.

As used herein, the term "disorder" is interchangeable with "disease" both of which refer to any condition that would benefit from treatment including, but not limited to, chronic and acute disorders, inherited disorders and non-inherited disorders or disorders including those pathological conditions which predispose the mammal to such disorder. Included in this definition are eye disorders such as inherited retinal disorder, retinal degeneration, neurodegenerative disease of the retina, ocular autoimmune disease affecting the retina or inflammatory disease affecting the retina.

As used herein, the terms "enhancer of zeste homolog 1", EZH1", "EZH1 enzyme", "histone-lysine N-methyltransferase EZH1", "histone-lysine N-methyltransferase EZH1" refer to an enzyme that is encoded by the EZH1 gene. As an illustration of the present definition, the ENSEMBL of human EZH1 gene is ENSG00000108799. Included in this definition are the isoforms, paralogs or variants.

As used herein, the terms "enhancer of zeste homolog 2", "EZH2", "EZH2 enzyme", "histone-lysine N-methyltransferase EZH2", "enhancer of zeste 2 polycomb repressive complex 2 subunit" refer to an enzyme that is encoded by the EZH2 gene. Core catalytic component of the polycomb repressive complex 2 (PRC2), EZH2 is a histone-lysine N-methyltransferase that catalyzes the di- and tri-methylation at of lysine 27 on histone H3 (histone H3 lysine 27, H3K27me3), thereby silencing chromatin transcription. As an illustration of the present definition, the ENSEMBL of human EZH2 gene is ENSG00000106462. Included in this definition are the isoforms, paralogs or variants.

As used herein, the terms "suppressor of zeste 12" and "SUZ12" refer to an enzyme that is encoded by the SUZ12 gene. As an illustration of the present definition, the ENSEMBL of human SUZ12 gene is ENSG00000178691. Included in this definition are the isoforms, paralogs or variants.

As used herein, the terms "embryonic ectoderm development" and "EED" refer to an enzyme that is encoded by the EED gene. Included in this definition are isoforms of EED gene comprising "embryonic ectoderm development 1" or "EED1", "embryonic ectoderm development 2" or "EED2", "embryonic ectoderm development 3" and "EED3" and "embryonic ectoderm development 4" and "EED4". As an illustration of the present definition, the ENSEMBL of human EED gene is ENSG00000074266. Included in this definition are the isoforms, paralogs or variants.

As used herein, the terms "retinoblastoma suppressor (Rb)-Associated protein 46", "RbAp46" and "RBBP7" refer to an enzyme that is encoded by the RBBP7 gene. As an illustration of the present definition, the ENSEMBL of human RBBP7 gene is ENSG00000102054. Included in this definition are the isoforms, paralogs or variants.

As used herein, the terms "retinoblastoma suppressor (rb)-associated protein 48", "RbAp48" and "RBBP4" refer to an enzyme that is encoded by the RBBP4 gene. As an illustration of the present definition, the ENSEMBL of human RBBP4 gene is ENSG00000162521. Included in this definition are the isoforms, paralogs or variants.

As used herein, the terms "adipocyte enhancer-binding protein 2" and "AEBP2" refer to an enzyme that is encoded by the AEBP2 gene. As an illustration of the present definition, the ENSEMBL of human AEBP2 gene is ENSG00000139154. Included in this definition are the isoforms, paralogs or variants.

As used herein, the terms "polycomb-like protein" or "PCL" refer to an enzyme that is a polycomb-like homolog (e.g., PCL1, PCL2 or PCL3). Included in this definition are the isoforms, paralogs or variants.

As used herein, the terms "polycomb-like 1 protein", "PCL1" or "PHF1" refer to an enzyme that is encoded by the PHF1 gene. As an illustration of the present definition, the ENSEMBL of human PHF1 gene is ENSG00000112511. Included in this definition are the isoforms, paralogs or variants. As used herein, the terms "polycomb-like 2 protein", "PCL2" or "MTF2" refer to an enzyme that is encoded by the MTF2 gene. As an illustration of the present definition, the ENSEMBL of human MTF2 gene is ENSG00000143033. Included in this definition are the isoforms, paralogs or variants.

As used herein, the terms polycomb-like 3 protein", "PCL3" or "Phf19" refer to an enzyme that is encoded by the PHF19 gene. As an illustration of the present definition, the ENSEMBL of human PHF19 gene is ENSG00000119403. Included in this definition are the isoforms, paralogs or variants.

As used herein, the terms "jumonji AT-rich interactive domain 2" and "Jarid2" refer to an enzyme that is encoded by the JARID2 gene. As an illustration of the present definition, the ENSEMBL of human JARID2 gene is ENSG00000008083. Included in this definition are the isoforms, paralogs or variants.

As used herein, the terms "EPOP" or "C17orf96" refer to an enzyme that is encoded by the EPOP gene. As an illustration of the present definition, the ENSEMBL of human EPOP gene is ENSG00000273604. Included in this definition are the isoforms, paralogs or variants.

As used herein, the terms "LCOR" or "C10orf12" refer to an enzyme that is encoded by the LCOR gene. As an illustration of the present definition, the ENSEMBL of human LCOR gene is ENSG00000196233. Included in this definition are the isoforms, paralogs or variants.

As used herein, the terms "inhibitor of enhancer of zeste homolog 1", "inhibitor of EZH1", "EZH1 inhibitor", "antagonist of enhancer of zeste homolog 1", "antagonist of EZH1" and "EZH1 antagonist" refer to a molecule capable of binding to EZH1, inhibiting or reducing EZH1 expression levels, or neutralizing, blocking, reducing or interfering with EZH1 biological activities, including, but not limited to, EZH1-mediated methyltransferase activity. For instance, a molecule capable of inhibiting or reducing EZH1 expression levels, or neutralizing, blocking, reducing, or interfering with EZH1 biological activities can exert its effects by binding to one or more EZH1 binding sites on a PRC2 complex (e.g., AEBP2). Included as EZH1 inhibitors that can be used in the methods of the present disclosure are small compounds such as small RNAs complementary to at least a fragment of a nucleic acid molecule encoding an EZH1 polypeptide (e.g., antisense nucleic acid, siRNA, shRNA, miRNA), locked nucleic acids hybridizing to at least a fragment of a nucleic acid molecule encoding an EZH1 polypeptide, peptide nucleic acids binding to at least a fragment of a nucleic acid molecule encoding an EZH1 polypeptide, morpholinos targeting at least a fragment of a nucleic acid molecule encoding an EZH1 polypeptide, inhibitory nucleic acids against EZH1, gapmers or aptamers against EZH1, triple helix molecules against EZH1, ribozymes targeting EZH1, antibodies against EZH1, zinc finger proteins targeting EZH1 (e.g., zinc finger nucleases or zinc finger transcription factors), transcription activator-like effector proteins targeting EZH1 (e.g., transcription activator-like effector nucleases or transcription factors based on transcription activator-like effectors), CRISPR-based systems targeting EZH1 (e.g., systems combining a guide RNA and a catalytically active CRISPR enzyme for cleaving DNA or RNA, systems combining a guide RNA and a catalytically inactive CRISPR enzyme fused or not to a functional domain for gene silencing and epigenetic modifications), meganucleases targeting EZH1, argonaute proteins targeting EZH1 or any polypeptides including chimeric ones that bind to EZH1. Included as EZH1 inhibitors that can be used in the methods of the present disclosure are non-peptide small molecules such as chemical compounds, that are capable of binding to EZH1, inhibiting or reducing EZH1 expression levels, or neutralizing, blocking, reducing or interfering with EZH1 biological activities, including, but not limited to, EZH1-mediated methyltransferase activity. For instance, the EZH1 inhibitors reduces or inhibits, by at least 10%, 20%, 30%, 40%, 50%, 60%, 70%, 80%, 90% or more, the expression level or biological activity of EZH1. Included in this definition are EZH1-specific inhibitors and non-specific inhibitors of EZH1 such as inhibitors of EZH1 isoforms, inhibitors of EZH1 paralogs or inhibitors of EZH1 variants, including, but not limited, to EZH1/EZH2 dual inhibitors or EZH2 inhibitors.

As used herein, the terms "inhibitor of enhancer of zeste homolog 2", "inhibitor of EZH2", "EZH2 inhibitor", "antagonist of enhancer of zeste homolog 2", "antagonist of EZH2" and "EZH2 antagonist" refer to a molecule capable of binding to EZH2, inhibiting or reducing EZH2 expression levels, or neutralizing, blocking, reducing or interfering with EZH2 biological activities, including, but not limited to, EZH2-mediated methyltransferase activity. For instance, a molecule capable of inhibiting or reducing EZH2 expression levels, or neutralizing, blocking, reducing, or interfering with EZH2 biological activities can exert its effects by binding to one or more EZH2 binding sites on a PRC2 complex (e.g., EED, SUZ12). Included as EZH2 inhibitors that can be used in the methods of the present disclosure are small compounds such as small RNAs complementary to at least a fragment of a nucleic acid molecule encoding an EZH2 polypeptide (e.g., antisense nucleic acid, siRNA, shRNA, miRNA), locked nucleic acids hybridizing to at least a fragment of a nucleic acid molecule encoding an EZH2 polypeptide, peptide nucleic acids binding to at least a fragment of a nucleic acid molecule encoding an EZH2 polypeptide, morpholinos targeting at least a fragment of a nucleic acid molecule encoding an EZH2 polypeptide, inhibitory nucleic acids against EZH2, gapmers or aptamers against EZH2, triple helix molecules against EZH2, ribozymes targeting EZH2, antibodies against EZH2, zinc finger proteins targeting EZH2 (e.g., zinc finger nucleases or zinc finger transcription factors), transcription activator-like effector proteins targeting EZH2 (e.g., transcription activator-like effector nucleases or transcription factors based on transcription activator-like effectors), CRISPR-based systems targeting EZH2 (e.g., systems combining a guide RNA and a catalytically active CRISPR enzyme for cleaving DNA or RNA, systems combining a guide RNA and a catalytically inactive CRISPR enzyme fused or not to a functional domain for gene silencing and epigenetic modifications), meganucleases targeting EZH2, argonaute proteins targeting EZH2 or any polypeptides including chimeric ones that bind to EZH2. Included as EZH2 inhibitors that can be used in the methods of the present disclosure are non-peptide small molecules such as chemical compounds, that are capable of binding to EZH2, inhibiting or reducing EZH2 expression levels, or neutralizing, blocking, reducing or interfering with EZH2 biological activities, including, but not limited to, EZH2-mediated methyltransferase activity. For instance, the EZH2 inhibitors reduces or inhibits, by at least 10%, 20%, 30%, 40%, 50%, 60%, 70%, 80%, 90% or more, the expression level or biological activity of EZH2. Included in this definition are EZH2-specific inhibitors and non-specific inhibitors of EZH2 such as inhibitors of EZH2 isoforms, inhibitors of EZH2 paralogs or inhibitors of EZH2 variants, including, but not limited, to EZH1/EZH2 dual inhibitors or EZH1 inhibitors.

As used herein, the terms "inhibitor of suppressor of zeste 12", "inhibitor of SUZ12", "SUZ12 inhibitor", "antagonist of suppressor of zeste 12", "antagonist of SUZ12" and "SUZ12 antagonist" refer to a molecule capable of binding to SUZ12, inhibiting or reducing SUZ12 expression levels, or neutralizing, blocking, reducing or interfering with SUZ12 biological activities, including, but not limited to, methyltransferase activity mediated by the core subunits of PRC2, such as EZH1 or EZH2. For instance, a molecule capable of inhibiting or reducing SUZ12 expression levels, or neutralizing, blocking, reducing, or interfering with SUZ12 biological activities can exert its effects by binding to one or more SUZ12 binding sites on a PRC2 complex (e.g., EZH2, EED). Included as SUZ12 inhibitors that can be used in the methods of the present disclosure are small compounds such as small RNAs complementary to at least a fragment of a nucleic acid molecule encoding an SUZ12 polypeptide (e.g., antisense nucleic acid, siRNA, shRNA, miRNA), locked nucleic acids hybridizing to at least a fragment of a nucleic acid molecule encoding an SUZ12 polypeptide, peptide nucleic acids binding to at least a fragment of a nucleic acid molecule encoding an SUZ12 polypeptide, morpholinos targeting at least a fragment of a nucleic acid molecule encoding an SUZ12 polypeptide, inhibitory nucleic acids against SUZ12, gapmers or aptamers against SUZ12, triple helix molecules against SUZ12, ribozymes targeting SUZ12, antibodies against SUZ12, zinc finger proteins targeting SUZ12 (e.g., zinc finger nucleases or zinc finger transcription factors), transcription activator-like effector proteins targeting SUZ12 (e.g., transcription activator-like effector nucleases or transcription factors based on transcription activator-like effectors), CRISPR-based systems targeting SUZ12 (e.g., systems combining a guide RNA and a catalytically active CRISPR enzyme for cleaving DNA or RNA, systems combining a guide RNA and a catalytically inactive CRISPR enzyme fused or not to a functional domain for gene silencing and epigenetic modifications), meganucleases targeting SUZ12, argonaute proteins targeting SUZ12 or any polypeptides including chimeric ones that bind to SUZ12. Included as SUZ12 inhibitors that can be used in the methods of the present disclosure are non-peptide small molecules such as chemical compounds, that are capable of binding to SUZ12, inhibiting or reducing SUZ12 expression levels, or neutralizing, blocking, reducing or interfering with SUZ12 biological activities, including, but not limited to, methyltransferase activity mediated by the core subunits of PRC2, such as EZH1 or EZH2. For instance, the SUZ12 inhibitors reduces or inhibits, by at least 10%, 20%, 30%, 40%, 50%, 60%, 70%, 80%, 90% or more, the expression level or biological activity of SUZ12. Included in this definition are SUZ12-specific inhibitors and non-specific inhibitors of SUZ12 such as inhibitors of SUZ12 isoforms, inhibitors of SUZ12 paralogs or inhibitors of SUZ12 variants.

As used herein, the terms "inhibitor of embryonic ectoderm development", "inhibitor of EED", "EED inhibitor", "antagonist of embryonic ectoderm development", "antagonist of EED" and "EED antagonist" refer to a molecule capable of binding to EED, inhibiting or reducing EED expression levels, or neutralizing, blocking, reducing or interfering with EED biological activities, including, but not limited to, methyltransferase activity mediated by the core subunits of PRC2, such as EZH1 or EZH2. For instance, a molecule capable of inhibiting or reducing EED expression levels, or neutralizing, blocking, reducing, or interfering with EED biological activities can exert its effects by binding to one or more EED binding sites on a PRC2 complex (e.g., EZH2, SUZ12). Included as EED inhibitors that can be used in the methods of the present disclosure are small compounds such as small RNAs complementary to at least a fragment of a nucleic acid molecule encoding an EED polypeptide (e.g., antisense nucleic acid, siRNA, shRNA, miRNA), locked nucleic acids hybridizing to at least a fragment of a nucleic acid molecule encoding an EED polypeptide, peptide nucleic acids binding to at least a fragment of a nucleic acid molecule encoding an EED polypeptide, morpholinos targeting at least a fragment of a nucleic acid molecule encoding an EED polypeptide, inhibitory nucleic acids against EED, gapmers or aptamers against EED, triple helix molecules against EED, ribozymes targeting EED, antibodies against EED, zinc finger proteins targeting EED (e.g., zinc finger nucleases or zinc finger transcription factors), transcription activator-like effector proteins targeting EED (e.g., transcription activator-like effector nucleases or transcription factors based on transcription activator-like effectors), CRISPR-based systems targeting EED (e.g., systems combining a guide RNA and a catalytically active CRISPR enzyme for cleaving DNA or RNA, systems combining a guide RNA and a catalytically inactive CRISPR enzyme fused or not to a functional domain for gene silencing and epigenetic modifications), meganucleases targeting EED, argonaute proteins targeting EED or any polypeptides including chimeric ones that bind to EED. Included as EED inhibitors that can be used in the methods of the present disclosure are non-peptide small molecules such as chemical compounds, that are capable of binding to EED, inhibiting or reducing EED expression levels, or neutralizing, blocking, reducing or interfering with EED biological activities, including, but not limited to, methyltransferase activity mediated by the core subunits of PRC2, such as EZH1 or EZH2. For instance, the EED inhibitors reduces or inhibits, by at least 10%, 20%, 30%, 40%, 50%, 60%, 70%, 80%, 90% or more, the expression level or biological activity of EED. Included in this definition are EED-specific inhibitors and non-specific inhibitors of EED such as inhibitors of EED isoforms, inhibitors of EED paralogs or inhibitors of EED variants, including, but not limited, to EED1 inhibitors, EED2 inhibitors, EED3 inhibitors, or EED4 inhibitors.

As used herein, the terms "inhibitor of retinoblastoma suppressor (Rb)-Associated protein 46", "inhibitor of RbAp46", "RbAp46 inhibitor", "antagonist of retinoblastoma suppressor (Rb)-Associated protein 46", "antagonist of RbAp46" and "RbAp46 antagonist" refer to a molecule capable of binding to RbAp46, inhibiting or reducing RbAp46 expression levels, or neutralizing, blocking, reducing or interfering with RbAp46 biological activities, including, but not limited to, chromatin assembly and methyltransferase activity mediated by the core subunits of PRC2, such as EZH1 or EZH2. For instance, a molecule capable of inhibiting or reducing RbAp46 expression levels, or neutralizing, blocking, reducing, or interfering with RbAp46 biological activities can exert its effects by binding to one or more RbAp46 binding sites on a PRC2 complex (e.g., SUZ12, PCL). Included as RbAp46 inhibitors that can be used in the methods of the present disclosure are small compounds such as small RNAs complementary to at least a fragment of a nucleic acid molecule encoding an RbAp46 polypeptide (e.g., antisense nucleic acid, siRNA, shRNA, miRNA), locked nucleic acids hybridizing to at least a fragment of a nucleic acid molecule encoding an RbAp46 polypeptide, peptide nucleic acids binding to at least a fragment of a nucleic acid molecule encoding an RbAp46 polypeptide, morpholinos targeting at least a fragment of a nucleic acid molecule encoding an RbAp46 polypeptide, inhibitory nucleic acids against RbAp46, gapmers or aptamers against RbAp46, triple helix molecules against RbAp46, ribozymes targeting RbAp46, antibodies against RbAp46, zinc finger proteins targeting RbAp46 (e.g., zinc finger nucleases or zinc finger transcription factors), transcription activator-like effector proteins targeting RbAp46 (e.g., transcription activator-like effector nucleases or transcription factors based on transcription activator-like effectors), CRISPR-based systems targeting RbAp46 (e.g., systems combining a guide RNA and a catalytically active CRISPR enzyme for cleaving DNA or RNA, systems combining a guide RNA and a catalytically inactive CRISPR enzyme fused or not to a functional domain for gene silencing and epigenetic modifications), meganucleases targeting RbAp46, argonaute proteins targeting RbAp46 or any polypeptides including chimeric ones that bind to RbAp46. Included as RbAp46 inhibitors that can be used in the methods of the present disclosure are non-peptide small molecules such as chemical compounds, that are capable of binding to RbAp46, inhibiting or reducing RbAp46 expression levels, or neutralizing, blocking, reducing or interfering with RbAp46 biological activities, including, but not limited to, chromatin assembly and methyltransferase activity mediated by the core subunits of PRC2, such as EZH1 or EZH2. For instance, the RbAp46 inhibitors reduces or inhibits, by at least 10%, 20%, 30%, 40%, 50%, 60%, 70%, 80%, 90% or more, the expression level or biological activity of RbAp46. Included in this definition are RbAp46-specific inhibitors and non-specific inhibitors of RbAp46 such as inhibitors of RbAp46 isoforms, inhibitors of RbAp46 paralogs or inhibitors of RbAp46 variants, including, but not limited, to RbAp46/RbAp48 dual inhibitors or RbAp48 inhibitors.

As used herein, the terms "inhibitor of retinoblastoma suppressor (rb)-associated protein 48", "inhibitor of RbAp48", "RbAp48 inhibitor", "antagonist of retinoblastoma suppressor (rb)-associated protein 48", "antagonist of RbAp48" and "RbAp48 antagonist" refer to a molecule capable of binding to RbAp48, inhibiting or reducing RbAp48 expression levels, or neutralizing, blocking, reducing or interfering with RbAp48 biological activities, including, but not limited to, chromatin assembly and methyltransferase activity mediated by the core subunits of PRC2, such as EZH1 or EZH2. For instance, a molecule capable of inhibiting or reducing RbAp48 expression levels, or neutralizing, blocking, reducing, or interfering with RbAp48 biological activities can exert its effects by binding to one or more RbAp48 binding sites on a PRC2 complex (e.g., SUZ12, PCL). Included as RbAp48 inhibitors that can be used in the methods of the present disclosure are small compounds such as small RNAs complementary to at least a fragment of a nucleic acid molecule encoding an RbAp48 polypeptide (e.g., antisense nucleic acid, siRNA, shRNA, miRNA), locked nucleic acids hybridizing to at least a fragment of a nucleic acid molecule encoding an RbAp48 polypeptide, peptide nucleic acids binding to at least a fragment of a nucleic acid molecule encoding an RbAp48 polypeptide, morpholinos targeting at least a fragment of a nucleic acid molecule encoding an RbAp48 polypeptide, inhibitory nucleic acids against RbAp48, gapmers or aptamers against RbAp48, triple helix molecules against RbAp48, ribozymes targeting RbAp48, antibodies against RbAp48, zinc finger proteins targeting RbAp48 (e.g., zinc finger nucleases or zinc finger transcription factors), transcription activator-like effector proteins targeting RbAp48 (e.g., transcription activator-like effector nucleases or transcription factors based on transcription activator-like effectors), CRISPR-based systems targeting RbAp48 (e.g., systems combining a guide RNA and a catalytically active CRISPR enzyme for cleaving DNA or RNA, systems combining a guide RNA and a catalytically inactive CRISPR enzyme fused or not to a functional domain for gene silencing and epigenetic modifications), meganucleases targeting RbAp48, argonaute proteins targeting RbAp48 or any polypeptides including chimeric ones that bind to RbAp48. Included as RbAp48 inhibitors that can be used in the methods of the present disclosure are non-peptide small molecules such as chemical compounds, that are capable of binding to RbAp48, inhibiting or reducing RbAp48 expression levels, or neutralizing, blocking, reducing or interfering with RbAp48 biological activities, including, but not limited to, chromatin assembly and methyltransferase activity mediated by the core subunits of PRC2, such as EZH1 or EZH2. For instance, the RbAp48 inhibitors reduces or inhibits, by at least 10%, 20%, 30%, 40%, 50%, 60%, 70%, 80%, 90% or more, the expression level or biological activity of RbAp48. Included in this definition are RbAp48-specific inhibitors and non-specific inhibitors of RbAp48 such as inhibitors of RbAp48 isoforms, inhibitors of RbAp48 paralogs or inhibitors of RbAp48 variants, including, but not limited, to RbAp46/RbAp48 dual inhibitors or RbAp46 inhibitors.

As used herein, the terms "inhibitor of adipocyte enhancer-binding protein 2", "inhibitor of AEBP2", "AEBP2 inhibitor", "antagonist of adipocyte enhancer-binding protein 2", "antagonist of AEBP2" and "AEBP2 antagonist" refer to a molecule capable of binding to AEBP2, inhibiting or reducing AEBP2 expression levels, or neutralizing, blocking, reducing or interfering with AEBP2 biological activities, including, but not limited to, methyltransferase activity mediated by the core subunits of PRC2, such as EZH1 or EZH2. For instance, a molecule capable of inhibiting or reducing AEBP2 expression levels, or neutralizing, blocking, reducing, or interfering with AEBP2 biological activities can exert its effects by binding to one or more AEBP2 binding sites on a PRC2 complex (e.g., JARID2, EED). Included as AEBP2 inhibitors that can be used in the methods of the present disclosure are small compounds such as small RNAs complementary to at least a fragment of a nucleic acid molecule encoding an AEBP2 polypeptide (e.g., antisense nucleic acid, siRNA, shRNA, miRNA), locked nucleic acids hybridizing to at least a fragment of a nucleic acid molecule encoding an AEBP2 polypeptide, peptide nucleic acids binding to at least a fragment of a nucleic acid molecule encoding an AEBP2 polypeptide, morpholinos targeting at least a fragment of a nucleic acid molecule encoding an AEBP2 polypeptide, inhibitory nucleic acids against AEBP2, gapmers or aptamers against AEBP2, triple helix molecules against AEBP2, ribozymes targeting AEBP2, antibodies against AEBP2, zinc finger proteins targeting AEBP2 (e.g., zinc finger nucleases or zinc finger transcription factors), transcription activator-like effector proteins targeting AEBP2 (e.g., transcription activator-like effector nucleases or transcription factors based on transcription activator-like effectors), CRISPR-based systems targeting AEBP2 (e.g., systems combining a guide RNA and a catalytically active CRISPR enzyme for cleaving DNA or RNA, systems combining a guide RNA and a catalytically inactive CRISPR enzyme fused or not to a functional domain for gene silencing and epigenetic modifications), meganucleases targeting AEBP2, argonaute proteins targeting AEBP2 or any polypeptides including chimeric ones that bind to AEBP2. Included as AEBP2 inhibitors that can be used in the methods of the present disclosure are non-peptide small molecules such as chemical compounds, that are capable of binding to AEBP2, inhibiting or reducing AEBP2 expression levels, or neutralizing, blocking, reducing or interfering with AEBP2 biological activities, including, but not limited to, methyltransferase activity mediated by the core subunits of PRC2, such as EZH1 or EZH2. For instance, the AEBP2 inhibitors reduces or inhibits, by at least 10%, 20%, 30%, 40%, 50%, 60%, 70%, 80%, 90% or more, the expression level or biological activity of AEBP2. Included in this definition are AEBP2-specific inhibitors and non-specific inhibitors of AEBP2 such as inhibitors of AEBP2 isoforms, inhibitors of AEBP2 paralogs or inhibitors of AEBP2 variants.

As used herein, the terms "inhibitor of jumonji AT-rich interactive domain 2", "inhibitor of JARID2", "JARID2 inhibitor", "antagonist of jumonji AT-rich interactive domain 2", "antagonist of JARID2" and "JARID2 antagonist" refer to a molecule capable of binding to JARID2, inhibiting or reducing JARID2 expression levels, or neutralizing, blocking, reducing or interfering with JARID2 biological activities, including, but not limited to, methyltransferase activity mediated by the core subunits of PRC2, such as EZH1 or EZH2. For instance, a molecule capable of inhibiting or reducing JARID2 expression levels, or neutralizing, blocking, reducing, or interfering with JARID2 biological activities can exert its effects by binding to one or more JARID2 binding sites on a PRC2 complex (e.g., EED, AEBP2). Included as JARID2 inhibitors that can be used in the methods of the present disclosure are small compounds such as small RNAs complementary to at least a fragment of a nucleic acid molecule encoding an JARID2 polypeptide (e.g., antisense nucleic acid, siRNA, shRNA, miRNA), locked nucleic acids hybridizing to at least a fragment of a nucleic acid molecule encoding an JARID2 polypeptide, peptide nucleic acids binding to at least a fragment of a nucleic acid molecule encoding an JARID2 polypeptide, morpholinos targeting at least a fragment of a nucleic acid molecule encoding an JARID2 polypeptide, inhibitory nucleic acids against JARID2, gapmers or aptamers against JARID2, triple helix molecules against JARID2, ribozymes targeting JARID2, antibodies against JARID2, zinc finger proteins targeting JARID2 (e.g., zinc finger nucleases or zinc finger transcription factors), transcription activator-like effector proteins targeting JARID2 (e.g., transcription activator-like effector nucleases or transcription factors based on transcription activator-like effectors), CRISPR-based systems targeting JARID2 (e.g., systems combining a guide RNA and a catalytically active CRISPR enzyme for cleaving DNA or RNA, systems combining a guide RNA and a catalytically inactive CRISPR enzyme fused or not to a functional domain for gene silencing and epigenetic modifications), meganucleases targeting JARID2, argonaute proteins targeting JARID2 or any polypeptides including chimeric ones that bind to JARID2. Included as JARID2 inhibitors that can be used in the methods of the present disclosure are non-peptide small molecules such as chemical compounds, that are capable of binding to JARID2, inhibiting or reducing JARID2 expression levels, or neutralizing, blocking, reducing or interfering with JARID2 biological activities, including, but not limited to, methyltransferase activity mediated by the core subunits of PRC2, such as EZH1 or EZH2. For instance, the JARID2 inhibitors reduces or inhibits, by at least 10%, 20%, 30%, 40%, 50%, 60%, 70%, 80%, 90% or more, the expression level or biological activity of JARID2. Included in this definition are JARID2-specific inhibitors and non-specific inhibitors of JARID2 such as inhibitors of JARID2 isoforms, inhibitors of JARID2 paralogs or inhibitors of JARID2 variants, including, but not limited, to KDM5B inhibitors.

As used herein, the terms "inhibitor of polycomb-like protein", "inhibitor of PCL", "PCL inhibitor", "antagonist of polycomb-like protein", "antagonist of PCL" and "PCL antagonist" refer to a molecule capable of binding to one or more PCL, inhibiting or reducing one or more PCL expression levels, or neutralizing, blocking, reducing or interfering with one or more PCL biological activities, including, but not limited to, methyltransferase activity mediated by the core subunits of PRC2, such as EZH1 or EZH2. For instance, a molecule capable of inhibiting or reducing one or more PCL expression levels, or neutralizing, blocking, reducing, or interfering with one or more PCL biological activities can exert its effects by binding to one or more PCL binding sites on a PRC2 complex (e.g., AEBP2, RbAp46, RbAp48). Included as PCL inhibitors that can be used in the methods of the present disclosure are small compounds such as small RNAs complementary to at least a fragment of a nucleic acid molecule encoding an PCL polypeptide (e.g., antisense nucleic acid, siRNA, shRNA, miRNA), locked nucleic acids hybridizing to at least a fragment of a nucleic acid molecule encoding an PCL polypeptide, peptide nucleic acids binding to at least a fragment of a nucleic acid molecule encoding an PCL polypeptide, morpholinos targeting at least a fragment of a nucleic acid molecule encoding an PCL polypeptide, inhibitory nucleic acids against PCL, gapmers or aptamers against PCL, triple helix molecules against PCL, ribozymes targeting PCL, antibodies against PCL, zinc finger proteins targeting PCL (e.g., zinc finger nucleases or zinc finger transcription factors), transcription activator-like effector proteins targeting PCL (e.g., transcription activator-like effector nucleases or transcription factors based on transcription activator-like effectors), CRISPR-based systems targeting PCL (e.g., systems combining a guide RNA and a catalytically active CRISPR enzyme for cleaving DNA or RNA, systems combining a guide RNA and a catalytically inactive CRISPR enzyme fused or not to a functional domain for gene silencing and epigenetic modifications), meganucleases targeting PCL, argonaute proteins targeting PCL or any polypeptides including chimeric ones that bind to at least one PCL. Included as PCL inhibitors that can be used in the methods of the present disclosure are non-peptide small molecules such as chemical compounds, that are capable of binding to one or more PCL, inhibiting or reducing one or more PCL expression levels, or neutralizing, blocking, reducing or interfering with one or more PCL biological activities, including, but not limited to, methyltransferase activity mediated by the core subunits of PRC2, such as EZH1 or EZH2. For instance, the PCL inhibitors reduces or inhibits, by at least 10%, 20%, 30%, 40%, 50%, 60%, 70%, 80%, 90% or more, the expression level or biological activity of one or more PCL. Included in this definition are PCL-specific inhibitors and non-specific inhibitors of PCL such as inhibitors of PCL isoforms, inhibitors of PCL paralogs or inhibitors of PCL variants.

As used herein, the terms "inhibitor of polycomb-like 1 protein", "inhibitor of PCL1", "PCL1 inhibitor", "inhibitor of PHF1", "PHF1 inhibitor", "antagonist of polycomb-like 1 protein", "antagonist of PCL1", "PCL1 antagonist", "antagonist of PHF1" and "PHF1 antagonist" refer to a molecule capable of binding to PCL1, inhibiting or reducing PCL1 expression levels, or neutralizing, blocking, reducing or interfering with PCL1 biological activities, including, but not limited to, DNA damage response and methyltransferase activity mediated by the core subunits of PRC2, such as EZH1 or EZH2. For instance, a molecule capable of inhibiting or reducing PCL1 expression levels, or neutralizing, blocking, reducing, or interfering with PCL1 biological activities can exert its effects by binding to one or more PCL1 binding sites on a PRC2 complex (e.g., AEBP2, RbAp46, RbAp48). Included as PCL1 inhibitors that can be used in the methods of the present disclosure are small compounds such as small RNAs complementary to at least a fragment of a nucleic acid molecule encoding an PCL1 polypeptide (e.g., antisense nucleic acid, siRNA, shRNA, miRNA), locked nucleic acids hybridizing to at least a fragment of a nucleic acid molecule encoding an PCL1 polypeptide, peptide nucleic acids binding to at least a fragment of a nucleic acid molecule encoding an PCL1 polypeptide, morpholinos targeting at least a fragment of a nucleic acid molecule encoding an PCL1 polypeptide, inhibitory nucleic acids against PCL1, gapmers or aptamers against PCL1, triple helix molecules against PCL1, ribozymes targeting PCL1, antibodies against PCL1, zinc finger proteins targeting PCL1 (e.g., zinc finger nucleases or zinc finger transcription factors), transcription activator-like effector proteins targeting PCL1 (e.g., transcription activator-like effector nucleases or transcription factors based on transcription activator-like effectors), CRISPR-based systems targeting PCL1 (e.g., systems combining a guide RNA and a catalytically active CRISPR enzyme for cleaving DNA or RNA, systems combining a guide RNA and a catalytically inactive CRISPR enzyme fused or not to a functional domain for gene silencing and epigenetic modifications), meganucleases targeting PCL1, argonaute proteins targeting PCL1 or any polypeptides including chimeric ones that bind to PCL1. Included as PCL1 inhibitors that can be used in the methods of the present disclosure are non-peptide small molecules such as chemical compounds, that are capable of binding to PCL1, inhibiting or reducing PCL1 expression levels, or neutralizing, blocking, reducing or interfering with PCL1 biological activities, including, but not limited to, DNA damage response and methyltransferase activity mediated by the core subunits of PRC2, such as EZH1 or EZH2. For instance, the PCL1 inhibitors reduces or inhibits, by at least 10%, 20%, 30%, 40%, 50%, 60%, 70%, 80%, 90% or more, the expression level or biological activity of PCL1. Included in this definition are PCL1-specific inhibitors and non-specific inhibitors of PCL1 such as inhibitors of PCL1 isoforms, inhibitors of PCL1 paralogs or inhibitors of PCL1 variants, including, but not limited, to PCL2 inhibitors and PCL3 inhibitors.

As used herein, the terms "inhibitor of polycomb-like 2 protein", "inhibitor of PCL2", "PCL2 inhibitor", "inhibitor of MTF2", "MTF2 inhibitor", "antagonist of polycomb-like 2 protein", "antagonist of PCL2", "PCL2 antagonist", "antagonist of MTF2" and "MTF2 antagonist" refer to a molecule capable of binding to PCL2, inhibiting or reducing PCL2 expression levels, or neutralizing, blocking, reducing or interfering with PCL2 biological activities, including, but not limited to, methyltransferase activity mediated by the core subunits of PRC2, such as EZH1 or EZH2. For instance, a molecule capable of inhibiting or reducing PCL2 expression levels, or neutralizing, blocking, reducing, or interfering with PCL2 biological activities can exert its effects by binding to one or more PCL2 binding sites on a PRC2 complex (e.g., AEBP2, RbAp46, RbAp48). Included as PCL2 inhibitors that can be used in the methods of the present disclosure are small compounds such as small RNAs complementary to at least a fragment of a nucleic acid molecule encoding an PCL2 polypeptide (e.g., antisense nucleic acid, siRNA, shRNA, miRNA), locked nucleic acids hybridizing to at least a fragment of a nucleic acid molecule encoding an PCL2 polypeptide, peptide nucleic acids binding to at least a fragment of a nucleic acid molecule encoding an PCL2 polypeptide, morpholinos targeting at least a fragment of a nucleic acid molecule encoding an PCL2 polypeptide, inhibitory nucleic acids against PCL2, gapmers or aptamers against PCL2, triple helix molecules against PCL2, ribozymes targeting PCL2, antibodies against PCL2, zinc finger proteins targeting PCL2 (e.g., zinc finger nucleases or zinc finger transcription factors), transcription activator-like effector proteins targeting PCL2 (e.g., transcription activator-like effector nucleases or transcription factors based on transcription activator-like effectors), CRISPR-based systems targeting PCL2 (e.g., systems combining a guide RNA and a catalytically active CRISPR enzyme for cleaving DNA or RNA, systems combining a guide RNA and a catalytically inactive CRISPR enzyme fused or not to a functional domain for gene silencing and epigenetic modifications), meganucleases targeting PCL2, argonaute proteins targeting PCL2 or any polypeptides including chimeric ones that bind to PCL2. Included as PCL2 inhibitors that can be used in the methods of the present disclosure are non-peptide small molecules such as chemical compounds, that are capable of binding to PCL2, inhibiting or reducing PCL2 expression levels, or neutralizing, blocking, reducing or interfering with PCL2 biological activities, including, but not limited to, methyltransferase activity mediated by the core subunits of PRC2, such as EZH1 or EZH2. For instance, the PCL2 inhibitors reduces or inhibits, by at least 10%, 20%, 30%, 40%, 50%, 60%, 70%, 80%, 90% or more, the expression level or biological activity of PCL2. Included in this definition are PCL2-specific inhibitors and non-specific inhibitors of PCL2 such as inhibitors of PCL2 isoforms, inhibitors of PCL2 paralogs or inhibitors of PCL2 variants, including, but not limited, to PCL1 inhibitors and PCL3 inhibitors.

As used herein, the terms "inhibitor of polycomb-like 3 protein", "inhibitor of PCL3", "PCL3 inhibitor", "inhibitor of Phf19", "Phf19 inhibitor", "antagonist of polycomb-like 3 protein", "antagonist of PCL3", "PCL3 antagonist", "antagonist of Phf19" and "Phf19 antagonist" refer to a molecule capable of binding to PCL3, inhibiting or reducing PCL3 expression levels, or neutralizing, blocking, reducing or interfering with PCL3 biological activities, including, but not limited to, methyltransferase activity mediated by the core subunits of PRC2, such as EZH1 or EZH2. For instance, a molecule capable of inhibiting or reducing PCL3 expression levels, or neutralizing, blocking, reducing, or interfering with PCL3 biological activities can exert its effects by binding to one or more PCL3 binding sites on a PRC2 complex (e.g., AEBP2, RbAp46, RbAp48). Included as PCL3 inhibitors that can be used in the methods of the present disclosure are small compounds such as small RNAs complementary to at least a fragment of a nucleic acid molecule encoding an PCL3 polypeptide (e.g., antisense nucleic acid, siRNA, shRNA, miRNA), locked nucleic acids hybridizing to at least a fragment of a nucleic acid molecule encoding an PCL3 polypeptide, peptide nucleic acids binding to at least a fragment of a nucleic acid molecule encoding an PCL3 polypeptide, morpholinos targeting at least a fragment of a nucleic acid molecule encoding an PCL3 polypeptide, inhibitory nucleic acids against PCL3, gapmers or aptamers against PCL3, triple helix molecules against PCL3, ribozymes targeting PCL3, antibodies against PCL3, zinc finger proteins targeting PCL3 (e.g., zinc finger nucleases or zinc finger transcription factors), transcription activator-like effector proteins targeting PCL3 (e.g., transcription activator-like effector nucleases or transcription factors based on transcription activator-like effectors), CRISPR-based systems targeting PCL3 (e.g., systems combining a guide RNA and a catalytically active CRISPR enzyme for cleaving DNA or RNA, systems combining a guide RNA and a catalytically inactive CRISPR enzyme fused or not to a functional domain for gene silencing and epigenetic modifications), meganucleases targeting PCL3, argonaute proteins targeting PCL3 or any polypeptides including chimeric ones that bind to PCL3. Included as PCL3 inhibitors that can be used in the methods of the present disclosure are non-peptide small molecules such as chemical compounds, that are capable of binding to PCL3, inhibiting or reducing PCL3 expression levels, or neutralizing, blocking, reducing or interfering with PCL3 biological activities, including, but not limited to, methyltransferase activity mediated by the core subunits of PRC2, such as EZH1 or EZH2. For instance, the PCL3 inhibitors reduces or inhibits, by at least 10%, 20%, 30%, 40%, 50%, 60%, 70%, 80%, 90% or more, the expression level or biological activity of PCL3. Included in this definition are PCL3-specific inhibitors and non-specific inhibitors of PCL3 such as inhibitors of PCL3 isoforms, inhibitors of PCL3 paralogs or inhibitors of PCL3 variants, including, but not limited, to isoform 1 inhibitors, isoform 2 inhibitors, PCL1 inhibitors and PCL2 inhibitors.

As used herein, the terms "inhibitor of EPOP", "EPOP inhibitor", "inhibitor of C17orf96", "C17orf96 inhibitor", "antagonist of EPOP" and "EPOP antagonist", "antagonist of C17orf96", "C17orf96 antagonist", refer to a molecule capable of binding to EPOP, inhibiting or reducing EPOP expression levels, or neutralizing, blocking, reducing or interfering with EPOP biological activities, including, but not limited to, methyltransferase activity mediated by the core subunits of PRC2, such as EZH1 or EZH2. For instance, a molecule capable of inhibiting or reducing EPOP expression levels, or neutralizing, blocking, reducing, or interfering with EPOP biological activities can exert its effects by binding to one or more EPOP binding sites on a PRC2 complex (e.g., EED, EZH2, PCLs). Included as EPOP inhibitors that can be used in the methods of the present disclosure are small compounds such as small RNAs complementary to at least a fragment of a nucleic acid molecule encoding an EPOP polypeptide (e.g., antisense nucleic acid, siRNA, shRNA, miRNA), locked nucleic acids hybridizing to at least a fragment of a nucleic acid molecule encoding an EPOP polypeptide, peptide nucleic acids binding to at least a fragment of a nucleic acid molecule encoding an EPOP polypeptide, morpholinos targeting at least a fragment of a nucleic acid molecule encoding an EPOP polypeptide, inhibitory nucleic acids against EPOP, gapmers or aptamers against EPOP, triple helix molecules against EPOP, ribozymes targeting EPOP, antibodies against EPOP, zinc finger proteins targeting EPOP (e.g., zinc finger nucleases or zinc finger transcription factors), transcription activator-like effector proteins targeting EPOP (e.g., transcription activator-like effector nucleases or transcription factors based on transcription activator-like effectors), CRISPR-based systems targeting EPOP (e.g., systems combining a guide RNA and a catalytically active CRISPR enzyme for cleaving DNA or RNA, systems combining a guide RNA and a catalytically inactive CRISPR enzyme fused or not to a functional domain for gene silencing and epigenetic modifications), meganucleases targeting EPOP, argonaute proteins targeting EPOP or any polypeptides including chimeric ones that bind to EPOP. Included as EPOP inhibitors that can be used in the methods of the present disclosure are non-peptide small molecules such as chemical compounds, that are capable of binding to EPOP, inhibiting or reducing EPOP expression levels, or neutralizing, blocking, reducing or interfering with EPOP biological activities, including, but not limited to, methyltransferase activity mediated by the core subunits of PRC2, such as EZH1 or EZH2. For instance, the EPOP inhibitors reduces or inhibits, by at least 10%, 20%, 30%, 40%, 50%, 60%, 70%, 80%, 90% or more, the expression level or biological activity of EPOP. Included in this definition are EPOP-specific inhibitors and non-specific inhibitors of EPOP such as inhibitors of EPOP isoforms, inhibitors of EPOP paralogs or inhibitors of EPOP variants.

As used herein, the terms "inhibitor of LCOR", "LCOR inhibitor", "inhibitor of C10orf12", "C10orf12 inhibitor", "antagonist of LCOR" and "LCOR antagonist", "antagonist of C10orf12", "C10orf12 antagonist", refer to a molecule capable of binding to LCOR, inhibiting or reducing LCOR expression levels, or neutralizing, blocking, reducing or interfering with LCOR biological activities, including, but not limited to, methyltransferase activity mediated by the core subunits of PRC2, such as EZH1 or EZH2. For instance, a molecule capable of inhibiting or reducing LCOR expression levels, or neutralizing, blocking, reducing, or interfering with LCOR biological activities can exert its effects by binding to one or more LCOR binding sites on a PRC2 complex (e.g., EZH2). Included as LCOR inhibitors that can be used in the methods of the present disclosure are small compounds such as small RNAs complementary to at least a fragment of a nucleic acid molecule encoding an LCOR polypeptide (e.g., antisense nucleic acid, siRNA, shRNA, miRNA), locked nucleic acids hybridizing to at least a fragment of a nucleic acid molecule encoding an LCOR polypeptide, peptide nucleic acids binding to at least a fragment of a nucleic acid molecule encoding an LCOR polypeptide, morpholinos targeting at least a fragment of a nucleic acid molecule encoding an LCOR polypeptide, inhibitory nucleic acids against LCOR, gapmers or aptamers against LCOR, triple helix molecules against LCOR, ribozymes targeting LCOR, antibodies against LCOR, zinc finger proteins targeting LCOR (e.g., zinc finger nucleases or zinc finger transcription factors), transcription activator-like effector proteins targeting LCOR (e.g., transcription activator-like effector nucleases or transcription factors based on transcription activator-like effectors), CRISPR-based systems targeting LCOR (e.g., systems combining a guide RNA and a catalytically active CRISPR enzyme for cleaving DNA or RNA, systems combining a guide RNA and a catalytically inactive CRISPR enzyme fused or not to a functional domain for gene silencing and epigenetic modifications), meganucleases targeting LCOR, argonaute proteins targeting LCOR or any polypeptides including chimeric ones that bind to LCOR. Included as LCOR inhibitors that can be used in the methods of the present disclosure are non-peptide small molecules such as chemical compounds, that are capable of binding to LCOR, inhibiting or reducing LCOR expression levels, or neutralizing, blocking, reducing or interfering with LCOR biological activities, including, but not limited to, methyltransferase activity mediated by the core subunits of PRC2, such as EZH1 or EZH2. For instance, the LCOR inhibitors reduces or inhibits, by at least 10%, 20%, 30%, 40%, 50%, 60%, 70%, 80%, 90% or more, the expression level or biological activity of LCOR. Included in this definition are LCOR-specific inhibitors and non-specific inhibitors of LCOR such as inhibitors of LCOR isoforms, inhibitors of LCOR paralogs or inhibitors of LCOR variants, including, but not limited, to inhibitors of PRC2 associated LCOR isoform 1 (PALI1) and inhibitors of PRC2 associated LCOR isoform 2 (PALI2).

As used herein, the terms "treat", "treating," and "treatment" refer to the management and care of a patient for the purpose of combating a disorder, disease, to alleviate or abrogate one or more symptoms or complications associated with the disorder or disease, to eradicate the cause(s) of the disorder or disease, or the disorder or disease itself. the terms "treat", "treating," and "treatment" also refer to methods of delaying and/or precluding the onset of a disorder or disease, and/or its attendant symptoms; barring a subject from acquiring a disorder or disease; or reducing a subject's risk of acquiring a disorder or disease. The terms "treat", "treating," and "treatment" can also include treatment of an animal model or a cell in vitro.

As used herein, the term "subject" is interchangeable with a "subject in need thereof" both of which refer to any mammal who has been diagnosed with, has symptoms of, or having an increased risk developing an eye disorder relative to the population at large. The mammal can be any mammal, e.g., a human, primate, mouse, rat, dog, cat, cow, sheep, pig or a horse. Preferably, the mammal is a human. The eye disorder can be any eye disorder, e.g. an eye disorder that is a cancer or that is not a cancer. Preferably, the eye disorder is not a cancer, e.g. an inherited eye disorder, a neurodegenerative disorder affecting the eye, an ocular autoimmune disease, an inflammatory disease affecting the eye. More preferably, the eye disorder is an inherited retinal disorder, a retinal degeneration, a neurodegenerative disease of the retina, an ocular autoimmune disease affecting the retina or an inflammatory disease affecting the retina. The eye disorder also includes a disorder affecting retinal neurons. To illustrate, for purposes of prevention, a subject may be a human subject having a degeneration of retina function, characterized by cell death of retinal neurons, and so on.

Examples of such eye disorders include, but are not limited to, color vision deficiency, computer vision syndrome, diabetic retinopathy, floaters & spots, glaucoma, learning-related vision problems, macular degeneration, nystagmus, ocular allergies, ocular hypertension, retinal detachment, retinitis pigmentosa, subconjunctival hemorrhage, uveitis, leber congenital amaurosis, cone rod dystrophies, night blindness, vitreoretinal dystrophies, erosive vitreoretinopathy, usher syndrome, epiretinal membrane, macular hole.

As used herein, the term "retinal neuron" refers to any neural cell of the mammalian retina, playing a specific role in transmitting and processing visual information. Included in this definition are photoreceptors such as rod and cone photoreceptors, retinal ganglion cells, bipolar cells, amacrine cells and horizontal cells.

As used herein, the terms "therapeutically effective amount" and "effective amount" refer to the amount of a compound that, when administered to a mammal, is sufficient to prevent development of, or alleviate to some extent, at least one of the symptoms of the disorder or condition being treated. These terms also refer to the amount of a compound that is sufficient to elicit the biological or medical response of a biological molecule (e.g., a protein, enzyme, DNA, or RNA), cell, tissue, system, organism such as an animal or a human.

Materials and Methods

Mice and Livestock:

The wild-type (WT), Retinal degeneration-1 (Rd1), and Rd1;Bmi1$^{-/-}$ mice in the FVB background, and C57/B16 WT mice expressing the Green Fluorescent Protein (GFP) the Cone-Rod Homeobox (Crx) gene activation were maintained in animal facility in a 12 hr light/12 hr dark cycle, with a room temperature of 25° C. and a humidity varying between 50 and 60%. The Crx-GFP mouse was crossed with the Rd1 mice to obtain the Rd1;Crx-GFP. All the animals genotypes were validated by conventional Polymerase chain reaction (PCR) amplification methods using specific primers as described previously (Zencak et al., PNAS 2013; see sets of primers used for genotyping in Table 1). The Fam161a$^{-/-}$ mice with the slow degenerative process was kindly provided by Dror Sharon (university of Hadassah, Jerusalem). The animals were treated according to the Association for Research in Vision and Ophthalmology (ARVO) guidelines and all the experimental procedures were approved by the Ethical Committee of the State of Vaud Veterinary Office, Switzerland.

Human Samples:

The slides sections from Human retinitis pigmentosa and donors were provided by the eye bank of the Jules-Gonin's Eye Hospital (Lausanne, Switzerland) and the protocol for retrospective studies was approved by the Department of Interior Affairs in Switzerland (authorization #035-0003-48/ COC). The study was conducted on human retinal explants as an in vitro model of retina detachment. All procedures conformed to the tenets of the Declaration of Helsinki for biomedical research involving human subjects. Human globes received from Lausanne Eye Bank were considered to be unsuitable for transplantation. The overall health of the donor before death was considered and tissue was rejected from donors with previous history or treatment that might damage the retina, according to the ethical approval by the cantonal (VD) committee on ethic of research human being (CER-VD, protocol No 340-15) and Swiss law.

Compound and Stock Preparation:

The UNC1999 inhibitor was supplied as lyophilized powder from commercial source (#SML0778-5MG, SIGMA). The stock solution was prepared in 100% DMSO according to the manufacturer's instructions. Sufficient amount of DMSO was added to the vial to generate a 10 mM stock solution. For optimal injection procedure, we reviewed three different parameters prior to intermediate solution preparation. Firstly, considering the volume of the vitreous of young mice (post-natal day 8, PN08) which is approximately 5.3 μl; the maximum safe amount (1 μl) that could be injected (final volume 6.3 μl) and the calculated effective dose of 6 μM obtained from increasing doses along with cell culture experiments (see below). Therefore, the stock solution was then diluted in physiological buffer (0.9% NaCl) in order to make a 20 μM intermediate solution for subsequent experiments.

Cell Culture and UNC1999 Treatment:

Mouse Embryonic Fibroblasts (MEF) were maintained in culture in Dulbecco's Modified Eagle's Media (DMEM), 10% fetal bovine serum (FBS) with penicillin and streptomycin, at 37° C., 5% CO2. The day before treatment, the cells were trypsinized and seeded at a density of 50,000 cells on poly-ornithine coated coverslips in 24 well plates. The next day, the media was discarded and fresh media containing various doses of the UNC1999 inhibitor dissolved in dimethyl sulfoxide (DMSO), ranging from 1 μM to 50 μM was added in triplicates, then incubated back at 37° C. for 48H. Control cells received the respective dimethyl sulfoxide DMSO used with the UNC1999. The coverslips were washed 3 times with pre-warmed phosphate buffer saline (PBS) 1× at room temperature (RT). The cells were fixed with 4% paraformaldehyde (PFA) for 12 min at RT. After two more washes in PBS, the cells were immediately proceeded for immunostaining. For western blot analysis, 200,000 cells were seeded in triplicates in 6 wells plates and treated as above.

In Vivo Experiments:

The compound was delivered by intravitreal injection into the eyeball of PN08 Rd1 littermates. The animals (08 in total) were first anesthetized intraperitoneally (ip) with a mixture of 20 mg/kg Ketamine+300 μg/Kg of Dorbene. After 30 min, the recovery was performed by an ip injection of 300 μg/kg of Alzane. When necessary, the future edge of the eyelid was forced to open and maintained with forceps. The injection needle filled with 20 μM UNC1999 solution was inserted carefully into the vitreous through the sclera. A single dose (1 μl) of the intermediate solution was delivered slowly, leading to a final concentration of 2.5-3 μM, with a corresponding DMSO concentration of 0.0317%. For each animal, one eye received the compound whereas the other eye was injected with the vehicle. The injected animals were kept warmed and benefited from closest inspection until they wake up from anesthesia. 400 μl of 5% glucose and paracetamol were administered subcutaneously and intraperitoneally respectively to help for recovery before transferred back to their normal habits. The mice were sacrificed 4 days post injection and the eyeball excised as described below. Before processing, the eyes were carefully inspected for any sign of cataracts and unexpected lesions. Similarly, a single dose of UNC1999 (solution of 36 μM) was administered by intravitreal injection to 2 months old Fam161a$^{-/-}$ mice (slow degenerative process), with repeated injection every week. The animal was sacrificed 4 days after the fourth injection.

Protocol for Preparing Human Retinal Explants:

Procedure of eye dissection: following the cornea donor retrieval, the posterior segment was recovered; following the removal of the vitreous, then the sclera and retina were cut in a flower shape with 4 cuts. Next the retina was detached from the retina pigmented epithelium (RPE), choroid and sclera, in order to achieve the in vitro model of retina detachment. Control explants were cultivated with RPE. The peripheral retina was dissected into small pieces, minimum 5 mm×5 mm. Retinal explants were placed on Millipore membrane inserts (Millicell Culture Plate Inserts, Merck-Millipore, Merck, Darmstadt, Germany), which were then placed in a 6 well plate (NalgeneNunc, Rochester, New York, USA), with 1.5 mL of medium was then administered into each well. The DMEM/F12medium contained B27 (1/50), FBS (1%), Penicillin (1%) and Steptomycin (1%). The medium was maintained at 37° C. and was exchanged every 48 hours. During this protocol fixation was made at 24 h, 72 h, 5 days and 7 days after dissection. Fixation was achieved using 4% PFA and 30% Sucrose, explants were mounted using Yazulla and subsequently frozen at −20° C. There were four retinal explants that fulfilled the inclusion criteria (n=4). All 4 explants were negative for known retinal disease. Each biological sample was divided in two groups: RD group (without RPE), n=4 and control group (with RPE), n=4 and served for all the time points analyzed.

Histology and Tissue Processing:

The animals were sacrificed by a 7 min exposure to CO2. The Histology was performed on enucleated eyes. Prior to cryosectioning, the eye globes were excised from the optic nerve and were perforated at the cornea level (a single tiny hole) with 25 G needle and transfer to 4% PFA (w/v) at RT. After 1 h incubation period, the eyes were washed in PBS 1× before being transferred in 30% sucrose over night at 4° C. The eyes were embedded in yazula and frozen at −20° C. and then 14 μm sections were performed with cryostat. The sections were collected on six serial slides for each eye. All quantifications were performed on the most central cryosections including (or surrounding) the optic nerve. Measurements of rows of nuclei were taken at the same geographic area for both dorsal and ventral sides of the retina in all sections and slides analyzed. The data were pooled as a mean for the dorsal or ventral zone of the retina Generation of Purified Photoreceptors from WT and Rd1 Mice:

Crx-GFP;WT and Crx-GFP;Rd1 mice expressing the GFP were sacrificed at PN12 and enucleated as described above. The retina was then isolated from the eye globe and the isolated retinal tissue was transferred in 2 ml microcentrifuge tube containing aliquot of reduced serum media OpTi-MEM (Life Technologies). Four to six retinas from the same littermate were pulled together before Papain-I dissociation (Papain dissociation kit, Worthington biochemical) according to manufacturer's instructions. The sample preparation was further loaded to the column of MoFlo Astrio system (Beckman Coulter's company at the UNIL platform, CHUV) equipped with a 488 nm green laser to excite the GFP. Cells were sorted at constant excitation and collected in PBS 1×, pelleted, then snap frozen and immediately stored at −80° C. until the day of analysis.

Epitope Retrieval for H3K27Me3 Staining:

The frozen slides were warmed at RT, rehydrated and washed 3 times with PBS 1×. The slides were placed in plastic container (25×75 mm) and filled up with 10 mM citrate buffer (pH 6.0) and transferred in household microwave oven. The samples were heated at 600-W (medium power) for approximately 2 min until the liquid starts boiling. The buffer was permanently refilled and boiled again sequentially for a total period of 5 min. The sections were then cooled slowly in citrate buffer at RT for 30 min, rinsed thoroughly with PBS 1× prior to immunohistochemistry.

Immunohistochemistry:

Immunohistochemistry was performed on treated and non-treated slides. The sections were washed 3 times with cooled PBS 1× before being permeabilized with Triton X-100 for 20 min to further allow optimal antibodies-antigens interactions everywhere in the tissue and cells. The sections were blocked for 1 h with buffer containing 3% BSA (w/v), 5% NGS (v/v) in PBS 1× containing 0.3% Triton X-100. Appropriate antibodies dilutions (see list of antibodies with their respective applications in Table 2) were prepared in blocking solution and sufficient amount were laid and transferred to 4° C. over-night. The next day, the antibodies solutions were shed-off and the remaining non-interacting probes were washed off 3 times with PBS 1×. Interacting probes were then detected by applying a solution of appropriate conjugated secondary antibodies Alexa Fluor 488 or Alexa fluor 633 diluted in PBS 1× 1 h at RT. Finally, the nuclei were counterstained with 4',6-diamidino-2-phenylindole (DAPI) solution prepared in PBS. Alternatively, for difficult to retrieve antigens such as cGMP and CDK4, special conditions were applied: Successful detection of CDK4 requires signal amplification, either with TSA* fluorescein detection kit (PerkinElmer) or 3,3'-diaminobenzidine (DAB) revelation system (Dako) according to providers instructions. The cGMP detection was achieved by permeabilizing the membrane with soft detergent solution (0.1% Triton X-100) and using Tris buffer (TBS) throughout the incubation steps. All the preparations were mounted with Mowiol and measurements were taken using an Olympus BX60 fluorescence microscope or Zeiss confocal microscopy (LSM 510 3.2 software).

Signal Quantification and Analysis: For each antigen, eight sections flanking the optic nerve were analyzed per slide. The positive signal in the outer nuclear layer (ONL) nuclei was counted along the dorso-ventral plane, by subdividing individual section into 6 main (3 dorsal and 3 ventral) fields delineated with the magnification of 20× objective. Each dorsal or ventral field was assigned to be central when they were closest the most to the optic nerve, whereas the farthest most from the optic nerve were considered peripheral. The total number of stained cells in Rd1 was then estimated per section and the averages per field were scored in comparison to the WT mice.

Terminal dUTP Strands Break Labeling:

Cell death was monitored with the in-Situ cell death detection Kit (Cat: 12156792910. Roche diagnostics; Rotkreuz, Switzerland) and the terminal deoxynucleotidyl transferase dUTP Nick-ends labeling (TUNEL) was performed according to the manufacturer's instructions.

Preparation of Tissue Homogenate:

Purified photoreceptors were thaw on ice, washed 2× in PBX 1× and homogenized in 50 mM Tris-HCl pH 7.6, 150 mM Nacl, 1 mM EDTA, 0.25% Triton X-100 and 0.25% Nonidet NP40, and proteases inhibitors cocktail (Sigma). Subsequent sonication step at 30% amplitude for 3 s at 4° C. was performed to release the components of the nuclei. Cytoskeleton and debris were pelleted at 14,000 g for 10 min, and the cleared lysate collected, transferred in small aliquots in fresh Eppendorf tubes and stored at −80° C. until the day of analysis.

Western Blotting:

Equal amount (twenty micrograms) of lysate was resolved on 12% polyacrylamide gel electrophoresis under constant voltage. The proteins were then transferred (BioRad, Switzerland) to polyvinylidene (PVDF) membrane at RT. The membrane was blocked 1 h with 5% non-fat dried milk in PBS 1× at RT. The membrane was incubated ON with the primary antibody diluted in 5% non-fat dried milk, 0.1% PBS Tween 20 (PBST) as indicated (see Table 1 and Table 2). The membrane was washed 3 times with PBS 0.1% Tween 20 and further incubated 1 h at RT with Horse Radish Peroxidase (HRP) conjugated secondary antibody diluted in PBS 0.1% Tween 20. The membrane was washed 2 times with PBST and once with PBS 1×. Finally, the highest sensitivity chemiluminescent HRP substrate (Witec AG) was added and the bands revealed with Fujifilm chemiluminescent cassette (Amersham) according to manufacturer's instructions.

EXAMPLES

Example 1: H3K27Me3 Accumulation in Photoreceptors of Retina Degeneration Mouse Models In previous studies, we showed that cell death in Rd1 photoreceptors was tightly dependent on BM11 polycomb group protein (B-cell specific MMLV integration site-1) and that its molecular action was however, independent on the downstream conventional Ink4a/Arf pathway (Zencak et al., 2013). To reveal whether BM11 has an autonomous effect in Rd1 photoreceptors, we crossed the conditional Rd1; Bmi1$^{flox/flox}$ mouse with the Opsin::Cre line to generate the Rd1;Opsin::Cre; Bmi1$^{flox/flox}$ mice in order to distinctly induce Bmi1 deletion specifically and uniquely in photoreceptors (FIG. 2A). In mice carrying the Cre recombinase activity, cell type specific deletion of Bmi1 was confirmed in photoreceptors by immunohistochemistry of BM11 at postnatal day 16 (PN16) (FIG. 2A). However, despite an absence of BM11 expression in large areas of the outer nuclear layer (ONL) composed of photoreceptors, no rescue of the ONL thickness was seen at PN16, as compared to the Rd1; Bmi1$^{-/-}$ (FIG. 2A and Zencak et al., 2013). This suggests that the molecular censors triggering cell death might be switched on immediately after photoreceptor differentiation and prior to the time where photoreceptors acquire their full maturity during the initiation of the Opsin promoter activity.

Because the Polycomb Repressive Complex-2 (PRC2) acts prior to BM11 to regulate genes, we thus hypothesized, that PCR2 may be already involved in this death process and we investigated histones posttranslational modifications (HPTMs). Enhancer of the Zest homolog-2 (EZH2) belongs to the PRC2 and mediates the trimethylation on Lysine 27 of Histone3 (H3K72me3) to favor chromatin compaction and gene repression in association with PRC1 through BM11. The screening of the retinal sections during degeneration from the PN16 Rd1;Opsin::Cre; Bmi1$^{flox/flox}$ mice for selected histones post-translational modifications (HPTMs) has revealed site specific H3K27 hyper-trimethylation in some cells in ONL (FIG. 2D). Considering this peculiar enrichment of H3K27me3 in photoreceptors within the degenerating retina, we considered to give more attention to its biological significance and potential contribution to the disease process.

In PN12 Rd1 mice, immunohistochemistry against H3K27me3 shows a robust nuclear labeling in several nuclei composing the outer nuclear layer (ONL) (FIG. 2C). Because EZH2 and H3K27me3 levels diminishes already quantitatively in young WT mice after birth (Rao et al., 2010), and to rule out any cross reactivity due to a nonspecific interaction of the antibodies, we obtained an additional antibody from different commercial source (mAb6002). A strong co-localization was obtained with both labeling, and thus, validating the specificity of the H3K27me3 staining. In contrast, no H3K27me3 dense mark was observed in the ONL of the WT retina (FIG. 2C), and this observation is consistent with what was previously described for mature WT retina (Rao et al., 2010). H3K27me3 co-localizes in cells expressing the photoreceptor specific protein, RHODOPSIN (Rho, FIG. 2D), attesting that enhanced H3K27me3 mark is present in these retinal neurons.

To verify whether H3K27me3 accumulation also occurs in different rodent models of retinal degeneration, we investigated the H3K27me3 mark in the Rd10, RhodopsinP23H, RhodopsinS334ter, Rhodopsin$^{-/-}$, and Fam161a$^{-/-}$ retina. The Rd10 mouse is another retinal degeneration model almost similar to Rd1 (PDE60 deficiency) (Chang et al., 2007, Barhoum et al., 2008). However, the onset of retinal cell loss is delayed, though the degenerating process is even faster (in our colony). In this model, the number of pyknotic cells in the central retina peaks at PN25 and differs from Rd1 in which half of photoreceptor cell death occurs in ONL at PN13-14 (Portera-Cailliau et al., 1994.). Interestingly, staining of Rd10 retinae sections with anti H3K27me3 polyclonal antibody also showed a marked increase of the H3K27me3 mark (FIG. 3, bottom panel). In addition, we also observed a strong presence of the H3K27me3 mark in the ONL of two other models of autosomal dominant RP, the P23H mouse and the 5334 ter rat respectively (FIG. 3, top and middle panels respectively), as well as in the Fam161$^{-/-}$ and Rhodopsin$^{-/-}$ mice having a slow degeneration kinetics (data not shown).

Therefore, these data reveal that H3K27me3 accumulation is a general phenomenon affecting different types of retinal degeneration.

Furthermore, to determine if the alteration of H3K27me3 mark distribution and its basal level in Rd1 is particular or reveals general deregulations of HPTMs homeostasis, we examined the pattern and distribution of H3K9me2 and H3K4me3 marks, also known to be enriched at the TSS of silent and active genes respectively. Upon staining, we did not detect any differential expression of neither H3K9me2 nor H3K4me3 between the WT and Rd1 ONLs (FIGS. 4A&B).

Altogether, these results strongly reveal that the photoreceptors of rodents undergo specific chromatin remodeling during the degenerative process, and the H3K27me3 mark deregulation appears to be particular to degenerating photoreceptors.

Example 2: H3K27Me3 Accumulation in Human Patient Retina Suffering from Retinitis Pigmentosa To better implement the relevance of the H3K27me3 hypermethylation in retinal disorders, we wondered if this phenotype could also occur in Human retina. The eye globes from one Human affected by retinitis pigmentosa and one healthy donor were collected and processed to investigate for the presence of H3K27me3 in their retina. In contrast to the human donor sample (FIG. 5A), the presence of the H3K27me3 hypertrimethylation mark was noticeably enriched at the periphery of both RD retinas, in the areas where the degenerative process started initially, and also in the near peripheral area (FIG. 5B, data not shown). By contrast, few H3K27me3 marks were observed in the central retina. The pattern with high H3K7me3 mark numbers in the periphery with a rarefaction towards the central retina is in line with the pattern of cell death generally observed in patients affected by Retinitis pigmentosa.

Together, these data spots the H3K27me3 methylation as a hallmark of the degenerative process in RD and may be linked to cell death mechanisms.

Example 3: H3K27Me3 Accumulation in Retina Degeneration Mouse Models Precedes Late Events of Photoreceptor Death Processes To get better insight into the temporal manifestation of H3K27me3 in Rd1 retina, we evaluated the time course of this mark, starting from PN5 prior to disease onset, until PN15 where only less than 30% of cells remain in the Rd1 retina. H3K27me3 was already detectable at PN8 (FIG. 2E) and its temporal expression pattern was tightly linked to the degenerative course already described (Zencak et al., 2013) and precedes the expression of the proliferation marker Ki-67 (FIG. 2C, bottom panels and 2F). The number of cells with H3K27me3 increases with time until PN13, which coincides with the time where more than 50% of cells had degenerated in Rd1 mice. Moreover, we noticed that the H3K27me3 signal was primarily enriched at the central part of the retina at the region flanking the optic nerve (PN8-12), and onward toward the periphery, as the disease progresses (FIG. 2G, data is shown only at PN12). Importantly, and in line with our previous works revealing that the deletion of Bmi1 delays retinal degeneration, the number of H3K27me3 positive cells was significantly decreased in Rd1;Bmi1$^{-/-}$ mice (FIG. 2H). Nonetheless, the presence of the H3K27me3 mark is not abolished and thus reveals that a residual methyl transferase activity is independent on the BM11 presence as suggested in FIG. 2B. Interestingly, Western blot analysis of purified Crx-GFP-positive photoreceptors has revealed an increase of the polycomb repressive core component EZH2 protein content in Rd1 in photoreceptor samples (FIG. 2I).

Together, these data suggest that H3K27me3 accumulation is the consequence of EZH2 upregulation and activity, and that its pattern strongly correlates with disease severity progression in the Rd1 mice.

The course of cell death in photoreceptors is orchestrated by a compilation of distinct molecular events (Paquet-Durand et al., 2014). In Rd1 rod photoreceptors, the cGMP accumulation commonly occurs during the very early stage of photoreceptor cell death cascade, while Terminal dUTP strands break labeling (TUNEL) reveals cell undergoing their DNA fragmentation phase. As the early time frame at which the H3K27me3 appears coincides with the time frame of cGMP intracellular increase in Pde6 null mouse retina (Farber & Lolley, 1974), we asked whether cGMP and H3K27me3 co-exist in the same cell in order to determine if H3K27me3 appears downstream or upstream. We observed no cells in which the cGMP staining co-localizes with H3K27me3 in Rd1 retina at PN12 (FIG. 6A top panel), suggesting that H3K27me3 may appear after the cGMP accumulation. Among the H3K27me3-positive photoreceptors, 60% were also TUNEL-positive, whereas 40% of the TUNEL-positive population localizes with H3K27me3, suggesting a relationship between H3K27me3 and cell death in this mouse model (FIG. 6A bottom panel, FIG. 6b). In addition, 65% of the H3K27me3 were also positive for CDK4 at PN 12 (FIG. 6A middle panel, FIG. 6C) suggesting a strong relationship with the expression of this kinase. The time course expression of H3K27me3 and CDK4 demonstrated an elevated number of H3K27me3 prior to the appearance of CDK4 positive cells all over the time course of the analysis (FIG. 6C). In a previous study, we observed that 75% of the TUNEL-positive cells in the ONL were also positive for CDK4.

Altogether these results reveal successive appearances of H3K27me3 and CDK4 prior cell death suggesting a stepwise mechanism of degeneration involving EZH2 as an intermediate inducer of photoreceptor death.

Example 4: Pharmacological Inhibition of EZH2 Protects Photoreceptors Against Degeneration In Vivo The increased basal levels of EZH2 in Rd1 mice compared to WT (FIG. 2I) and its prominent positioning in biological processes controlling cell identity indicates that the activity of this particular methyltransferase enzyme may be augmented to target new set of genes during the early stage of the degenerative process. In order to pharmacologically control the levels of H3K27me3 in vivo, we used the EZH1/EZH2 inhibitor, UNC1999 to target its catalytic SET domain (Konze et al., 2013, Xu et al., 2015). In proliferating mouse embryonic fibroblasts, UNC1999 at 2.5 µM was efficient to block the endogenous levels of H3K27me3 compared to DMSO control (FIG. 7A, FIG. 7B), thereby suggesting the efficient doses for in vivo investigation. Based on this result, the Rd1 (PN8) retina were then exposed to 2.5 μM of UNC1999 (concentration extrapolated in the eye after the injection), and the efficacy of the treatment were evaluated by monitoring the H3K27me3 mark and the extent of cell death upon TUNEL staining at 4 days post injection. The hyper H3K27me3 signal was preserved in DMSO treated eye, whereas such signal strongly declined (by 75%) in the ONL of UNC1999 injected retina (FIG. 7C, FIG. 7E). Interestingly, the number of TUNEL positive cells substantially decrease by 70% in corresponding area, as compared to DMSO treated eye (FIG. 7D, FIG. 7F).

The Fam161a KO mouse is another disease model of RP with a slow retina degeneration resulting of the loss of around 80% of the photoreceptors at 6 months. Compared to Rd1, the Fam161a$^{-/-}$ mimics a slow degenerative process. Similarly, to the Rd1 mice, we administered a single dose of UNC1999 to 2-month-old Fam161a$^{-/-}$ mice. However, the experiment was repeated every week until their 4th injections and the animals were sacrificed 4 days later of age. The animals were sacrificed one week later and the retinal sections were analyzed for photoreceptors cell survival and H3K27me3 presence along the dorso-ventral axis (FIG. 7G, FIG. 7H). Our data showed a significant preservation of the number of rows in the ventral ONL we quantified. No significant difference was observed in the dorsal compartment. We did not observe any statistical differences with the levels of H3K27me3 hyper trimethylation between the injected and non-injected side, probably because of the loss of the effectiveness of the compound due to the time encompassing the last day of injection and the time of sacrifice.

To test whether the UNC1999 dose tested (10 M) has a toxic effect on retina function, the retina activity of control (injected with the vehicle, DMSO) and UNC1999 treated C57/B16 healthy mice was recorded by ERG before and one week after intravitreal injection (FIG. 12). In scotopic condition, the b-wave maximum amplitude baseline of the DMSO treated group was a bit higher than the UNC1999 group one before the injection. Both groups showed similar responses one week after the injection with no significant differences with the baseline (FIG. 12A). A comparable observation was made in photopic observation, with the exception of the 3 cda/s.m$^2$ stimulation, for which both DMSO and UNC1999 treated animals showed a reduced response (FIG. 12B). In flicker condition, a reduction of the response occurred at 5 Hz for both treated groups, in a lesser extent at 10 Hz and no differences were observed between all groups for 15 Hz. The overall results suggest that the injection procedure alters very partially some rods, but had no substantial effects on cones.

Collectively, these data strongly suggest that inhibiting EZH2 activity in vivo contributes to reduce the number of TUNEL positive cells and to delay photoreceptor degeneration in mouse models of retinal degeneration.

Example 5: Activation of Cell Death Pathways During Human Photoreceptor Death Processes and Evidence of EZH2 Activity During Retina Degenerations We developed an in vitro model of human retinal detachment (RD) to investigate which death pathway is activated. This model consists on the culture of human retina explant without retinal pigment epithelium (RPE) compared to retina with RPE cells.

Number of Photoreceptors' Layers:

In all four explants, the number of photoreceptor layers was quite stable in the control group, while there was a slight decrease in the RD group over time. In this group, at 5DIV and 7DIV, the number of photoreceptors rows was decreased by around 25% in comparison to 1DIV (P<0.04). The difference between groups analyzed in every time-point, was not statistically significant, except after 1DIV (FIG. 8 A-B, Table 3) where the RD group showed a high number of photoreceptors at the beginning of the experiment. This reveals that, although the retina pieces from a same donor were distributed between the two groups, some heterogeneity exists in a same tissue sample. Nonetheless, each group contained retina with similar numbers of photoreceptor rows (see SEM bars in FIG. 8). Thus, the evolution of photoreceptor number in the same group better reveals the health of retina. To note, the RD retina showed a significant decline in photoreceptor rows, whereas the control group did not (Table 4).

Figure 9:
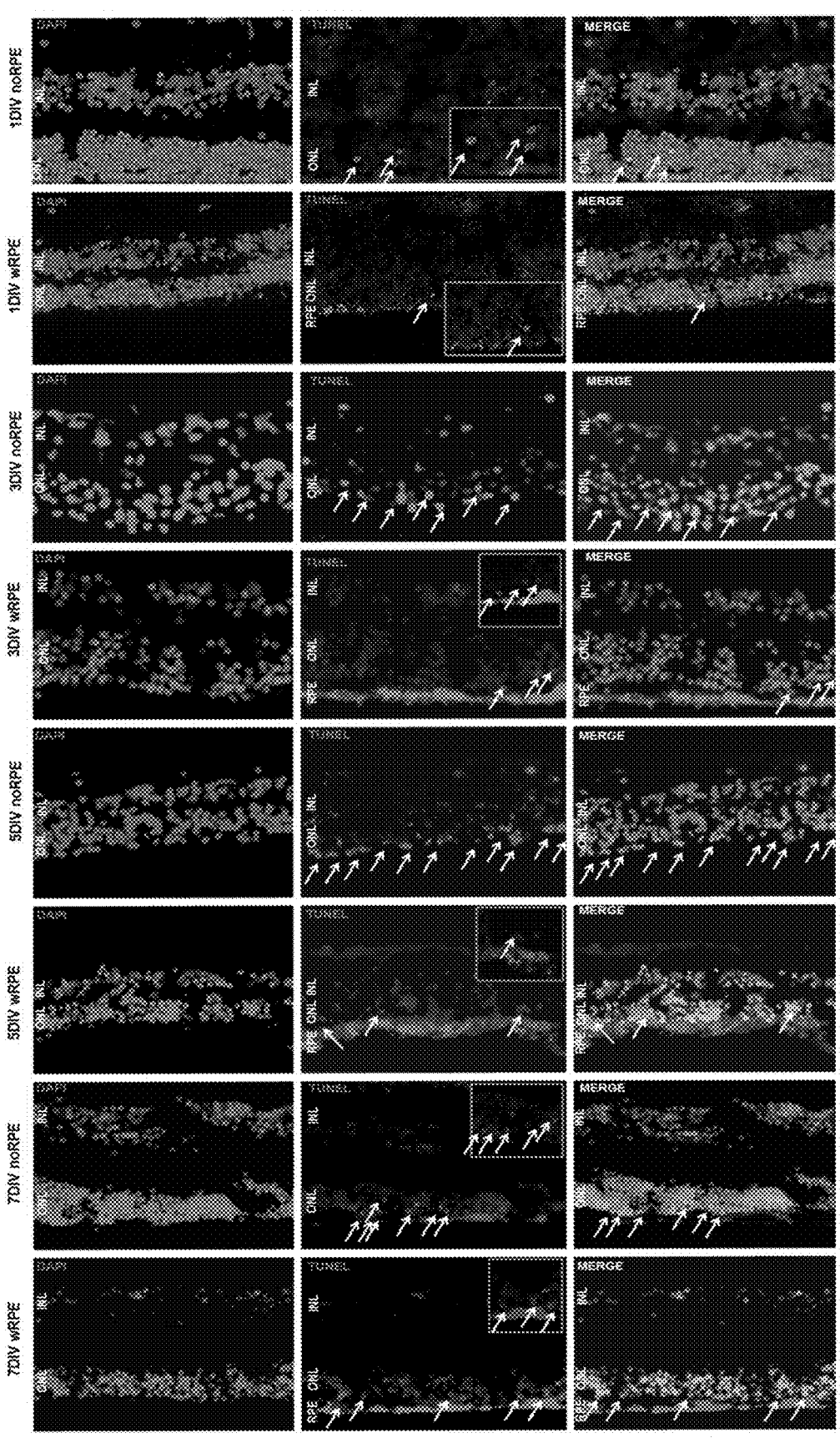

TUNEL Staining; Cell Death Marker:

TUNEL positive cells were present from the beginning of the experiment in low level in the control group despite the different postmortem delays (12 h, 14 h, 23 h and 24 h) and the dissection procedure of the tissue. The number of TUNEL-positive cells increased significantly at 3 DIV and peaked at 3 and 7 DIV. An increase of more than 10-fold of TUNEL-positive cells was observed at 3 DIV between the RD and the control groups (P=0.0014) (FIG. 9 and Table 3 and 5). Interestingly, this peak of cell death coincides with this described for rhegmatogenous retinal detachment in vivo (Hisatomi et al., 2001, Arroyo et al., 2005). A significant 30% increase of TUNEL positive cells continued to occur between 3 DIV and 7DIV with a high variation at 5 days suggesting a biphasic cell death process (FIG. 8-9, Table 5). We then investigated potential actors of the cell death process.

Canonical Apoptotic Pathway is not Activated in Human RD Group:

Caspase-3 is the final effector of apoptosis and was chosen to reveal the extent of apoptotic events in the retina with and without RPE. Surprisingly, very rare cells in the ONL were present in both groups and no peaks of apoptosis were identified (data not shown).

Apoptosis-Inducing Factor (AIF) Staining:

AIF represents a caspase-independent apoptogenic factor. AIF is normally localized in mitochondria membranes. During the cell death AIF is released, then it translocates to the nucleus (for review and retina see Hisatomi et al., 2001, Hisatomi et al., 2008). We observed that AIF was present in the ONL at 1DIV and with a marked peak at 3DIV in the RD group. The peak of AIF positive cells paralleled the peak of TUNEL positive cells observed at 3DIV (FIG. 8, Table 3). The increase was about 14 folds in comparison to the control group (p=0.02). At 5DIV and 7 DIV there were almost no visible AIF positive cells.

The Cell Cycle Marker CDK4 is Moderately Expressed During the Degenerative Process in Absence of RPE:

No CDK4 was observed in the photoreceptor nucleus of the control group after 1 DIV and only very few cells expressed this protein between 3 to 7 DIV. In the RD group, CDK4 positive cells are present starting at 1 DIV (FIG. 8, Table 3 and Table 6), their number moderately increased afterwards and remained stable between 3 to 7 DIV. The mean number of CDK4 positive cells in the group of explants mimicking RD was 3.07±2.31, in all the time-points, while in the control group this number was 1.25±1.38. Note that the numbers of CDK4 positive cells are much lower in comparison to TUNEL-positive ones (FIG. 8). Comparison between the two groups showed statistical difference at each time-point, except for 5DIV (FIG. 8, Table 3).

Epigenetic modifications of the H3K27me3 mark occurs at the late stage of the degenerative process: Recent works described epigenetic modifications during the course of retinal degeneration with a small increase of the H3K27me3 mark level in retina extract (Zheng et al., 2018). We also observed that epigenetic modifications occur at the Histone level in some rodent models of retinitis pigmentosa (unpublished data), we investigated the H3K27me3 mark known to regulate gene repression (Wahlin et al., 2013). In the control group, the number of H3K27me3-positive cells in the ONL remained low until 5 DIV and showed a slight elevation at 7 DIV, whereas a marked increase of this mark was observed at 5 DIV in the RD group and stayed elevated at 7DIV, although partially reduced (FIG. 8, FIG. 9, FIG. 10, Table 3 and Table 7). Note that the elevated number of H3K27me3-positive cells appears after the peak of TUNEL-positive cells at 3 DIV, but paralleled the number of dying photoreceptors afterwards. Seizing the opportunity of our institutional Eye bank, we analyzed an eye globe from a patient suffering from a uveal melanoma provoking a local retinal detachment at the retina periphery. In the thinner part of the ONL, we observed several photoreceptors positive for the H3K27me3 mark, whereas retina at the center, far from the tumor location, showed a homogenous discrete labelling of this mark (FIG. 11).

These data suggest that EZH2 is participating to photoreceptor death during long term retinal detachment.

In conclusion, AIF expression coincides with the first peak of cell death, whereas the H3K27me3 mark increased before the second elevation of cell death, suggesting that photoreceptor death is induced by different successive pathways after retinal detachment.

This in vitro model should permit the identification of neuroprotective drugs which may have clinical relevance and shows that H3K27me3 may play an important role during late stage of retinal degeneration.

CONCLUSIONS OF THE EXAMPLES

Altogether, these data demonstrate in several retinal disease conditions, in mouse and human retina, that the H3K27me3 mark correlates with photoreceptor death event and that the inhibition of EZH1/2 activity by UNC1999 markedly delayed retinal degeneration in Rd1 mouse providing thus a new treatment for different families of retinal dystrophies.

Other Embodiments

It is to be understood that while the present disclosure has been described in conjunction with the description thereof, the foregoing description is intended to illustrate and not limit the scope of the present disclosure, which is defined by the scope of the appended claims. Other aspects, advantages, and modifications are within the scope of the following claims.

For instance, as will be apparent to those skilled in the art, while the present disclosure has been described with a number of EZH1 or EZH2 inhibitors as possible solutions, other EZH2 inhibitors currently under investigation for other pathologies (mostly for treatment of cancers—see Tanaka et al., 2015 and Stazi et al., 2017, for reviews; several EZH2 inhibitors have been recently evaluated in preclinical and clinical settings) may also apply to eye disorder treatment.

For instance, Epizyme, Inc., USA, has developed inhibitors of human EZH2 for treating cancer, such as substituted 6,5-fused bicyclic heteroaryl compounds, substituted benzene compounds, N-((4,6-dimethyl-2-oxo-1,2-dihydropyridin-3-yl)methyl)-5-(ethyl (tetrahydro-2 h-pyran-4-yl) amino)-4-methyl-4'-(morpholinomethyl)-[1,1'-biphenyl]-3-carboxamide hydrobromide, 1,4-pyridone bicyclic heteroaryl compounds, hydrochloride salt forms (e.g. International Applications WO 2012/034132, WO 2012/118812, WO 2012/142513, WO 2012/142504, WO2013155464, WO 2013/155317, WO 2014/062732, WO 2014/062733, WO 2014/100665, WO 2014/100646, WO 2014/172044, WO 2015/010078, WO 2015/010049, WO 2015/057859, WO 2015/200650, U.S. Pat. Nos. 8,691,507, 9,376,422, 8,410,088, 8,765,732, 9,090,562, 9,549,931, 9,855,275, 9,006,242, 9,701,666, 9,624,205). GlaxoSmithKline plc, UK, has also developed inhibitors of human EZH2 for treating cancer, such as azaindazoles, indazoles, indole derivatives, substituted benzamide compounds (e.g. International Applications WO 2012/005805, WO 2011/140325, WO 2011/140324, WO 2012/075080, WO 2013/039988, WO 2013/067296, WO 2013/173441, WO 2014/107277, WO 2014/177982, WO 2014/195919, WO 2015/004618, WO 2015/132765, WO 2016/066697, W 02017/191545, U.S. Pat. Nos. 8,637, 509, 8,846,935, 9,018,382, 8,536,179, 8,975,291, 9,114,141, 9,402,836, 9,649,307, 8,765,792, 9,073,924, 9,24,2962, 9,446,041, 9,562,041, 9,956,210, 9,382,234, 9,505,745, 9,790,212, 9,556,157).

Constellation Pharmaceuticals, Inc., USA, has also developed inhibitors of human EZH2 for treating cancer, such as indole derivatives including indole or pyrrole-pyridine-based 6-methylpyridone-containing compounds, 6-methylpyridone-containing compounds and pyridine-containing derivatives (e.g. International Applications WO 2012068589, WO 2013/120104, WO 2014/124418, WO 2014/151142, WO 2015/023915, WO 2016/130396, WO 2018/075598, U.S. Pat. Nos. 9,085,583, 9,371,331, 9,469, 646, 9,980,952, 9,745,305, 9,969,716).

Pfizer Inc., USA, has also developed inhibitors of human EZH2 for treating cancer, such as benzamide and heterobenzamide compounds, aryl and heteroaryl fused lactams, substituted dihydroisoquinolinone compounds (e.g. International Applications WO 2014/049488, WO 2014/097041, WO 2015/193768, WO 2015/193765, U.S. Pat. Nos. 9,040, 515, 9,481,666). Piramal Group, Ltd., IN has also developed inhibitors of human EZH2 for treating cancer, such as substituted bicyclic compounds, heterocyclic compounds (e.g. International Applications WO 2014/155301, WO 2015/104677, WO 2015/110999).

Everfront Biotech, Co., Ltd., TW, has also developed inhibitors of human EZH2 for treating cancer, such as butylidenephthalides (e.g. International Application WO 2017/028602, U.S. Patent Application No. 2017/049746).

Bristol Myers Squibb Inc., USA, has also developed inhibitors of human EZH2 for treating hyperproliferative, inflammatory, infectious, and immunoregulatory disorders and diseases (e.g. International Applications WO 2015/077193, WO 2015/077194, U.S. Pat. Nos. 9,738,630, 9,822, 103). Eli Lilly and Company Inc., USA, has also developed inhibitors of human EZH2 for treating cancer (e.g. International Applications WO 2016/089804, WO 2017/035060, U.S. Pat. Nos. 9,527,837, 9,718,838). Furthermore, academic players have also disclosed EZH2 inhibitors, mostly still for treatment of cancers.

For instance, Yantai University, CN, has developed synthetic compounds for preventing and treating diseases such as cancers. Such compounds can be used for inhibiting enzymes involved in such diseases, including histone methyltransferase EZH2 (e.g. International Applications WO 2014/048313, U.S. Pat. No. 9,518,038, Chinese Applications Nos. 103690531, 103690529, 103690528, 103690530, 103845324, 103845325, 103110621).

Dana Farber Cancer Institute, USA, has also developed inhibitors of human EZH2 for treating cancer, such as pyrazolo-pyridine- and indole-based compounds (e.g. International Applications WO 2014/190035, WO 2016/073956, WO 2017/184999 and WO 2016/073903 that was co-filed with the University of Minnesota, USA).

Agency for Science, Technology and Research, SG, has also developed inhibitors of methyl transferases such as protein lysine methyltransferases for treatment of cancer and epigenetics, such as quinolines and 5,6,7,8-tetrahydroacridine derivatives (e.g. International Application WO 2017/061957).

All publications, patents, and patent applications mentioned in this specification are herein incorporated by reference to the same extent as if each individual publication, patent, or patent application was specifically and individually indicated to be incorporated by reference.

BIBLIOGRAPHY

Arroyo J G, Yang L, Bula D, Chen D F. Photoreceptor apoptosis in human retinal detachment. Am J Ophthalmol. 2005 April; 139(4):605-10.

Arrowsmith C H, Audia J E, Austin C, Baell J, Bennett J, Blagg J, Bountra C, Brennan P E, Brown P J, Bunnage M E, Buser-Doepner C, Campbell R M, Carter A J, Cohen P, Copeland R A, Cravatt B, Dahlin J L, Dhanak D, Edwards A M, Frederiksen M, Frye S V, Gray N, Grimshaw C E, Hepworth D, Howe T, Huber K V, Jn J, Knapp S, Kotz J D, Kruger R G, Lowe D, Mader M M, Marsden B, Mueller-Fahrnow A, Muller S, O'Hagan R C, Overington J P, Owen D R, Rosenberg S H, Roth B, Ross R, Schapira M, Schreiber S L, Shoichet B, Sundström M, Superti-Furga G, Taunton J, Toledo-Sherman L, Walpole C, Walters M A, Willson T M, Workman P, Young R N, Zuercher W J. The promise and peril of chemical probes. Nat Chem Biol. 2015 August; 11(8):536-41.

Barhoum R, Martinez-Navarrete G, Corrochano S, Germain F, Fernandez-Sanchez L, de la Rosa E J, de la Villa P, Cuenca N. Functional and structural modifications during retinal degeneration in the rd10 mouse. Neuroscience. 2008 Aug. 26; 155(3):698-713.

Bemelmans A P, Kostic C, Crippa S V, Hauswirth W W, Lem J, Munier F L, Seeliger M W, Wenzel A, Arsenijevic Y. Lentiviral gene transfer of RPE65 rescues survival and function of cones in a mouse model of Leber congenital amaurosis. PLoS Med. 2006 October; 3(10):e347.

Bracken A P, Dietrich N, Pasini D, Hansen K H, Helin K. Genome-wide mapping of Polycomb target genes unravels their roles in cell fate transitions. Genes Dev. 2006 May 1; 20(9):1123-36.

Cao, R., Wang, L., Wang, H., Xia, L., Erdjument-Bromage, H., Tempst, P., Jones, R. S., and Zhang, Y. Role of histone H3 lysine 27 methylation in Polycomb-group silencing. Science. 2002 Nov. 1; 298(5595):1039-43.

Chang B, Hawes N L, Pardue M T, German A M, Hurd R E, Davisson M T, Nusinowitz S, Rengarajan K, Boyd A P, Sidney S S, Phillips M J, Stewart R E, Chaudhury R, Nickerson J M, Heckenlively J R, Boatright J H. Two mouse retinal degenerations caused by missense mutations in the beta-subunit of rod cGMP phosphodiesterase gene. Vision Res. 2007 March; 47(5):624-33.

Chase A, Cross N C. Aberrations of EZH2 in cancer. Clin Cancer Res. 2011 May 1; 17(9):2613-8.

Czermin B, Melfi R, McCabe D, Seitz V, Imhof A, Pirrotta V. Drosophila enhancer of Zeste/ESC complexes have a histone H3 methyltransferase activity that marks chromosomal Polycomb sites. Cell. 2002 Oct. 18; 111(2):185-96.

Cideciyan A V, Jacobson S G, Beltran W A, Sumaroka A, Swider M, Iwabe S, Roman A J, Olivares M B, Schwartz S B, Komaromy A M, Hauswirth W W, Aguirre G D. Human retinal gene therapy for Leber congenital amaurosis shows advancing retinal degeneration despite enduring visual improvement. Proc Natl Acad Sci USA. 2013 Feb. 5; 110(6):E517-25.

Farber D B, Lolley R N Cyclic guanosine monophosphate: elevation in degenerating photoreceptor cells of the C3H mouse retina. Science. 1974 Nov. 1; 186(4162):449-51.

Gekeler K, Bartz-Schmidt K U, Sachs H, MacLaren RE, Stingl K, Zrenner E, Gekeler F. Implantation, removal and replacement of subretinal electronic implants for restoration of vision in patients with retinitis pigmentosa. Curr Opin Ophthalmol. 2018 May; 29(3):239-247.

Hisatomi T, Sakamoto T, Murata T, Yamanaka I, Oshima Y, Hata Y, Ishibashi T, Inomata H, Susin S A, Kroemer G. Relocalization of apoptosis-inducing factor in photoreceptor apoptosis induced by retinal detachment in vivo. Am J Pathol. 2001 April; 158(4):1271-8.

Hisatomi T, Nakazawa T, Noda K, Almulki L, Miyahara S, Nakao S, Ito Y, She H, Kohno R, Michaud N, Ishibashi T, Hafezi-Moghadam A, Badley A D, Kroemer G, Miller J W. HIV protease inhibitors provide neuroprotection through inhibition of mitochondrial apoptosis in mice. J Clin Invest. 2008 June; 118(6):2025-38.

Giménez E, Montoliu L. A simple polymerase chain reaction assay for genotyping the retinal degeneration mutation (Pdeb(rd1)) in FVB/N-derived transgenic mice. Lab Anim. 2001 April; 35(2):153-6.

Holoch D, Margueron R. Chapter 9—Polycomb Repressive Complex 2 Structure and Function. Polycomb Group Proteins, 2017, p191-224

Jacobson S G, Cideciyan A V, Ratnakaram R, Heon E, Schwartz S B, Roman A J, Peden M C, Aleman T S, Boye S L, Sumaroka A, Conlon T J, Calcedo R, Pang J J, Erger K E, Olivares M B, Mullins C L, Swider M, Kaushal S, Feuer W J, Iannaccone A, Fishman G A, Stone E M, Byrne B J, Hauswirth W W. Gene therapy for leber congenital amaurosis caused by RPE65 mutations: safety and efficacy in 15 children and adults followed up to 3 years. Arch Ophthalmol. 2012 January; 130(1):9-24.

Konze K D, Ma A, Li F, Barsyte-Lovejoy D, Parton T, Macnevin C J, Liu F, Gao C, Huang X P, Kuznetsova E, Rougie M, Jiang A, Pattenden S G, Norris J L, James L I, Roth B L, Brown P J, Frye S V, Arrowsmith C H, Hahn K M, Wang G G, Vedadi M, Jn J. An orally bioavailable chemical probe of the Lysine Methyltransferases EZH2 and EZH1. ACS Chem Biol. 2013; 8(6):1324-34.

Kuzmichev A, Nishioka K, Erdjument-Bromage H, Tempst P, Reinberg D. Histone methyltransferase activity associated with a human multiprotein complex containing the Enhancer of Zeste protein. Genes Dev. 2002 Nov. 15; 16(22):2893-905.

Léveillard T, Mohand-Saïd S, Lorentz O, Hicks D, Fintz A C, Clérin E, Simonutti M, Forster V, Cavusoglu N, Chalmel F, Dollé P, Poch O, Lambrou G, Sahel J A.

Identification and characterization of rod-derived cone viability factor. Nat Genet. 2004 July; 36(7):755-9.

Müller J, Hart C M, Francis N J, Vargas M L, Sengupta A, Wild B, Miller E L, O'Connor M B, Kingston R E, Simon J A. Histone methyltransferase activity of a *Drosophila* Polycomb group repressor complex. Cell. 2002 Oct. 18; 111(2):197-208.

Plath K, Fang J, Mlynarczyk-Evans S K, Cao R, Worringer K A, Wang H, de la Cruz C C, Otte A P, Panning B, Zhang Y. Role of histone H3 lysine 27 methylation in X inactivation. Science. 2003 Apr. 4; 300(5616):131-5.

Paquet-Durand F, Sahaboglu A, Dietter J, Paquet-Durand O, Hitzmann B, Ueffing M, Ekström PA. How long does a photoreceptor cell take to die?Implications for the causative cell death mechanisms. Adv Exp Med Biol. 2014; 801:575-81.

Portera-Cailliau C, Sung C H, Nathans J, Adler R. Apoptotic photoreceptor cell death in mouse models of retinitis pigmentosa. Proc Natl Acad Sci USA. 1994 Feb. 1; 91(3): 974-978.

Rao R C, Tchedre K T, Malik M T, Coleman N, Fang Y, Marquez V E, Chen D F. Dynamic patterns of histone lysine methylation in the developing retina. Invest Ophthalmol Vis Sci. 2010 December; 51(12):6784-92.

Smith A J, Bainbridge J W, Ali R R. Gene supplementation therapy for recessive forms of inherited retinal dystrophies. Gene Ther. 2012 February; 19(2):154-61.

Stazi G, Zwergel C, Mai A, Valente S. EZH2 inhibitors: a patent review (2014-2016). Expert Opin Ther Pat. 2017 July; 27(7):797-813.

Tanaka M, Roberts J M, Qi J, Bradner J E. Inhibitors of emerging epigenetic targets for cancer therapy: a patent review (2010-2014). Pharm Pat Anal. 2015; 4(4):261-84.

Wahlin K J, Enke R A, Fuller J A, Kalesnykas G, Zack D J, Merbs S L. Epigenetics and cell death: DNA hypermethylation in programmed retinal cell death. PLoS One. 2013 Nov. 11; 8(11):e79140.

Xu B, On D M, Ma A, Parton T, Konze K D, Pattenden S G, Allison D F, Cai L, Rockowitz S, Liu S, Liu Y, Li F, Vedadi M, Frye S V, Garcia B A, Zheng D, Jn J, Wang G G. Selective inhibition of EZH2 and EZH1 enzymatic activity by a small molecule suppresses MLL-rearranged leukemia. Blood. 2015 Jan. 8; 125(2):346-57.

Yoo K H, Hennighausen L. EZH2 Methyltransferase and H3K27 Methylation in Breast Cancer. Int J Biol Sci. 2012; 8(1): 59-65.

Yuzawa M, Fujita K, Tanaka E, Wang E C. Assessing quality of life in the treatment of patients with age-related macular degeneration: clinical research findings and recommendations for clinical practice. Clin Ophthalmol. 2013; 7:1325-32.

Zencak D, Schouwey K, Chen D, Ekström P, Tanger E, Bremner R, van Lohuizen M, Arsenijevic Y. Retinal degeneration depends on Bmi1 function and reactivation of cell cycle proteins. Proc Natl Acad Sci USA. 2013 Feb. 12; 110(7):E593-601.

Zheng S, Xiao L, Liu Y, Wang Y, Cheng L, Zhang J, Yan N, Chen D. DZNep inhibits H3K27me3 deposition and delays retinal degeneration in the rd1 mice. Cell Death Dis. 2018 Feb. 22; 9(3):310.

TABLE 1

Table 1: Sets of primers used for genotyping

| Primer | Strand | sequence | SEQ ID NO: | Application | Reference |
|---|---|---|---|---|---|
| Rd1 | RD3 | 5'TGACAATTACTCCTTTTCCCTCAGTCTG-3' | SEQ ID NO: 1 | PCR Genotyping | Giménez & |
|  | RD4 | 5'GTAAACAGCAAGAGGCTTTATTGGGAAC-3' | SEQ ID NO: 2 |  | Montoliu; Lab Anim |
|  | RD6 | 5'TACCCACCCTTCCTAATTTTTCTCACGC-3' | SEQ ID NO: 3 |  | 2001 35: 153 |
| Bmi1 | NL-11 | 5'CGT CTG TCG AGA AGT TTC TG-3' | SEQ ID NO: 4 | PCR Genotyping |  |
|  | NL-12 | 5'AGA AGA AGA TGT TGG CGA CC-3' | SEQ ID NO: 5 |  |  |
|  | Bmi1-F | 5'AAG TGC TGT TGT CCC TGG TG-3' | SEQ ID NO: 6 |  |  |
|  | Bmi1-R | 5' AGC TCT GCC TCG TTC TCC AC-3' | SEQ ID NO: 7 |  |  |
| Gfp | Gfp-F | 5'CTG GAC GGC GAC GTA AAC-3' | SEQ ID NO: 8 | PCR Genotyping |  |
|  | Gfp-R | 5'GTC CTC CTT GAA GTC GAT GC-3' | SEQ ID NO: 9 |  |  |
| Crx-Gfp | Crx-Gfp-F | 5'CTA CGG CGT GCA GTG CTT CA-3' | SEQ ID NO: 10 | PCR Genotyping |  |
|  | Crx-Gfp-R | 5'TTC TGG TGG TAG TGG TCG GC-3' | SEQ ID NO: 11 |  |  |

TABLE 2

List of antibodies with their respective applications

| Antibodies | Species | Cat number | Dilutions | Applications | source |
|---|---|---|---|---|---|
| H3K27me3 | Rabbit | 07-449 | 1:2000\|1:500 | WB \| IHC | Millipore |
| H3K4me3 | Rabbit | 07-473 | 1:500\|1:500 | WB \| IHC | Millipore |
| H3K9me2 | Rabbit | 07-212 | 1:2000\|1:500 | WB \| IHC | Millipore |
| CDK4 | Rabbit | SC-601 | 1:500\|1:50 | WB \| IHC | Santa-Cruz |
| cGMP | Sheep |  | 1:2000 | IHC | Steinbusch (MHENS) |
| Rhodopsin(opsin) RET-P1 | Mouse | MS-1233-P | 1:1000 | IHC | Lab Vision |
| EZH2 | Mouse | 3147S | 1:200 | WB | Cell Singaling |
| GFP | Rabbit | Ab290 | 1:3000 | WB | Abcam |
| GAPDH | Mouse | MAB374 | 1:3000 | WB | Millipore |

TABLE 3

Mean number of positive cells in each day of fixation, in both groups.
Comparison between groups, Mann-Whitney test value

| | Time point | No RPE Mean value | With RPE Mean value | Mann-Whitney test No RPE vs. with RPE |
|---|---|---|---|---|
| Number of | 1 DIV | 8.99 ± 1.36 | 6.26 ± 0.65 | 0.04* |
| photoreceptor | 3 DIV | 7.19 ± 0.67 | 6.66 ± 0.57 | 0.32 |
| layers | 5 DIV | 6.24 ± 0.61 | 5.74 ± 0.52 | 0.25 |
| (mean+/− SEM) | 7 DIV | 7.11 ± 0.76 | 7.42 ± 0.98 | 0.98 |
| Number of | 1 DIV | 2.83 ± 1.03 | 1.50 ± 0.00 | 0.12 |
| TUNEL + cells | 3 DIV | 11.83 ± 6.68 | 0.75 ± 0.30 | 0.02* |
| (mean+/− SEM) | 5 DIV | 11.03 ± 2.50 | 3.75 ± 0.83 | 0.02* |
| | 7 DIV | 15.84 ± 1.73 | 7.67 ± 0.00 | 0.04* |
| Number of | 1 DIV | 1.00 ± 0.27 | 0.20 ± 0.22 | 0.04* |
| AIF + cells | 3 DIV | 8.60 ± 0.57 | 0.60 ± 0.27 | 0.02* |
| (mean+/− SEM) | 5 DIV | 0.10 ± 0.11 | 0.00 ± 0.00 | 0.05 |
| | 7 DIV | 0.00 ± 0.00 | 0.00 ± 0.00 | 1.00 |
| Number of | 1 DIV | 2.01 ± 0.75 | 0.00 ± 0.00 | 0.02* |
| CDK4 + cells | 3 DIV | 3.70 ± 0.51 | 1.65 ± 0.81 | 0.04* |
| (mean+/− SEM) | 5 DIV | 3.93 ± 2.93 | 1.13 ± 0.00 | 0.06 |
| | 7 DIV | 4.73 ± 0.86 | 1.58 ± 0.12 | 0.02* |
| Number of | 1 DIV | 1.78 ± 0.86 | 2.15 ± 3.03 | 0.05 |
| H3K27me$^3$ + cells | 3 DIV | 2.89 ± 2.64 | 1.00 ± 1.41 | 0.4 |
| (mean+/− SEM) | 5 DIV | 12.68 ± 2.06 | 1.35 ± 0.08 | 0.04* |
| | 7 DIV | 9.24 ± 1.98 | 4.07 ± 2.73 | 0.04* |

RPE-retinal pigment epithelium,
SEM-standard error of the mean,
*p < 0.05

TABLE 4

Mann-Whitney test p-values of comparison of the number of
photoreceptor layers between each time-point in the group of in
vitro RD explants (without RPE), *p < 0.05

| | Mann-Whitney test in the noRPE group, between time-points PHTORECEPTORS LAYERS | | | |
|---|---|---|---|---|
| Time-point | 1 DIV | 3 DIV | 5 DIV | 7 DIV |
| 1 DIV | | 0.11 | 0.04* | 0.03* |
| 3 DIV | | | 0.71 | 0.40 |
| 5 DIV | | | | 0.99 |
| 7 DIV | | | | |

TABLE 5

Mann-Whitney test p-values of comparison of the number
of TUNEL positive cells between each time-point in the group
of invitro RD explants (without RPE), *p < 0.05

| | Mann-Whitney test in the noRPE group, between time-points TUNEL | | | |
|---|---|---|---|---|
| Time-point | 1 DIV | 3 DIV | 5 DIV | 7 DIV |
| 1 DIV | | 0.04* | 0.02* | 0.02* |
| 3 DIV | | | 0.28 | 0.14 |
| 5 DIV | | | | 0.08 |
| 7 DIV | | | | |

TABLE 6

Mann-Whitney test p-values of comparison of the number
of CDK4 positive cells between each time-point in the group
of in vitro RD explants (without RPE), *p < 0.05

| | Mann-Whitney test in the noRPE group, between time-points CDK4 | | | |
|---|---|---|---|---|
| Time-point | 1 DIV | 3 DIV | 5 DIV | 7 DIV |
| 1 DIV | | 0.04* | 0.28 | 0.02* |
| 3 DIV | | | 0.50 | 0.08 |
| 5 DIV | | | | 0.50 |
| 7 DIV | | | | |

TABLE 7

Mann-Whitey test p-values of comparison of the number
of H3K27me$^3$ postive cells between each time-point in the
group of in vitro RD explants (without RPE), *p < 0.05

| | Mann-Whitney test in the noRPE group, between time-point H3K27me$^3$ | | | |
|---|---|---|---|---|
| Time-point | 1 DIV | 3 DIV | 5 DIV | 7 DIV |
| 1 DIV | | 0.41 | 0.02* | 0.02* |
| 3 DIV | | | 0.02* | 0.06 |
| 5 DIV | | | | 0.06 |
| 7 DIV | | | | |

What we claim is:

1. A method for treating an eye disorder characterized by degeneration or cell death of retinal neurons comprising administering to a subject in need thereof one or more inhibitors of enhancer of zeste homolog 1 (EZH1) subunit of polycomb repressive complex 2 (PRC2) which are binding EZH1 and/or enhancer of zeste homolog 2 (EZH2) subunit of polycomb repressive complex 2 (PRC2) which are binding EZH2 or their isoforms, paralogs or variants in an amount effective to alleviate the degeneration or the cell death of the retinal neurons, wherein the eye disorder characterized by the degeneration or the cell death of the retinal neurons is selected from the group consisting of color vision deficiency, retinitis pigmentosa, leber congenital amaurosis, cone rod dystrophies, night blindness, vitreoretinal dystrophies, erosive vitreoretinopathy, and usher syndrome.

2. The method according to claim 1, wherein the eye disorder is selected from the group consisting of color vision deficiency, retinal detachment, and retinitis pigmentosa.

3. The method according to claim 1, wherein the eye disorder is selected from the group consisting of leber congenital amaurosis, cone rod dystrophies, night blindness, vitreoretinal dystrophies, erosive vitreoretinopathy, and usher syndrome.

4. The method according to claim 1, wherein the eye disorder is retinitis pigmentosa.

5. The method according to claim 1, wherein said chemical compound is an EZH1 inhibitor and/or EZH2 inhibitor selected from the group consisting of UNC1999 (1-Isopropyl-6-(6-(4-isopropylpiperazin-1-yl)pyridin-3-yl)-N-((6-methyl-2-oxo-4-propyl-1,2-dihydropyridin-3-yl)methyl)-1H-indazole-4-carboxamide), EPZ005687 (1-cyclopentyl-N-[(1,2-dihydro-4,6-dimethyl-2-oxo-3-pyridinyl)methyl]-6-[4-(4-morpholinylmethyl)phenyl]-1H-indazole-4-carboxamide), EPZ-6438 (tazemetostat, N-[(1,2-dihydro-4,6-dimethyl-2-oxo-3-pyridinyl)methyl]-5-[ethyl(tetrahydro-2H-pyran-4-yl)amino]-4-methyl-4'-(4-morpholinylmethyl)-[1,1'-biphenyl]-3-carboxamide), GSK343 (N-[(1,2-dihydro-6-methyl-2-oxo-4-propyl-3-pyridinyl)methyl]-1-(1-methylethyl)-6-[2-(4-methyl-1-piperazinyl)-4-pyridinyl]-1H-indazole-4-carboxamide), GSK503 (N-[(1,2-dihydro-4,6-dimethyl-2-oxo-3-pyridinyl)methyl]-3-methyl-1-(1-methylethyl)-6-[6-(4-methyl-1-piperazinyl)-3-pyridinyl]-1H-indole-4-carboxamide), EII (6-cyano-N-[(1,2-dihydro-4,6-dimethyl-2-oxo-3-pyridinyl)methyl]-1-(1-ethylpropyl)-1H-indole-4-carboxamide), CPI-169 (N-[(1,2-dihydro-4-methoxy-6-methyl-2-oxo-3-pyridinyl)methyl]-1-[1-[1-(ethylsulfonyl)-4-piperidinyl]ethyl]-2-methyl-1H-indole-3-carboxamide), CPI-1205 ((R)-N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide), CPI-360 (N-[(1,2-dihydro-4-methoxy-6-methyl-2-oxo-3-pyridinyl)methyl]-2-methyl-1-[(1R)-1-(tetrahydro-2H-pyran-4-yl)ethyl]-1H-indole-3-carboxamide), EPZ011989 (N-[(1,2-dihydro-4,6-dimethyl-2-oxo-3-pyridinyl)methyl]-3-[ethyl[trans-4-[(2-methoxyethyl)methylamino]cyclohexyl]amino]-2-methyl-5-[3-(4-morpholinyl)-1-propyn-1-yl]-benzamide), ZLD1039 (3-[ethyl(tetrahydro-2H-pyran-4-yl)amino]-N-[(2,3,5,6,7,8-hexahydro-1-methyl-3-oxo-4-isoquinolinyl)methyl]-2-methyl-5-[6-(4-methyl-1-piperazinyl)-3-pyridinyl]-benzamide), PF-06821497 (5,8-dichloro-2-[(4-methoxy-6-methyl-2-oxo-1H-pyridin-3-yl)methyl]-7-[(R)-methoxy(oxetan-3-yl)methyl]-3,4-dihydroisoquinolin-1-one), JQEZ5 (N-[(1,2-dihydro-6-methyl-2-oxo-4-propyl-3-pyridinyl)methyl]-1-(1-methylethyl)-6-[6-(4-methyl-1-piperazinyl)-3-pyridinyl]-1H-pyrazolo[3,4-b]pyridine-4-carboxamide), JQEZ23 (N-[(1,2-dihydro-6-methyl- 2-oxo-4-propyl-3-pyridinyl)methyl]-1-(1-methylethyl)-6-[6-(4-methyl-1-piperazinyl)-3-pyridinyl]-1H-pyrazolo[3,4-b]pyridine-4-carboxamide with the substitution of the active pyridinone to a predicted inactive pyridinium ring), 5R-(4-amino-IH-imidazo[4,5-c]pyridin-1-yl)-3-(hydroxymethyl)-3-cyclopentene-IS,2R-diol, Sinefungin (6,9-diamino-1-(6-amino-9H-purin-9-yl)-1,5,6,7,8,9-hexadeoxy-D-glycero-α-L-talo-decofuranuronic acid), and analogs, functional derivatives or pharmaceutically acceptable salt thereof.

6. A method for treating an eye disorder characterized by degeneration or cell death of retinal neurons comprising administering to a subject in need thereof one or more inhibitors of enhancer of zeste homolog 1 (EZH1) subunit of polycomb repressive complex 2 (PRC2) which are binding EZH1 and/or enhancer of zeste homolog 2 (EZH2) subunit of polycomb repressive complex 2 (PRC2) which are binding EZH2 or their isoforms, paralogs or variants in an amount effective to alleviate the degeneration or the cell death of the retinal neurons, wherein the eye disorder characterized by the degeneration or the cell death of the retinal neurons is selected from the group consisting of inherited retinal disorder, retinal degeneration, neurodegenerative disease of the retina, ocular autoimmune disease affecting the retina and inflammatory disease affecting the retina, color vision deficiency, computer vision syndrome, floaters & spots, glaucoma, learning-related vision problems, macular degeneration, nystagmus, ocular allergies, ocular hypertension, retinal detachment, retinitis pigmentosa, subconjunctival hemorrhage, uveitis, leber congenital amaurosis, cone rod dystrophies, night blindness, vitreoretinal dystrophies, erosive vitreoretinopathy, usher syndrome, epiretinal membrane, and macular hole, wherein said EZH1 inhibitor and/or EZH2 inhibitor is UNC1999.

7. The method according to claim 1, wherein said EZH1 inhibitor and/or EZH2 inhibitor is EPZ-6438.

8. The method according to claim 1, wherein the eye disorder is selected from the group consisting of erosive vitreoretinopathy and, usher syndrome.

9. The method according to claim 1, further comprising administering to the subject one or more additional therapeutic agents.

10. The method according to claim 1, further comprising administering to the subject one or more additional therapeutic agents, that are not inhibitors of a subunit of PRC2.

11. The method according to claim 1, further comprising administering to the subject one or more additional therapeutic agents selected among therapeutic agents used for treating an eye disorder in a subject.

12. The method of claim 1, wherein the method is for treating the eye disorder and the one or more inhibitors bind the EZH2.

13. The method of claim 1, wherein the retinal neurons are photoreceptors and the amount administered is sufficient to alleviate the degeneration or the cell death of the photoreceptors.

14. The method of claim 13, wherein the photoreceptors are rod photoreceptors.

15. The method of claim 1, wherein the one or more inhibitors are administered via intravitreal injection.

16. The method according to claim 1, wherein the eye disorder is selected from the group consisting of retinitis pigmentosa, leber congenital amaurosis, cone rod dystrophies, night blindness, vitreoretinal dystrophies, erosive vitreoretinopathy, and retinal detachment.

17. A method for treating an eye disorder characterized by degeneration or cell death of retinal neurons comprising administering to a subject in need thereof one or more inhibitors of enhancer of zeste homolog 1 (EZH1) subunit of polycomb repressive complex 2 (PRC2) which are binding EZH1 and/or enhancer of zeste homolog 2 (EZH2) subunit of polycomb repressive complex 2 (PRC2) which are binding EZH2 or their isoforms, paralogs or variants in an amount effective to alleviate the degeneration or the cell death of the retinal neurons, wherein the eye disorder characterized by the degeneration or the cell death of the retinal neurons is selected from the group consisting of inherited retinal disorder, retinal degeneration, neurodegenerative disease of the retina, ocular autoimmune disease affecting the retina and inflammatory disease affecting the retina, color vision deficiency, computer vision syndrome, floaters & spots, glaucoma, learning-related vision problems, macular degeneration, nystagmus, ocular allergies, ocular hypertension, retinal detachment, retinitis pigmentosa, subconjunctival hemorrhage, leber congenital amaurosis, cone rod dystrophies, night blindness, vitreoretinal dystrophies, erosive vitreoretinopathy, usher syndrome, epiretinal membrane, and macular hole, wherein said chemical compound is an EZH1 inhibitor and/or EZH2 inhibitor selected from the group consisting of UNC1999 (1-Isopropyl-6-(6-(4-isopropylpiperazin-1-yl)pyridin-3-yl)-N-((6-methyl-2-oxo-4-propyl-1,2-dihydropyridin-3-yl)methyl)-1H-indazole-4-carboxamide), EPZ005687 (1-cyclopentyl-N-[(1,2-dihydro-4,6-dimethyl-2-oxo-3-pyridinyl)methyl]-6-[4-(4-morpholinylmethyl)phenyl]-1H-indazole-4-carboxamide), EPZ-6438 (tazemetostat, N-[(1,2-dihydro-4,6-dimethyl-2-oxo-3-pyridinyl)methyl]-5-[ethyl(tetrahydro-2H-pyran-4-yl)amino]-4-methyl-4'-(4-morpholinylmethyl)-[1,1'-biphenyl]-3-carboxamide), GSK343 (N-[(1,2-dihydro-6-methyl-2-oxo-4-propyl-3-pyridinyl)methyl]-1-(1-methylethyl)-6-[2-(4-methyl-1-piperazinyl)-4-pyridinyl]-1H-indazole-4-carboxamide), GSK503 (N-[(1,2-dihydro-4,6-dimethyl-2-oxo-3-pyridinyl)methyl]-3-methyl-1-(1-methylethyl)-6-[6-(4-methyl-1-piperazinyl)-3-pyridinyl]-1H-indole-4-carboxamide), EII (6-cyano-N-[(1,2-dihydro-4,6-dimethyl-2-oxo-3-pyridinyl)methyl]-1-(1-ethylpropyl)-1H-indole-4-carboxamide), CPI-169 (N-[(1,2-dihydro-4-methoxy-6-methyl-2-oxo-3-pyridinyl)methyl]-1-[1-[1-(ethylsulfonyl)-4-piperidinyl]ethyl]-2-methyl-1H-indole-3-carboxamide), CPI-1205 ((R)-N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide), CPI-360 (N-[(1,2-dihydro-4-methoxy-6-methyl-2-oxo-3-pyridinyl)methyl]-2-methyl-1-[(1R)-1-(tetrahydro-2H-pyran-4-yl)ethyl]-1H-indole-3-carboxamide), EPZ011989 (N-[(1,2-dihydro-4,6-dimethyl-2-oxo-3-pyridinyl)methyl]-3-[ethyl[trans-4-[(2-methoxyethyl)methylamino]cyclohexyl]amino]-2-methyl-5-[3-(4-morpholinyl)-1-propyn-1-yl]-benzamide), ZLD1039 (3-[ethyl(tetrahydro-2H-pyran-4-yl)amino]-N-[(2,3,5,6,7,8-hexahydro-1-methyl-3-oxo-4-isoquinolinyl)methyl]-2-methyl-5-[6-(4-methyl-1-piperazinyl)-3-pyridinyl]-benzamide), PF-06821497 (5,8-dichloro-2-[(4-methoxy-6-methyl-2-oxo-1H-pyridin-3-yl)methyl]-7-[(R)-methoxy(oxetan-3-yl) methyl]-3,4-dihydroisoquinolin-1-one), JQEZ5 (N-[(1, 2-dihydro-6-methyl-2-oxo-4-propyl-3-pyridinyl) methyl]-1-(1-methylethyl)-6-[6-(4-methyl-1-piperazinyl)-3-pyridinyl]-1H-pyrazolo[3,4-b]pyridine-4-carboxamide), JQEZ23 (N-[(1,2-dihydro-6-methyl-2-oxo-4-propyl-3-pyridinyl)methyl]-1-(1-methylethyl)-6-[6-(4-methyl-1-piperazinyl)-3-pyridinyl]-1H-pyrazolo[3,4-b]pyridine-4-carboxamide with the substitution of the active pyridinone to a predicted inactive pyridinium ring), 5R-(4-amino-IH-imidazo[4,5-c]pyridin-1-yl)-3-(hydroxymethyl)-3-cyclopentene-IS,2R-diol, Sinefungin (6,9-diamino-1-(6-amino-9H-purin-9-yl)-1,5,6,7,8,9-hexadeoxy-D-glycero-α-L-talo-decofuranuronic acid), and analogs, functional derivatives or pharmaceutically acceptable salt thereof.

\* \* \* \* \*

SEQUENCE LISTING

<160> NUMBER OF SEQ ID NOS: 11

<210> SEQ ID NO 1
<211> LENGTH: 28
<212> TYPE: DNA
<213> ORGANISM: Artificial Sequence
<220> FEATURE:
<223> OTHER INFORMATION: Synthetic primer

<400> SEQUENCE: 1
tgacaattac tccttttccc tcagtctg                                          28

<210> SEQ ID NO 2
<211> LENGTH: 28
<212> TYPE: DNA
<213> ORGANISM: Artificial Sequence
<220> FEATURE:
<223> OTHER INFORMATION: Synthetic primer

<400> SEQUENCE: 2

```
gtaaacagca agaggcttta ttgggaac                                        28

<210> SEQ ID NO 3
<211> LENGTH: 28
<212> TYPE: DNA
<213> ORGANISM: Artificial Sequence
<220> FEATURE:
<223> OTHER INFORMATION: Synthetic primer

<400> SEQUENCE: 3
tacccaccct tcctaatttt tctcacgc                                        28

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
cgtctgtcga gaagtttctg                                                 20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
agaagaagat gttggcgacc                                                 20

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
aagtgctgtt gtccctggtg                                                 20

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
agctctgcct cgttctccac                                                 20

<210> SEQ ID NO 8
<211> LENGTH: 18
<212> TYPE: DNA
<213> ORGANISM: Artificial Sequence
<220> FEATURE:
<223> OTHER INFORMATION: Synthetic primer

<400> SEQUENCE: 8
ctggacggcg acgtaaac                                                   18

<210> SEQ ID NO 9
<211> LENGTH: 20
<212> TYPE: DNA
```

-continued

<213> ORGANISM: Artificial Sequence
<220> FEATURE:
<223> OTHER INFORMATION: Synthetic primer

<400> SEQUENCE: 9
gtcctccttg aagtcgatgc                                        20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
ctacggcgtg cagtgcttca                                        20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
ttctggtggt agtggtcggc                                        20